United States Patent
Xuan et al.

(10) Patent No.: US 12,180,534 B2
(45) Date of Patent: Dec. 31, 2024

(54) CONDITIONAL PRIMER EXTENSION FOR SINGLE-MOLECULE DETECTION

(71) Applicant: President and Fellows of Harvard College, Cambridge, MA (US)

(72) Inventors: Feng Xuan, Cambridge, MA (US); Peng Yin, Cambridge, MA (US); Mingjie Dai, Cambridge, MA (US); Xi Chen, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 256 days.

(21) Appl. No.: 17/523,611

(22) Filed: Nov. 10, 2021

(65) Prior Publication Data

US 2022/0064699 A1    Mar. 3, 2022

Related U.S. Application Data

(62) Division of application No. 16/304,323, filed as application No. PCT/US2017/034630 on May 26, 2017, now Pat. No. 11,208,676.

(60) Provisional application No. 62/342,401, filed on May 27, 2016.

(51) Int. Cl.
*C07H 21/02* (2006.01)
*C12Q 1/6804* (2018.01)
*C40B 70/00* (2006.01)

(52) U.S. Cl.
CPC ............ *C12Q 1/6804* (2013.01); *C40B 70/00* (2013.01)

(58) Field of Classification Search
USPC ....... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS

| | | |
|---|---|---|
| 6,511,809 B2 | 1/2003 | Baez et al. |
| 7,306,904 B2 | 12/2007 | Landegren et al. |
| 7,914,987 B2 | 3/2011 | Fredriksson et al. |
| 7,932,060 B2 | 4/2011 | Nadeau et al. |
| 8,338,579 B2 | 12/2012 | Adams et al. |
| 9,012,156 B2 | 4/2015 | Patterson |
| 9,176,123 B2 | 11/2015 | Le et al. |
| 9,677,131 B2 | 6/2017 | Fredriksson et al. |
| 9,777,315 B2 | 10/2017 | Fredriksson et al. |
| 9,809,848 B2 | 11/2017 | Jones |
| 9,862,994 B2 | 1/2018 | Schmidt et al. |
| 10,669,569 B2 | 6/2020 | Gullberg et al. |
| 10,745,746 B2 | 8/2020 | Chen et al. |
| 10,781,473 B2 | 9/2020 | Fredriksson et al. |
| 11,208,676 B2 | 12/2021 | Xuan et al. |

(Continued)

FOREIGN PATENT DOCUMENTS

| | | |
|---|---|---|
| WO | 2004/094456 A2 | 11/2004 |
| WO | 2011/022820 A1 | 3/2011 |

(Continued)

OTHER PUBLICATIONS

Extended European Search Report mailed Dec. 20, 2019, for Application No. EP 17803647.1.

(Continued)

*Primary Examiner* — Frank W Lu

(74) *Attorney, Agent, or Firm* — Wolf, Greenfield & Sacks, P.C.

(57) ABSTRACT

The present disclosure provides, in some embodiments, methods and compositions for single-molecule detection.

9 Claims, 35 Drawing Sheets

(56) References Cited

U.S. PATENT DOCUMENTS

| | | |
|---|---|---|
| 2007/0026430 A1 | 2/2007 | Andersen et al. |
| 2010/0279882 A1 | 11/2010 | Ronaghi et al. |
| 2011/0223585 A1 | 9/2011 | Gullberg et al. |
| 2012/0238738 A1 | 9/2012 | Hendrickson |
| 2013/0274135 A1 | 10/2013 | Zhang et al. |
| 2014/0212869 A1 | 7/2014 | Sampas et al. |
| 2015/0024972 A1 | 1/2015 | Schmidt et al. |
| 2015/0044674 A1 | 2/2015 | Fredriksson et al. |
| 2016/0153036 A1 | 6/2016 | Chen et al. |
| 2018/0094309 A1 | 4/2018 | Chen et al. |
| 2019/0136294 A1 | 5/2019 | Xuan et al. |
| 2022/0127600 A1 | 4/2022 | Wang et al. |

FOREIGN PATENT DOCUMENTS

| | | |
|---|---|---|
| WO | 2012/058488 A1 | 5/2012 |
| WO | 2013/113699 A2 | 8/2013 |
| WO | 2014/130388 A1 | 8/2014 |
| WO | 2015/010020 A1 | 1/2015 |
| WO | 2015/019247 A1 | 2/2015 |
| WO | 2016/123419 A1 | 8/2016 |
| WO | 2017/143006 A1 | 8/2017 |
| WO | 2017/205719 A1 | 11/2017 |

OTHER PUBLICATIONS

International Search Report and Written Opinion mailed Aug. 25, 2017 for Application No. PCT/US2017/034630.

International Preliminary Report on Patentability mailed Dec. 6, 2018 for Application No. PCT/US2017/034630.

Chun et al., Dual priming oligonucleotide system for the multiplex detection of respiratory viruses and SNP genotyping of CYP2C19 gene. Nucl Acids Res. 2007;35:e40(1-6).

Lundberg et al., Homogeneous antibody-based proximity extension assays provide sensitive and specific detection of low-abundant proteins in human blood. Nucl Acids Res. Aug. 2011;39(15):e102.

Nong et al., DNA-assisted protein detection technologies. Expert Rev Proteomics. 2012;9(1):21-32.

Yurke et al., A DNA-fuelled molecular machine made of DNA. Nature. Aug. 1, 20000;406(6796):605-8.

Zhang et al., Dynamic DNA nanotechnology using strand-displacement reactions. Nat Chem. Feb. 2011;3(2):103-13.

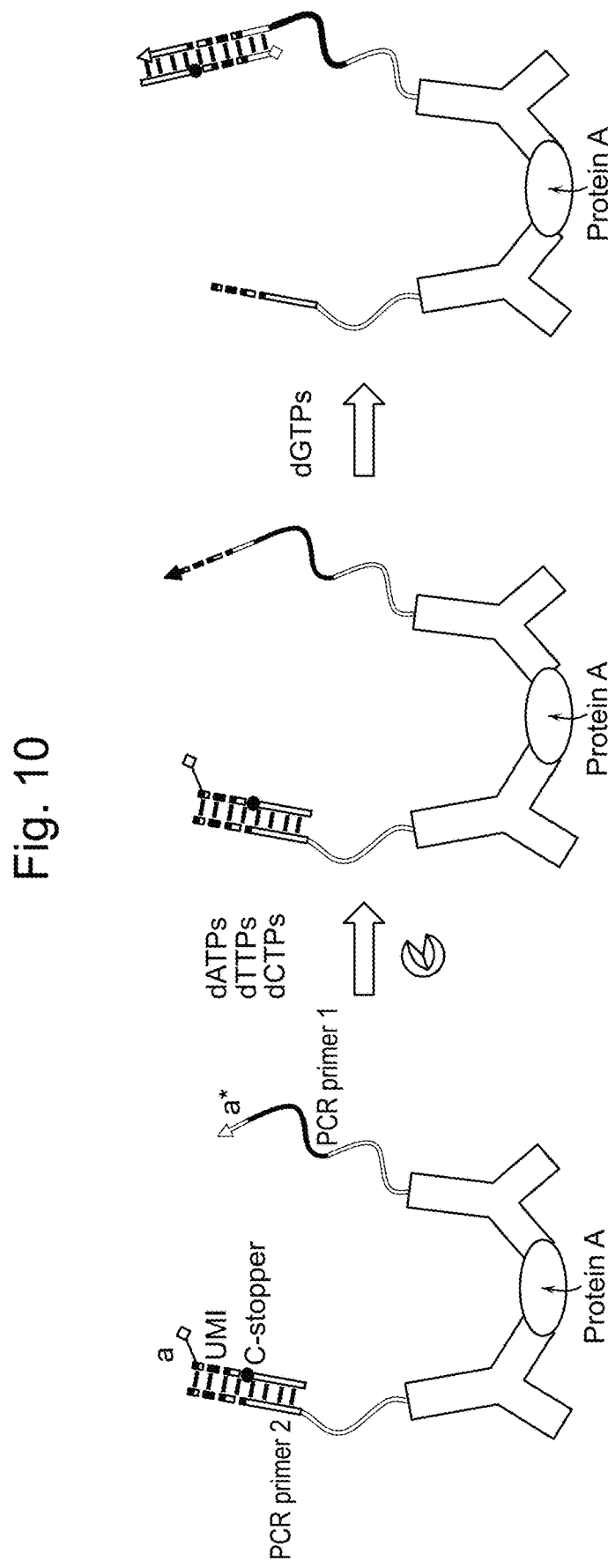

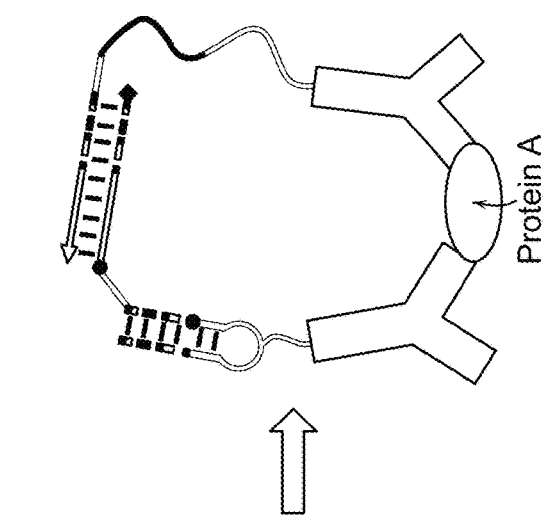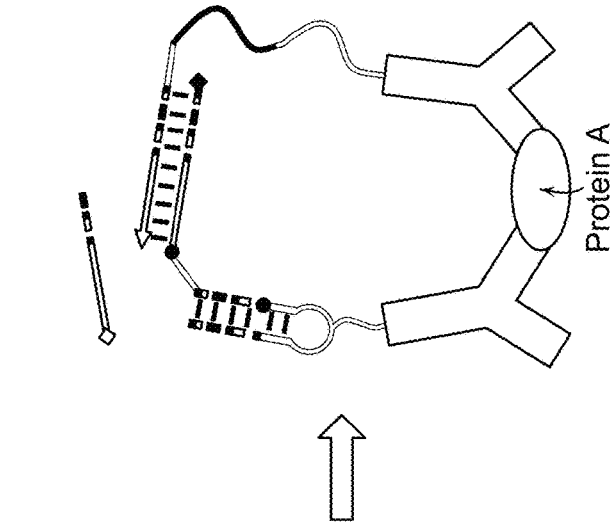
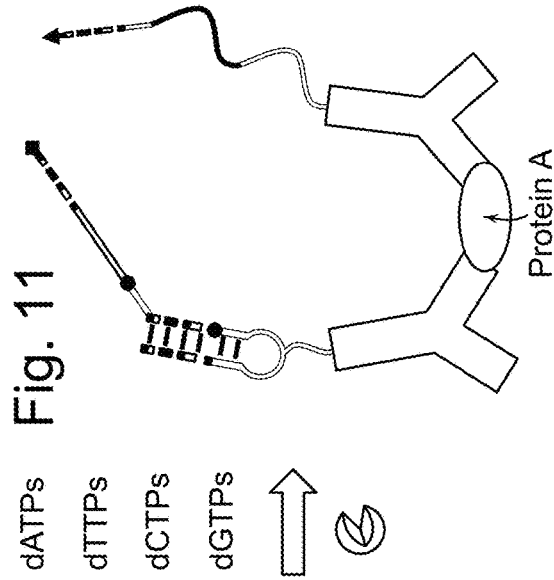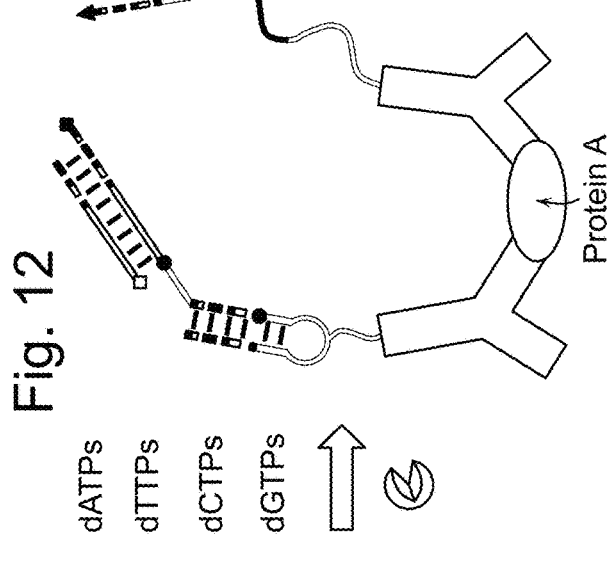
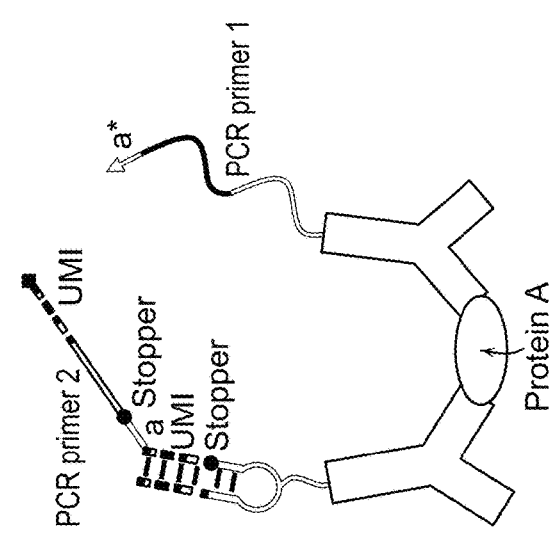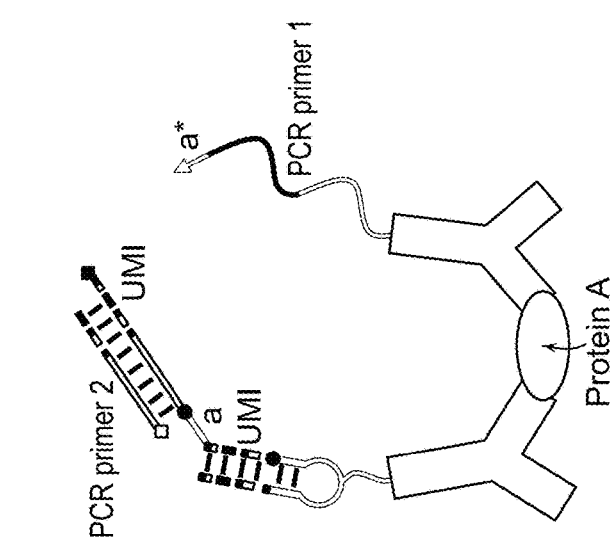

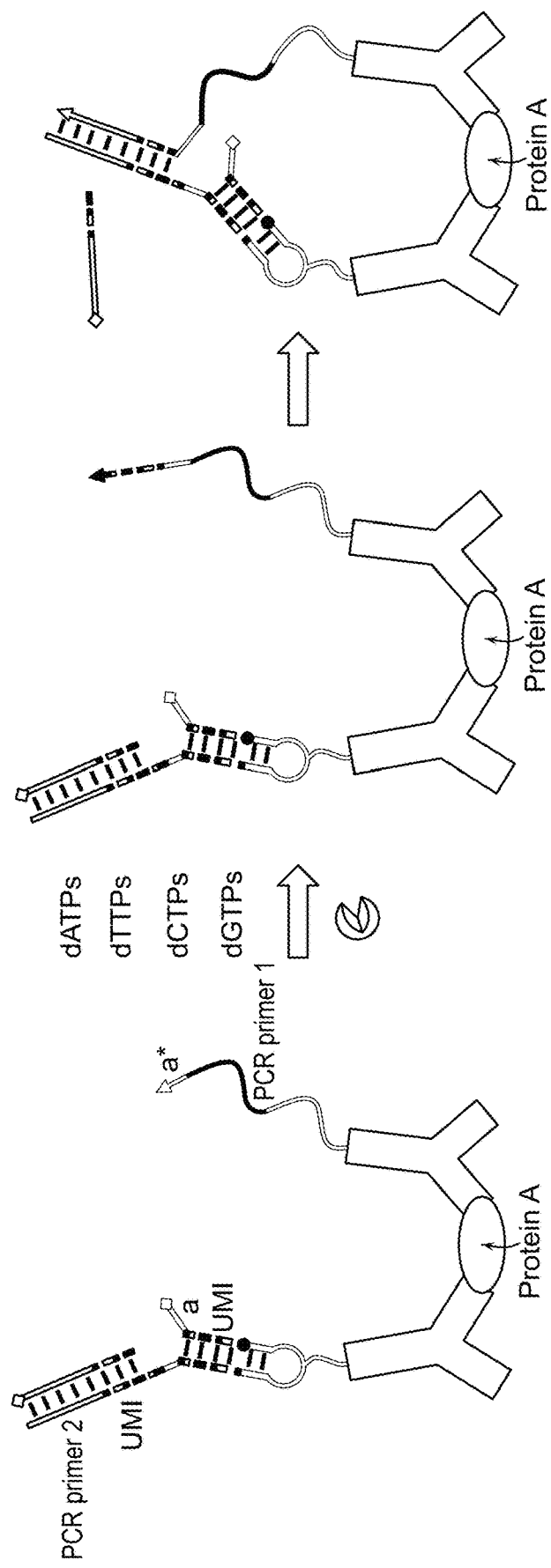

Fig. 15
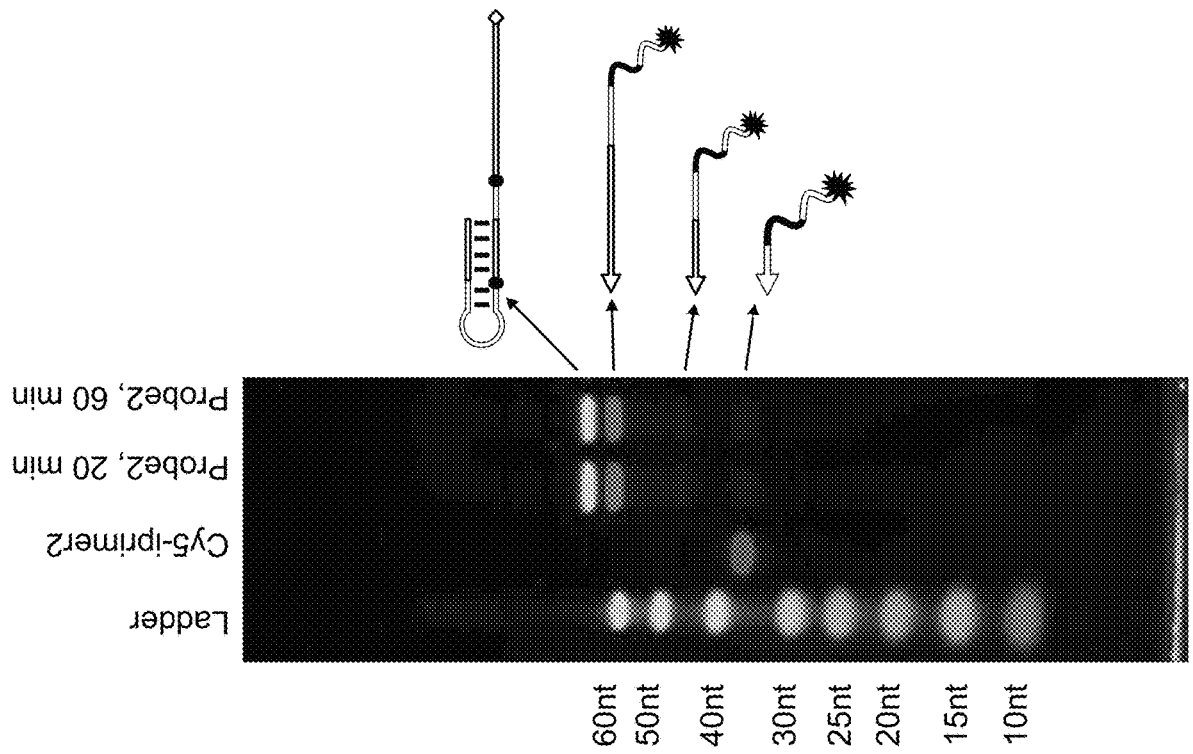
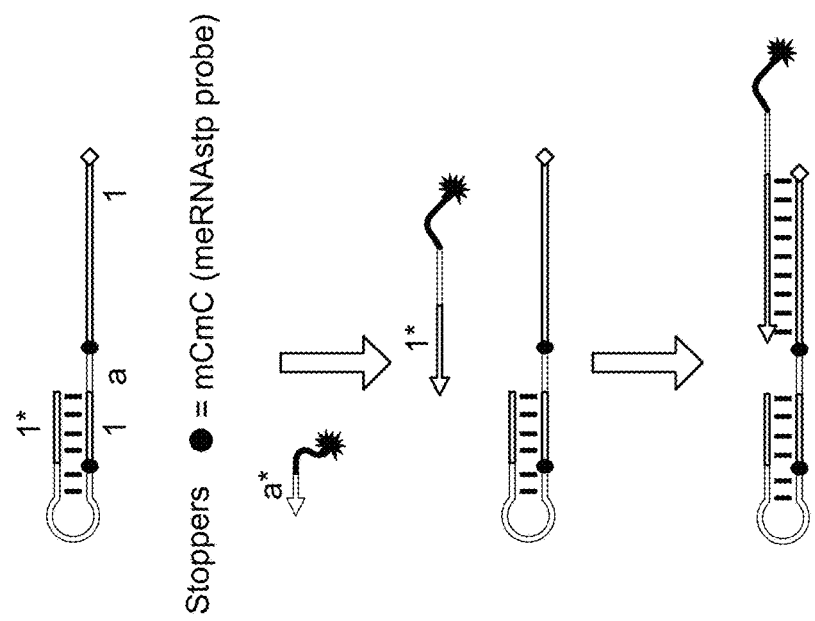

Fig. 17
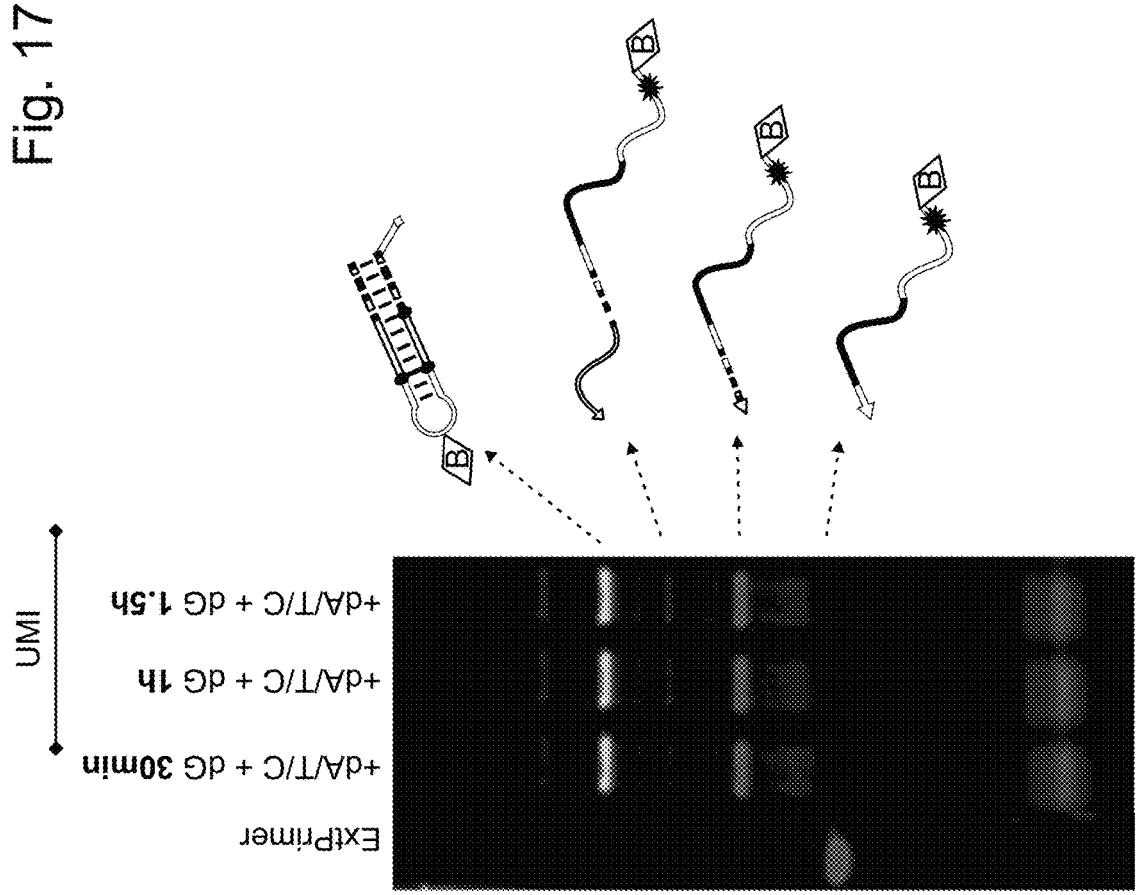
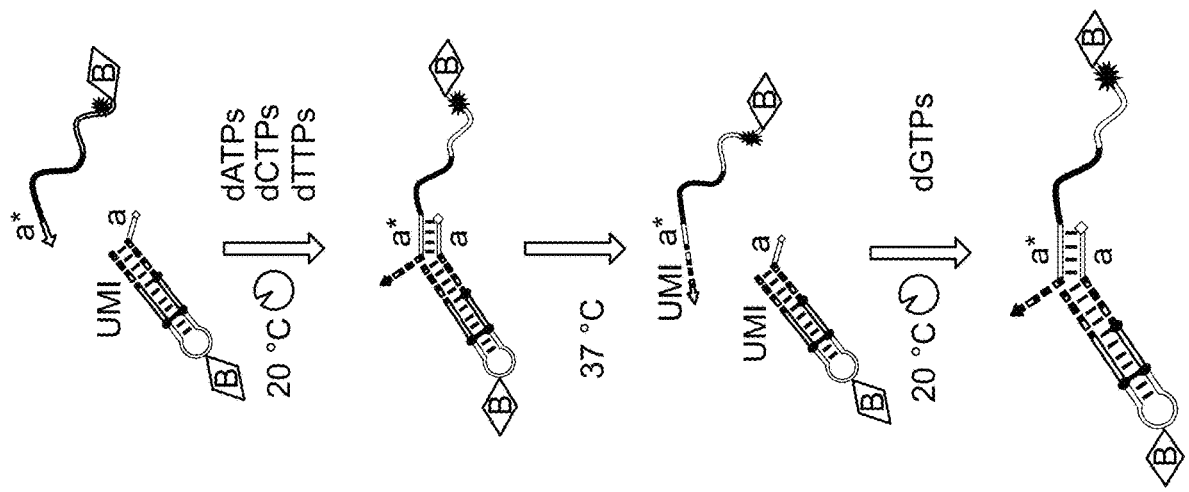

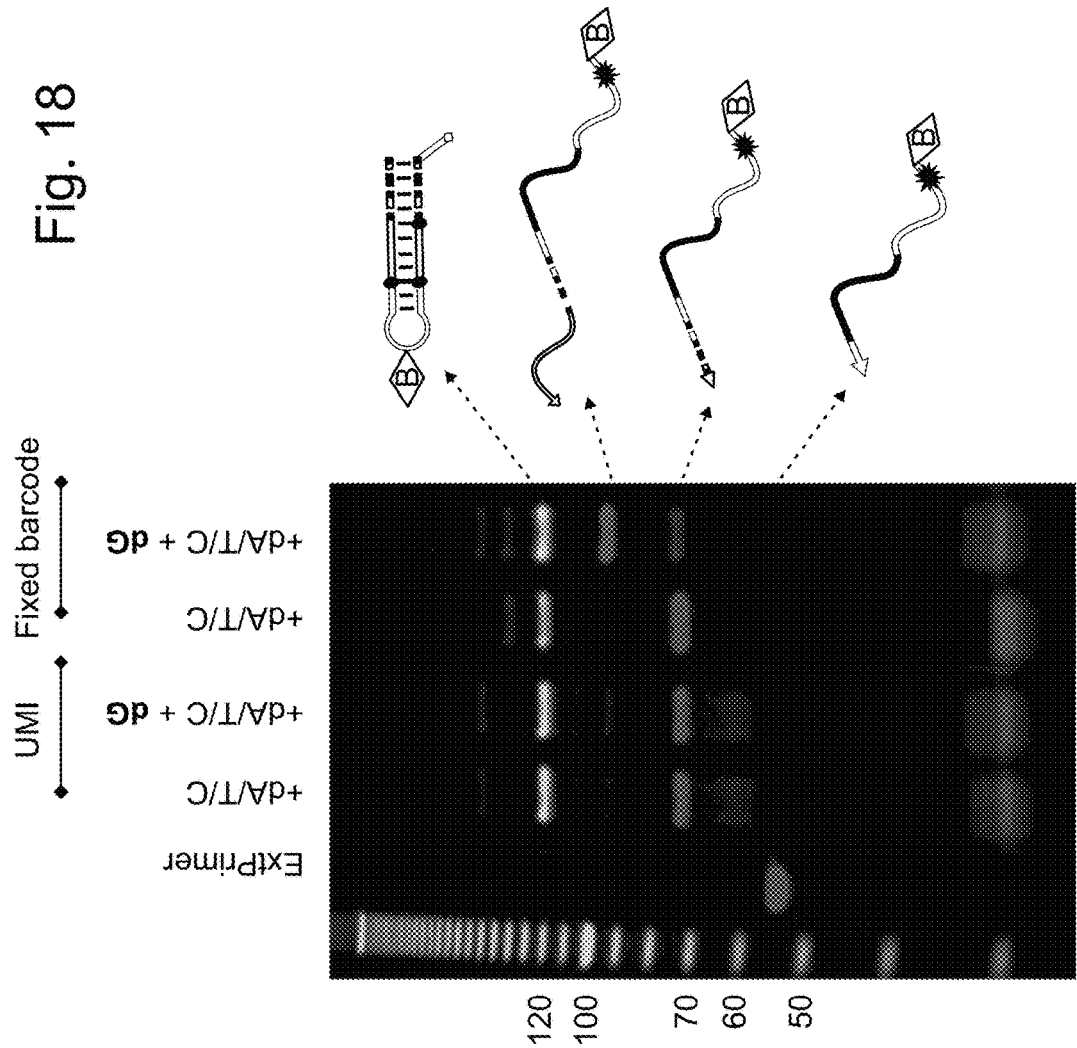
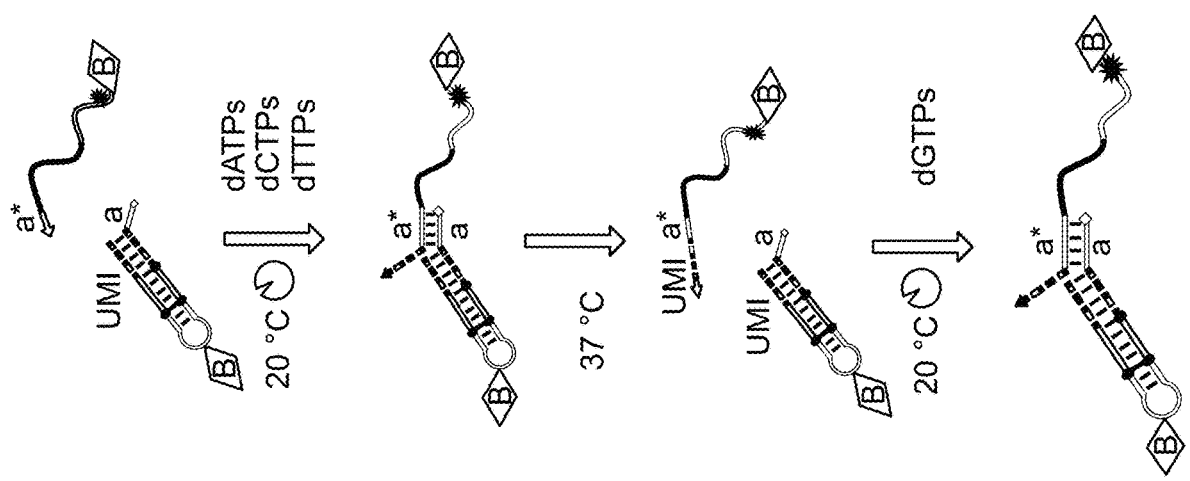
Fig. 18

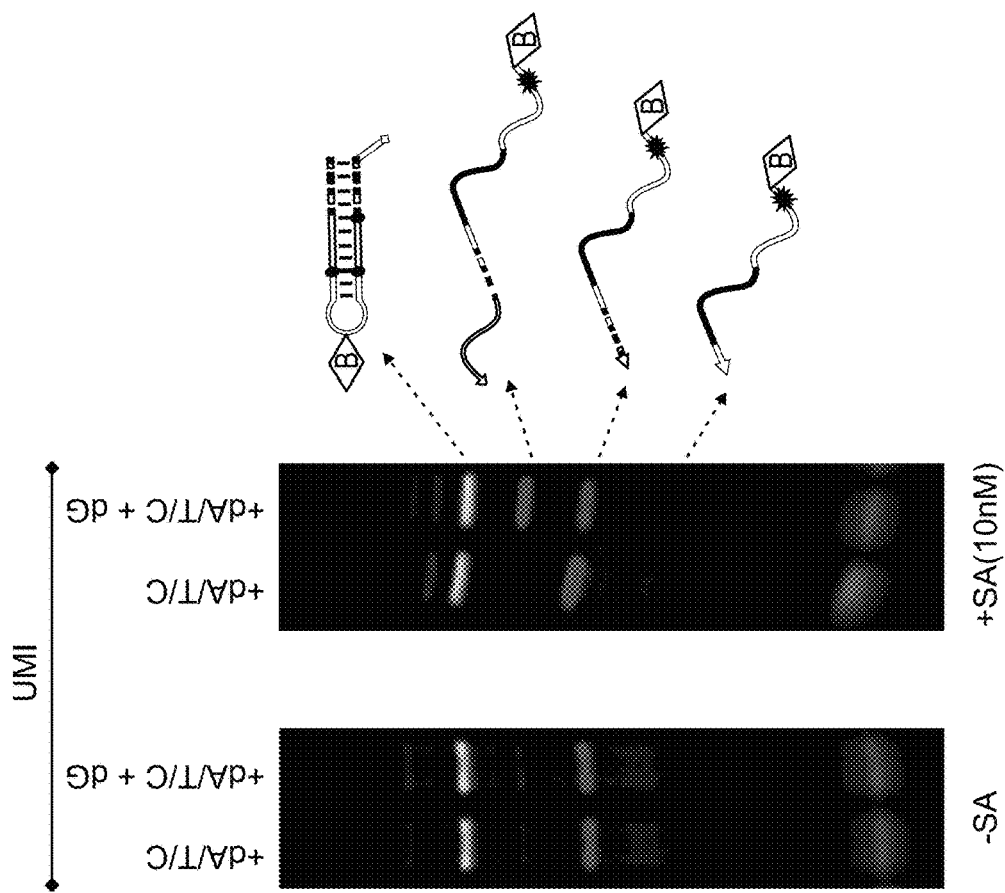
Fig. 19
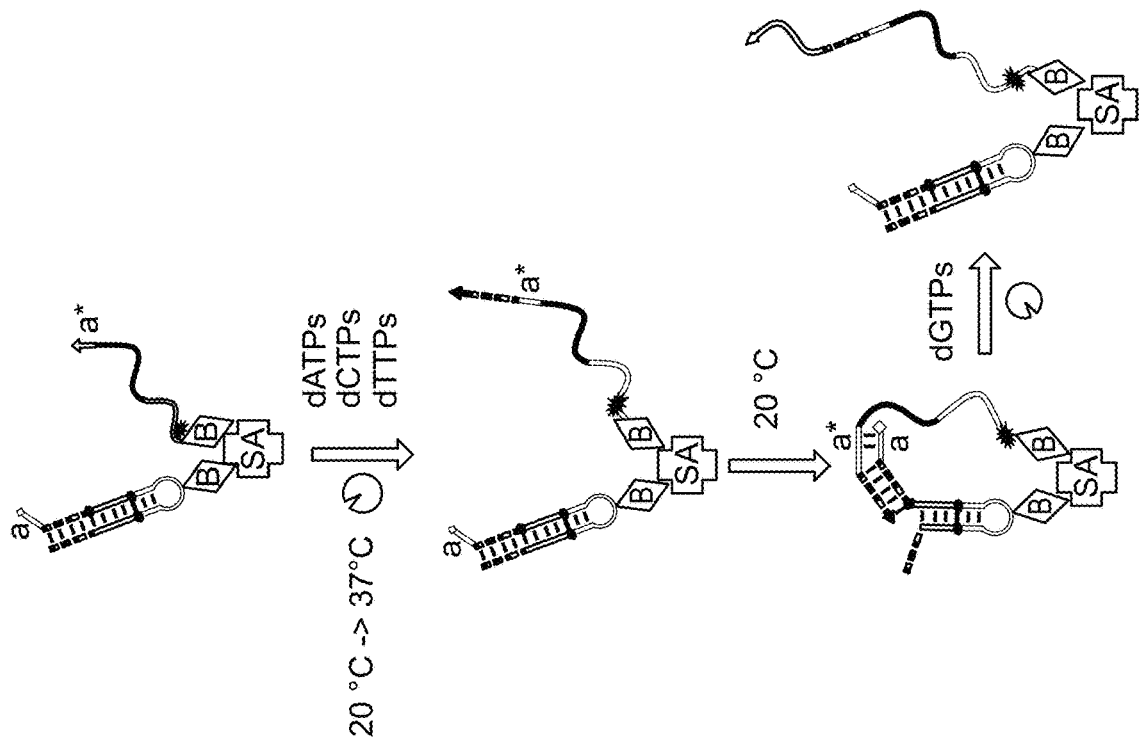

Fig. 20
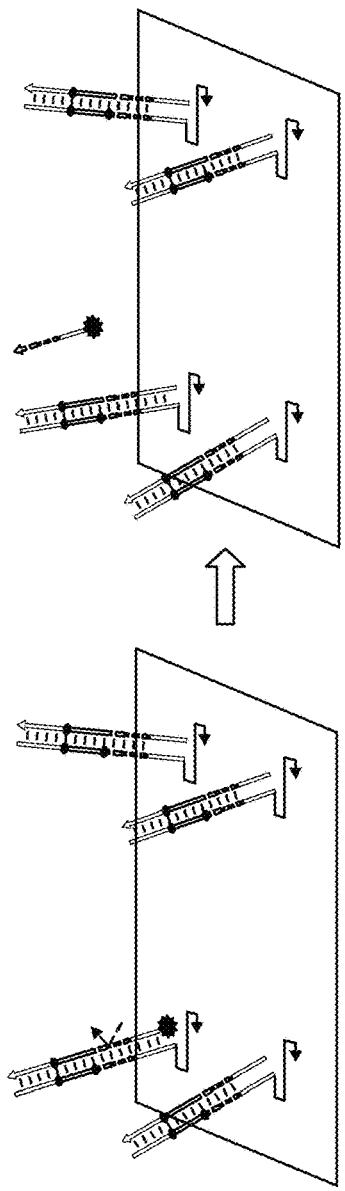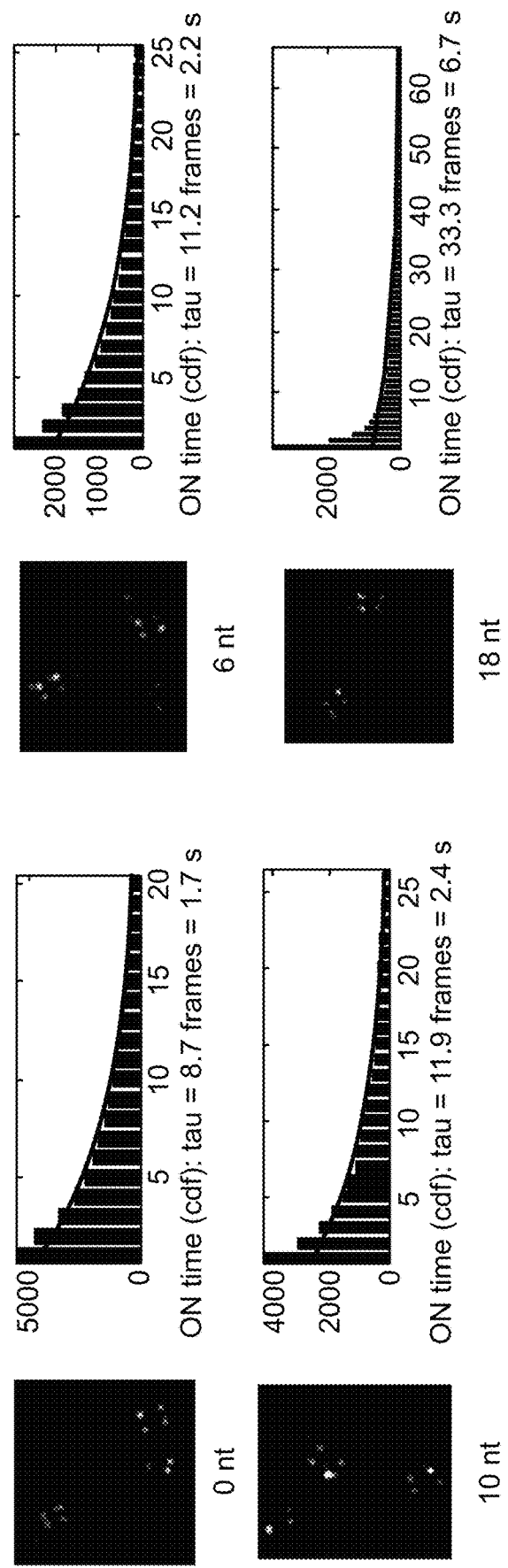

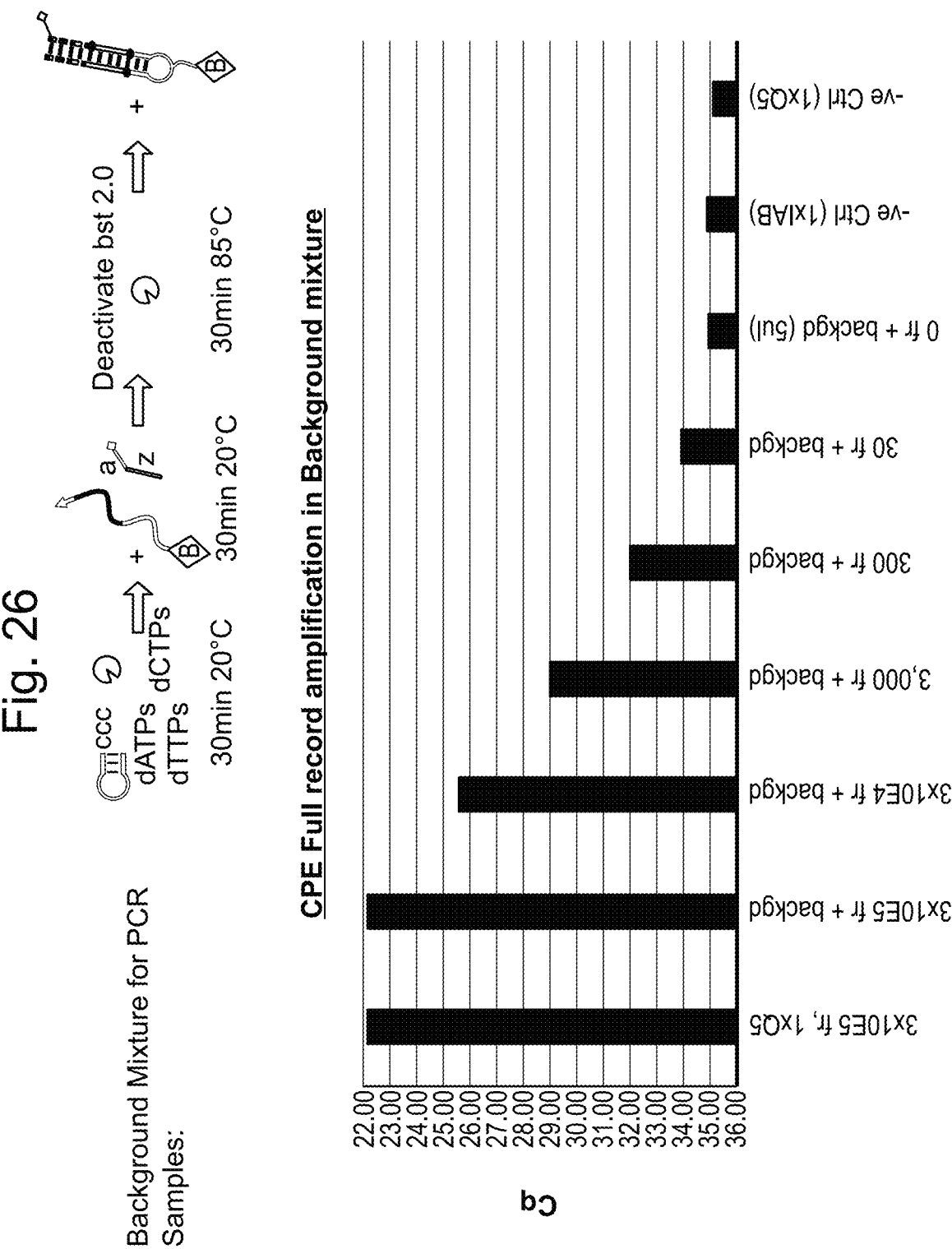

Fig. 30
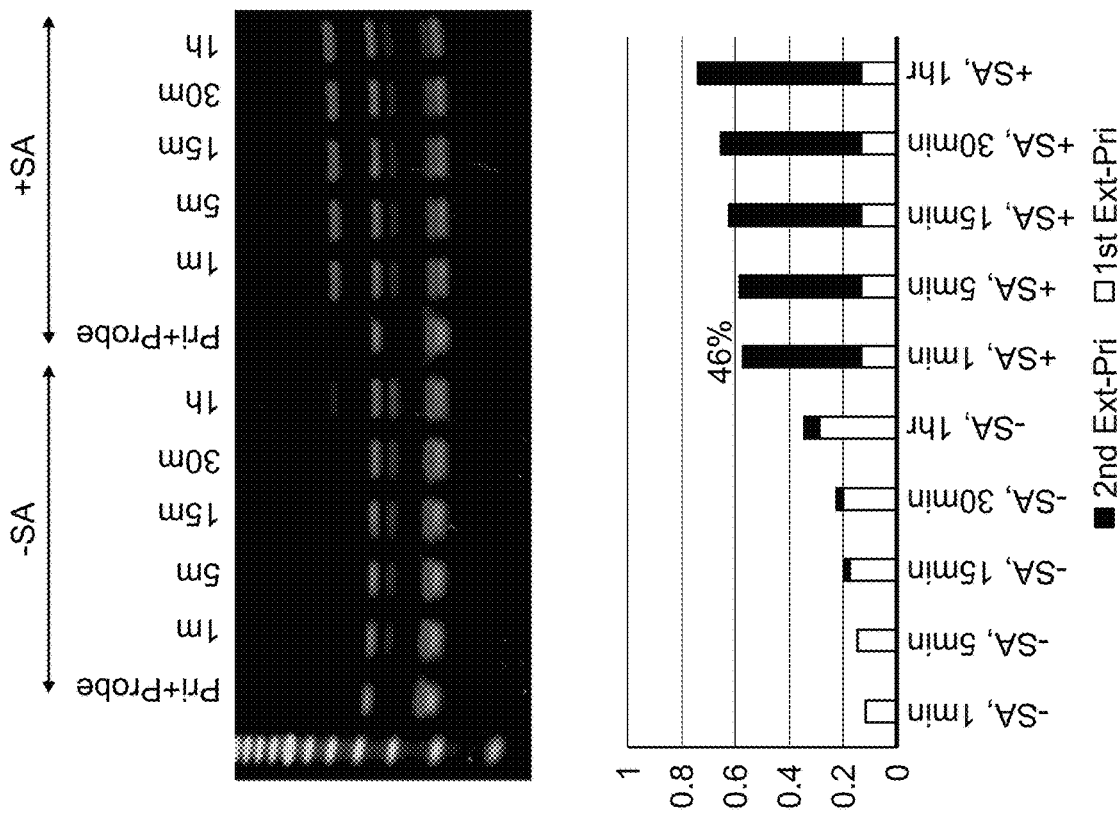
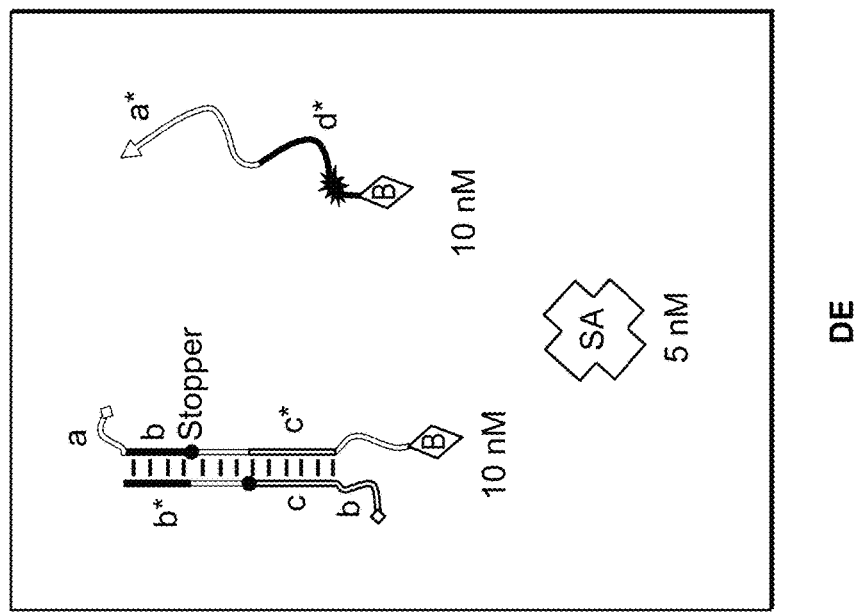

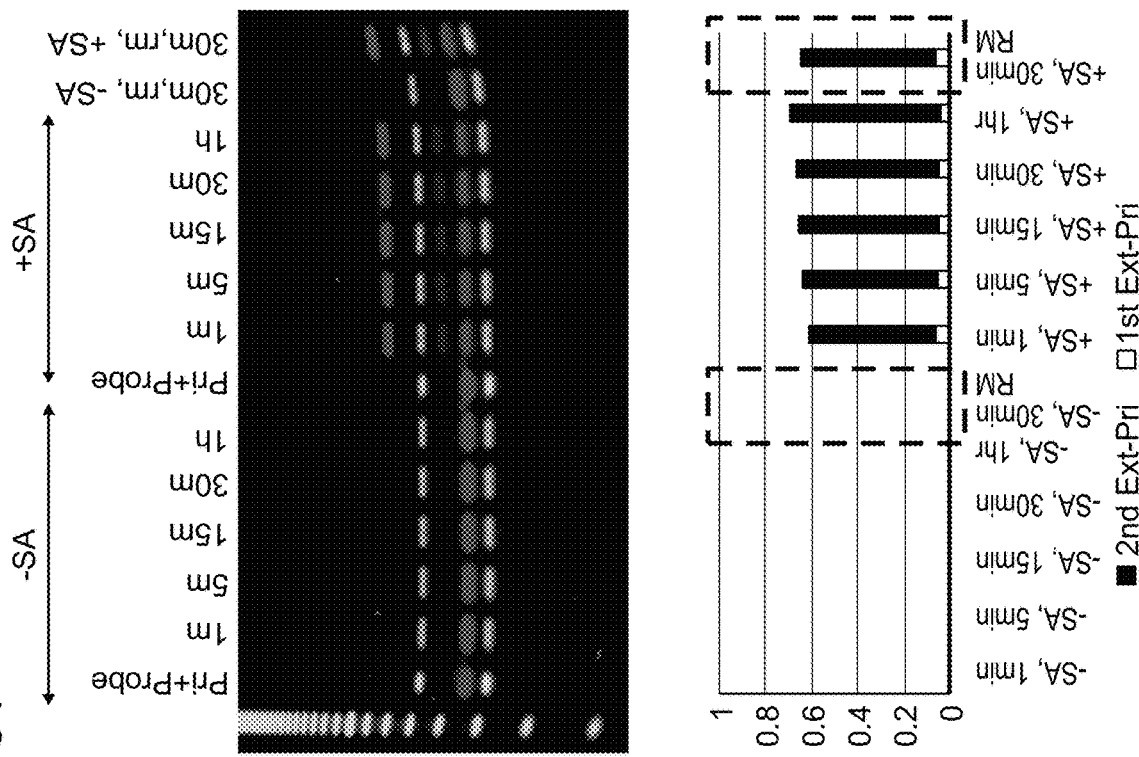
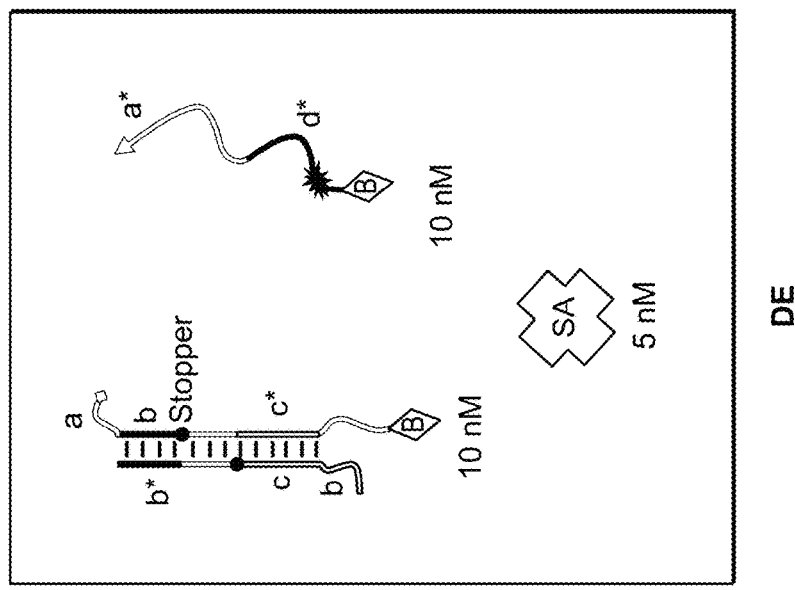
Fig. 31

Fig. 33
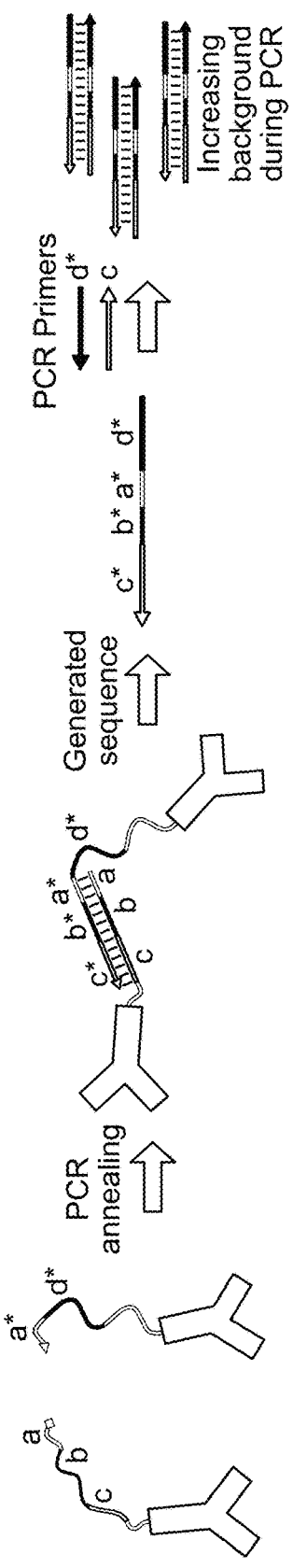
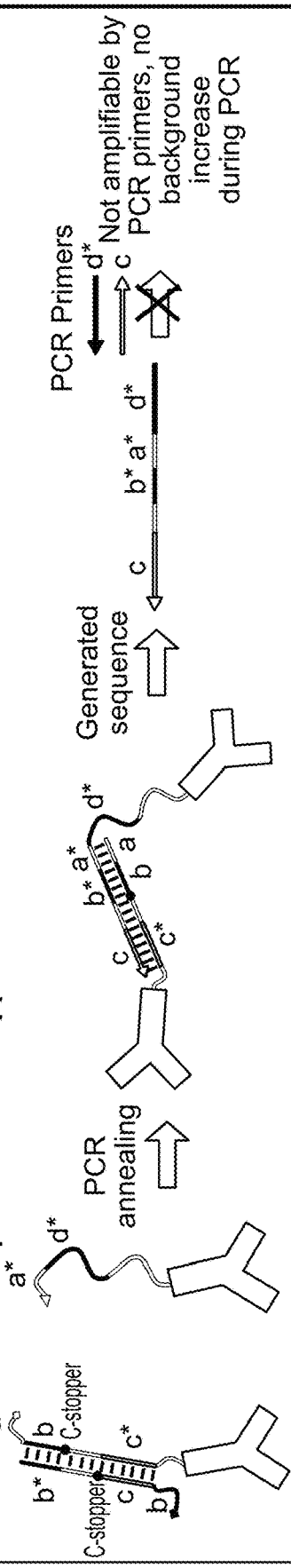

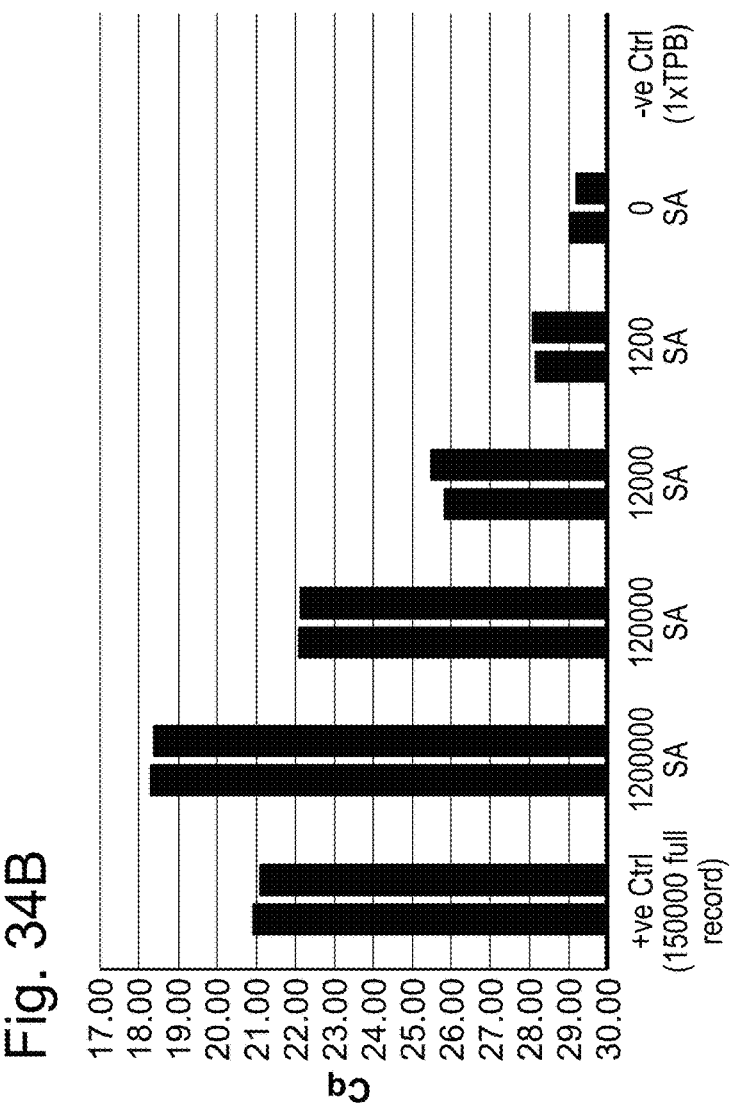
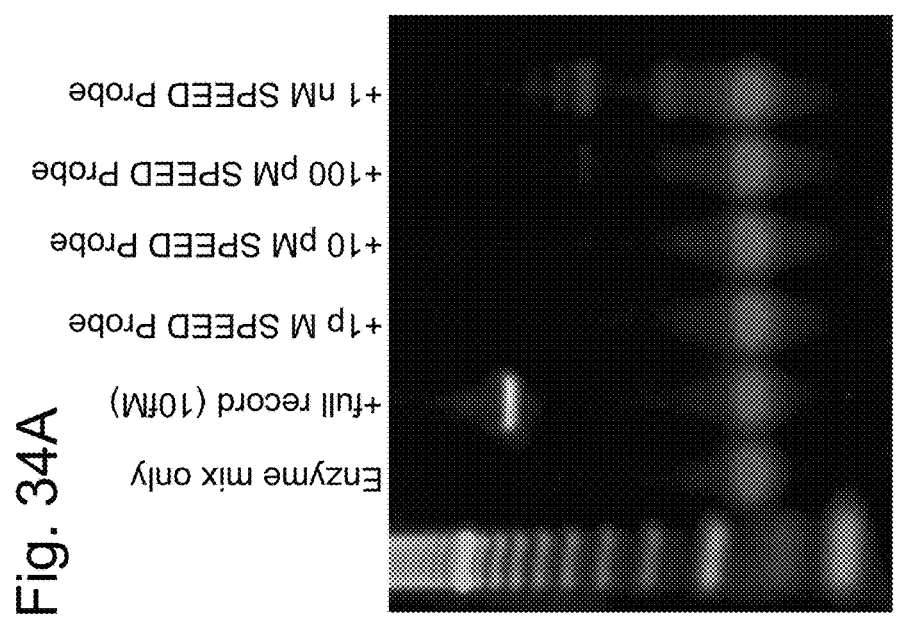
Fig. 34B
Fig. 34A

CONDITIONAL PRIMER EXTENSION FOR SINGLE-MOLECULE DETECTION

This application is a divisional of U.S. patent application Ser. No. 16/304,323, filed Nov. 26, 2018, which is a national stage filing under 35 U.S.C. § 371 of international application number PCT/US2017/034630, filed May 26, 2017, which was published under PCT Article 21(2) in English and claims the benefit under 35 U.S.C. § 119(e) of U.S. provisional application No. 62/342,401, filed May 27, 2016, each of which is incorporated by reference herein in its entirety.

This invention was made with government support under N00014-13-1-0593 and N00014-14-1-0610 awarded by U.S. Office of Naval Research (NAVY/ONR) and under EB018659 and GM133052 awarded by National Institutes of Health (NIH) and under 1317291 awarded by National Science Foundation (NSF). The government has certain rights in this invention.

BACKGROUND

Single molecule detection methods have become powerful tools for analyzing individual molecules masked by an ensemble of components in complex biological systems. These methods can be used to detect disease biomarkers that correlate with many diseases during early stages of the disease, where treatment has the greatest potential to improve prognosis and survival rates. Despite the significance of being able to detect a single molecule, doing so has remained a challenge, particular in high-throughput and multiplex assay formats.

SUMMARY

Provided herein, in some embodiments, are methods, compositions and kits for identification and quantification of target analytes, for example proteins, from a biological sample having a level of sensitivity to detect a single molecule (e.g., protein or nucleic acid). The methods of the present disclosure use differences in interaction times between binding and non-binding moieties to generate an amplifiable nucleic acid molecule only when two nucleic acid probes recognize the same target (FIG. 1).

A single target protein may be detected, for example, using a pair of nucleic acid probes (see. e.g., FIG. 2). The first nucleic acid probe is conjugated to a first antibody that recognizes a first epitope on the target protein. The first nucleic acid probe comprises (i) a 5' paired domain comprising a 5' primer-binding subdomain 'PCR primer 2' linked to a 3' barcode subdomain 'UMI' (unique molecular identifier) wherein the 3' barcode subdomain 'UMI' is formed by base pairing between a sequence of nucleotides that lacks one of A, T, C or G, and a complementary sequence of nucleotides, and (ii) a 3' unpaired primer-binding domain 'a', wherein a nucleotide corresponding to the nucleotide lacking from the 3' barcode subdomain (UMI) is located between the 3' barcode subdomain (UMI) and the 5' primer-binding subdomain 'PCR primer 2', and wherein the 5' primer-binding subdomain 'PCR primer 2' comprises a 5' molecule that terminates polymerization. The second nucleic acid probe is conjugated to a second antibody that recognizes a second epitope on the target protein. The second nucleic acid probe comprises a 5' primer-binding domain 'PCR primer 1' linked to a 3' primer domain—'a*' that is complementary to the 3' unpaired primer-binding domain 'a' of the first nucleic acid probe.

The methods of the present disclosure make use of a strand displacement mechanism to generate an amplifiable nucleic acid molecule only when two nucleic acid barcoded probes are co-localized on their target (see, e.g. FIG. 3) "Strand displacement" refers to the mechanism by which two nucleic acid strands with identical sequences, when proximate to a single complementary nucleic acid strand (or segment of a strand), undergo relatively rapid (e.g., timescale<1s) competition for that complement strand, 'displacing' each other from the complement presumably by a 'random-walk' mechanism (see, e.g., Yurke et al, Nature 406, 605-608, 2000; and Zhang et al. Nature Chemistry 3: 103-113, 2011, each of which is incorporated by reference herein).

When the pair of nucleic acid probes are co-localized on their target, domain 'a' in the first probe binds to domain 'a*' in the second probe. In the presence of dATPs, dTTPs and dCTPs, a strand displacing polymerase extends along the strand until it reaches a "stopper" molecule represented by black dots. This extension results in a newly formed UMI domain appended to primer domain 'a*'. The probes remain bound to their target, which allows the newly formed UMI domain appended to the primer domain 'a*' to compete with the UMI domain of the first probe for binding to their complementary domain. The newly formed UMI domain in primer domain 'a*' displaces the UMI domain of the first probe and the strand displacing polymerase, in the presence of dGTPs, extends along the primer domain 'a*'. This extension appends a second primer-binding domain 'PCR primer 2' to primer domain "a*". The resulting nucleic acid provides an amplifiable record that is used to detect the presence of a target protein.

In the absence of a target protein, the pair of nucleic acid probes cannot generate an amplifiable nucleic acid molecule (see, e.g., FIG. 4). A pair of nucleic acid probes unbound by a target protein will randomly encounter each other in solution allowing the primer domain 'a' in the first probe to bind to the primer domain 'a*' in the second probe. The strand displacing polymerase extends along the strand appending a newly formed UMI domain to the primer domain 'a*'. The pair of probes separate and will remain separated in the absence of a common target protein. This separation prevents the newly formed UMI domain of the primer domain 'a*' from binding to the first probe and displacing the UMI domain of the first probe, and thus a second primer-binding domain 'PCR primer 2' cannot be appended to primer domain 'a*' The resulting nucleic acid cannot be amplified and a target protein is not detected.

A single target protein may be also detected, for example, using a pair of nucleic acid probes that are configured such that a 'UMI' sequence is not required (see, e.g., FIGS. 28, 29 and 35); instead two or more (e.g., two, three, four, or more) toehold domains and two or more (e.g., two, three, four, or more) stopper molecules may be used on a single probe of the pair, to enable conditional primer extension. For example, the first nucleic acid probe (e.g., linked to an antibody) may comprise two or more (e.g., two, three, four, or more) nuclei acid strands, bound to each other, and each strand including a 3' unpaired toehold domain and a stopper molecule (see, e.g., FIG. 28). The second nucleic acid probe (e.g., linked to another antibody) may comprise a 3' unpaired primer-binding domain capable of binding to one of the 3' toehold domains of the first nucleic acid probe. Through primer binding, extension, and strand-displacement mechanisms, records of the antibody interactions are generated.

BRIEF DESCRIPTION OF DRAWINGS

FIG. 10 shows an example of a pair of nucleic acid probes of the present disclosure.

FIG. 11 shows an example of a pair of nucleic acid probes of the present disclosure.

FIG. 12 shows an example of a pair of nucleic acid probes of the present disclosure.

FIG. 13 shows an example of a pair of nucleic acid probes of the present disclosure.

FIG. 15 shows an example of sequential primer extension reaction on a hairpin probe.

FIG. 17 shows data demonstrating the effectiveness of the UMI. When not co-localized with the CPE hairpins (and after dissociating from the original hairpins), the extension primers imprinted with the UMI generated only a low yield of visible full records (background records).

FIG. 18 shows data further demonstrating the effectiveness of the UMI. When not co-localized with the CPE hairpins (and after dissociating from the original hairpins), the extension primers imprinted with fixed barcodes, rather than the UMI, generated a high yield of full records.

FIG. 19 shows data demonstrating the use of UMI to confirm co-localization events. When co-localized with the CPE hairpins via a biotin-streptavidin linkage (and after dissociating from the hairpins), the extension primers imprinted with the UMI generated a high yield of full records.

FIG. 20 shows data from experiments characterizing dissociation kinetics by single molecule imaging. The UMI-imprinted extension primer is able to dissociate from the CPE hairpin relatively quickly, even with longer lengths of UMI.

FIG. 30 shows data demonstrating the use of a SPEED reaction to detect a streptavidin (SA). The probes are labeled with biotin.

FIG. 31 shows additional data demonstrating the use of a SPEED reaction using probes of varying length and sequence composition.

FIG. 33 is a schematic demonstrating that a "flipped" PCR primer binding domain design eliminates background signal generated during PCR amplification. When high concentration of probe is needed to boost the binding between affinity probes and targets, the SPEED probe, with C-stoppers, does not introduce background during PCR amplification, because the extension sequence generated is not amplifiable by the PCR primers.

FIGS. 34A-34B show data demonstrating that SPEED performs efficiently even at high probe concentrations. FIG. 34A shows that there were no observable full records amplified following 25 cycles of PCR when a probe concentration in the range 1 pM to 1 nM was used.

FIG. 34B shows qPCR data indicating that the SPEED reaction may be used to detect approximately 1200 copies of streptavidin, even when 1 nM of biotin-labeled SPEED probe is used. Data from two repeat experiments is shown.

DESCRIPTION

Figure 1:
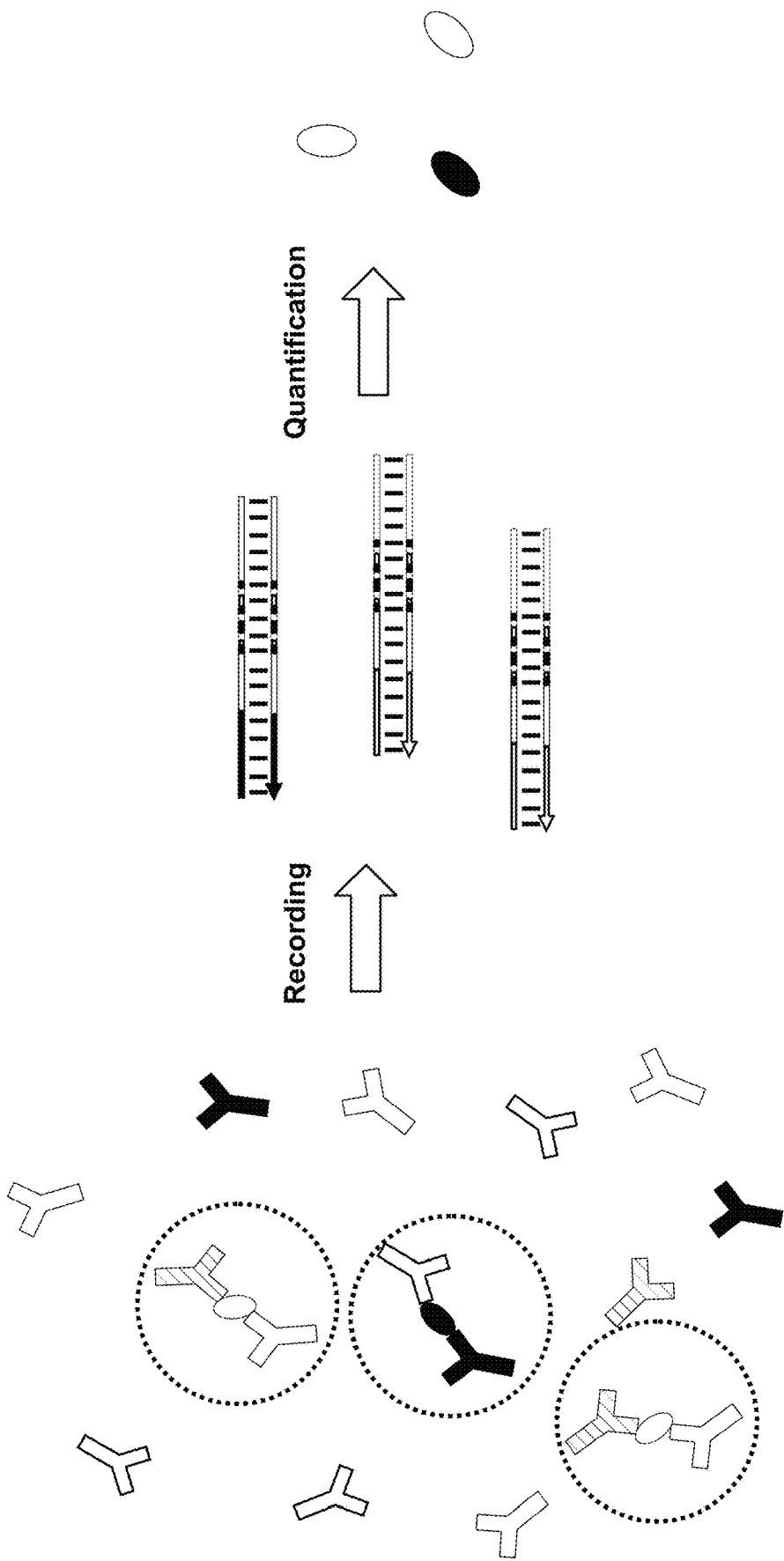
FIG. 1 shows an example of a method of the present disclosure.

The methods, compositions and kits, as provided herein, enable detection of target analytes from a biological sample with single-molecule sensitivity. The methods generate an amplifiable nucleic acid molecule only when two nucleic acid probes recognize a specific target of interest (FIG. 1).

Figure 2:
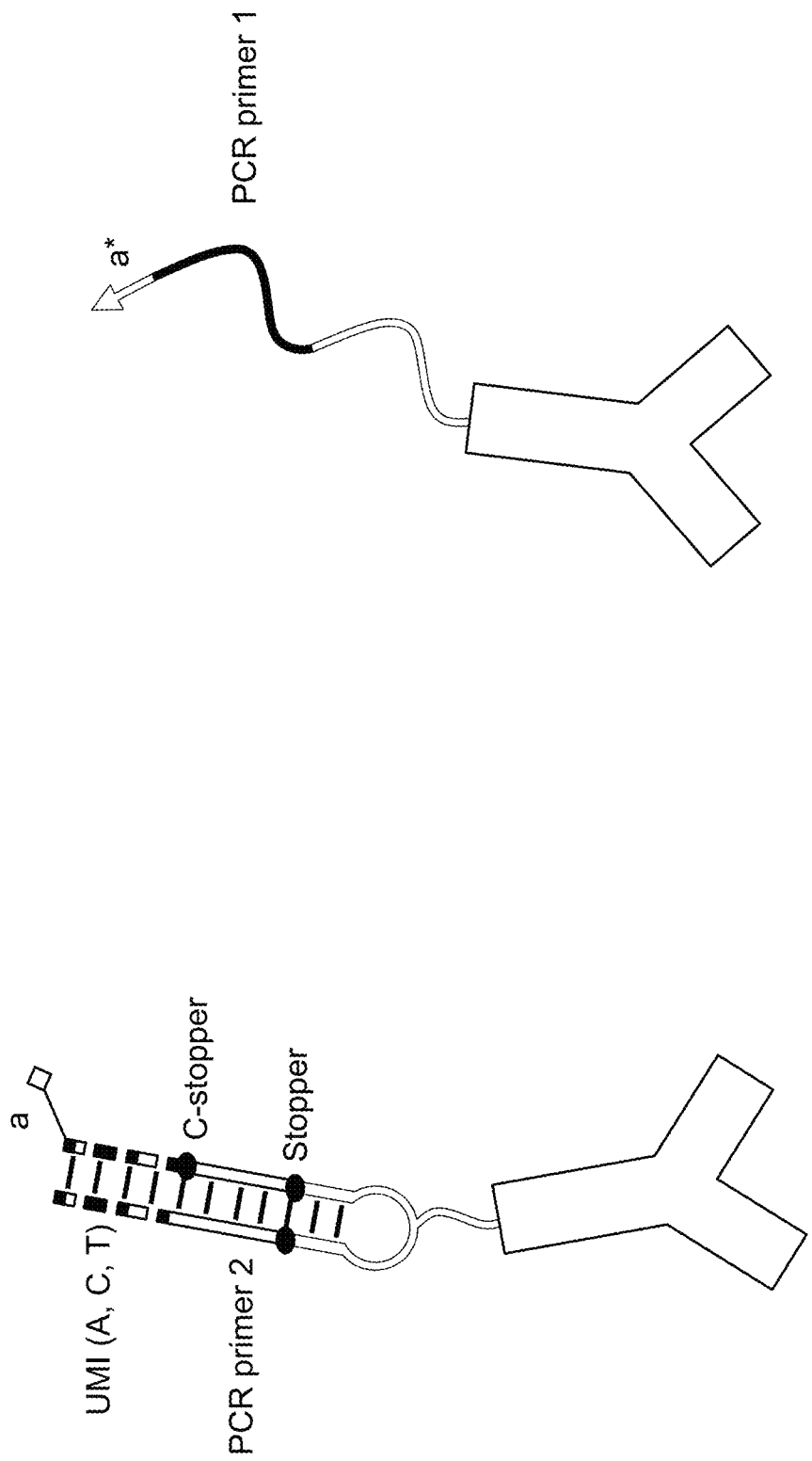
FIG. 2 shows an example of a pair of nucleic acid probes.

Nucleic acid probes may be conjugated to detection molecules (e.g., antibodies) for single-molecule protein detection (FIG. 2). Single-molecule protein detection via, generation of an amplifiable nucleic acid molecule is shown, for example, in FIG. 3. In the absence of a target protein, an amplifiable nucleic acid molecule cannot be generated as shown, for example, in FIG. 4.

Figure 3:
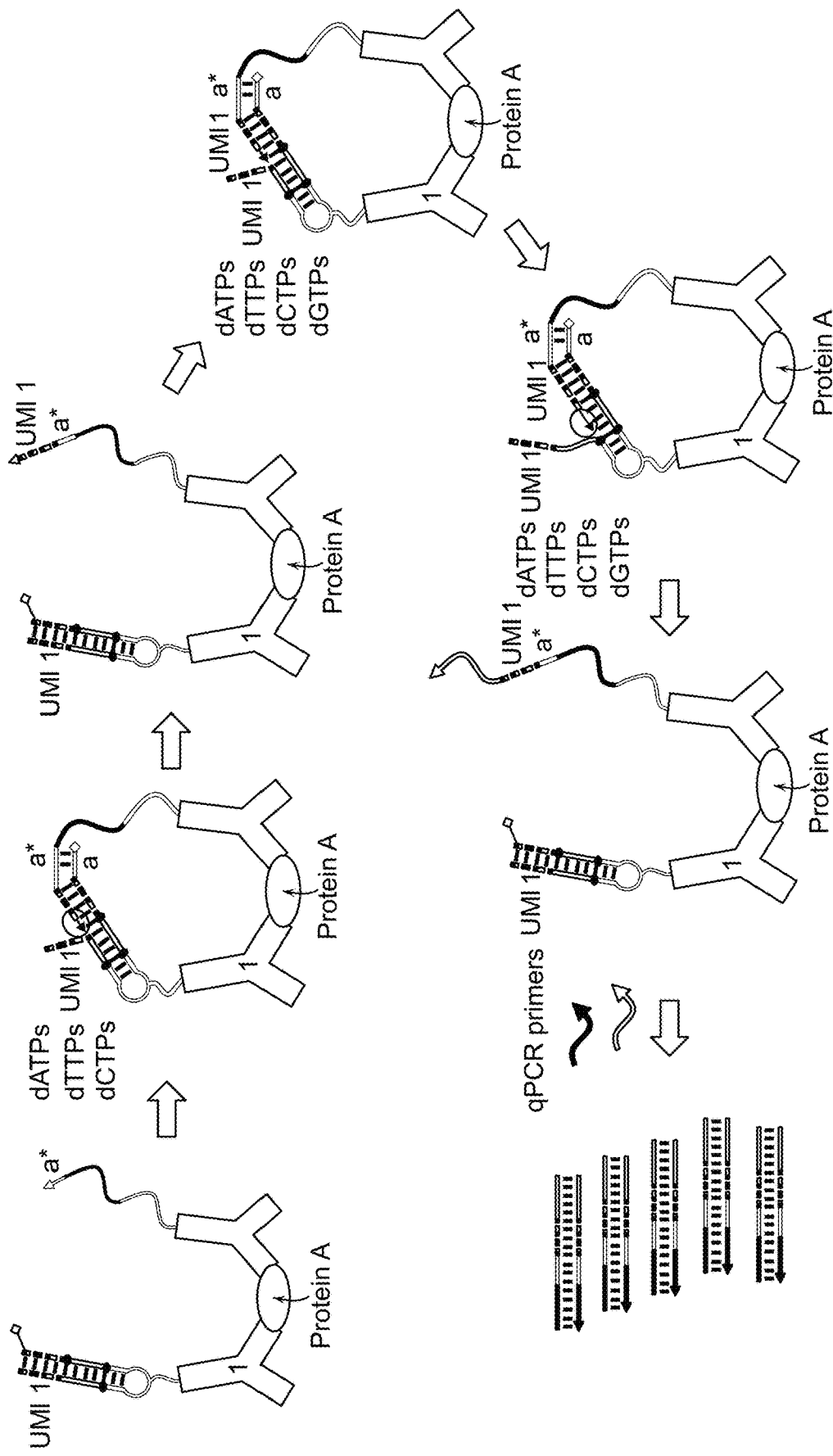
FIG. 3 shows an example of a method of the present disclosure in the presence of a target.

FIG. 3 provides an example of a method of detecting a target protein using the pair of barcode probes described in FIG. 2. Each probe is bound to a different antibody that recognizes a different epitope of the same target protein. When both antibodies are bound to the target proteins, a nucleic acid record/amplification template containing primer binding sites, reflective of that specific interaction is generated. As shown in FIG. 3, for example, the pair of nucleic acid probes is incubated in reaction buffer comprising strand displacing polymerase at a temperature at which the strand displacing polymerase is active. In the initial step of the reaction, the reaction buffer includes a mixture of dNTPs that lacks the particular dNTP that corresponds to the complement of the nucleotide lacking from the 3' barcode subdomain 'UMI' of the first nucleic acid probe—in this example, dGTP. If the target protein is present, the probes, including the bound antibodies, will bind to their respective epitopes on the target protein. The 3' unpaired primer domain 'a*' of the second probe binds to the 3' primer-binding domain 'a' of the first probe, and the polymerase extends the 3' end of the primer domain along the 3' barcode subdomain until it reaches the 'C-stopper' molecule (black dot), thereby replicating the 'UMI' sequence and displacing the original 'UMI' sequence. Because both the original 'UMI' sequence and the newly formed copy are identical, they compete for binding to the complementary sequence of the 3' barcode subdomain a mechanism referred to as strand displacement. Binding of the original 'UMI' sequence to the complementary sequence of the 3' barcode subdomain results in displacement of the newly formed 'UMI' copy and dissociation of the two probes.

In a subsequent step, dGTP (the nucleoside triphosphate lacking from the initial reaction) is added to the reaction buffer. Now, when the newly formed 'UMI' copy (which is identical to the original 'UMI') outcompetes the original 'UMI' sequence for binding to its complementary sequence in the 3' barcode subdomain of the 5' paired domain, the polymerase can continue to extend through the 'C-stopper' molecule (because the reaction buffer now includes a complementary dGTP), displacing the original 'UMI', and copy the 5' primer-binding domain 'PCR primer 2') of the first probe. When the original 'UMI' linked to the original 'PCR primer 2' outcompetes the newly formed copy of the 'UMI' linked to "PCR primer 2' for binding to its complementary sequence on the 5' paired domain, the newly formed copy is displaced. This newly formed copy (an extension of the second probe) can now serve as a template for amplification (e.g., PCR) using a primer that is identical to the 5' unpaired primer-binding domain 'PCR primer 1' and a primer that is complementary to the newly formed copy of the 5' primer-binding domain of the first probe 'PCR primer 2'.

Figure 4:
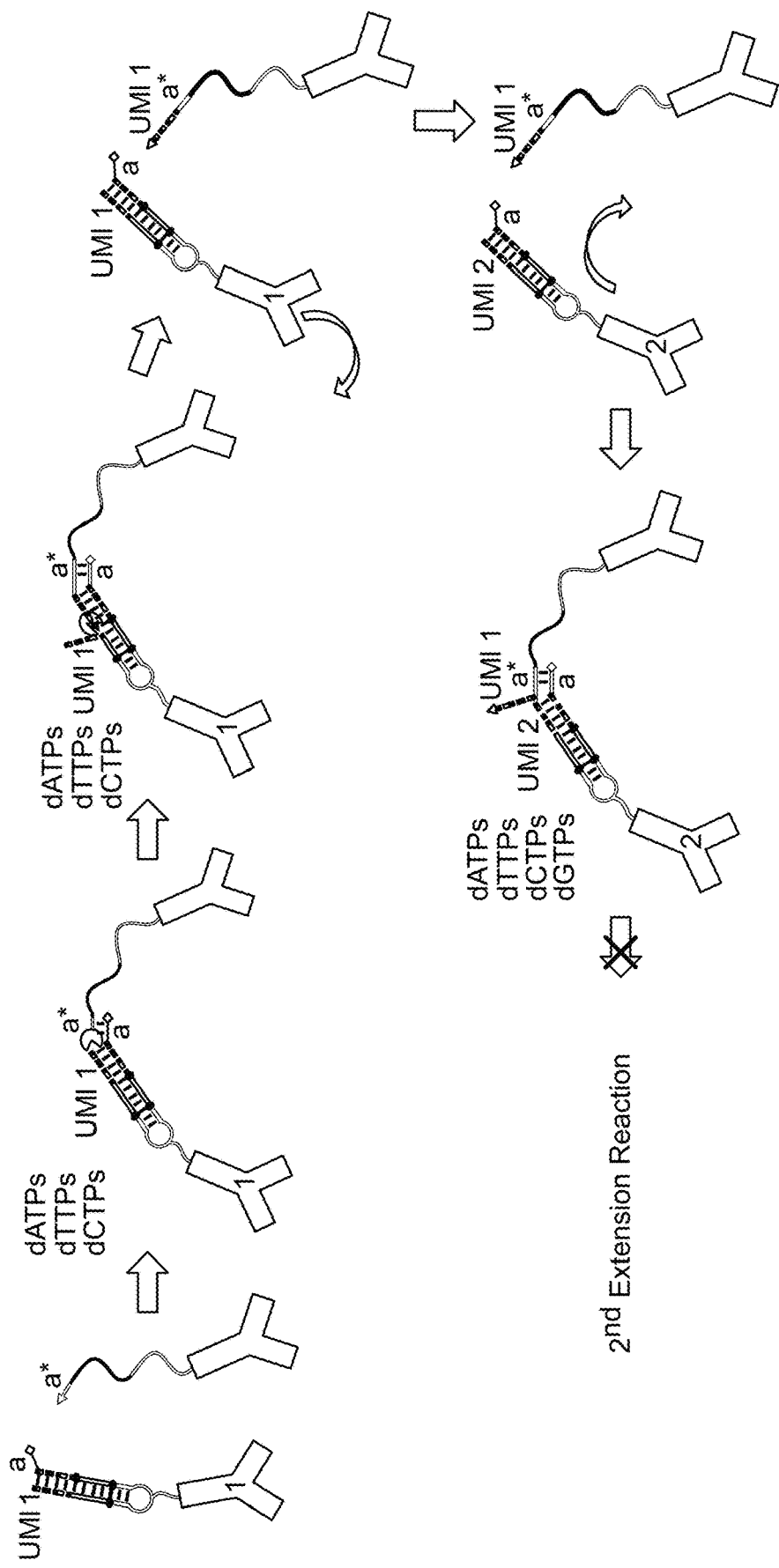
FIG. 4 shows an example of a method of the present disclosure in the absence of a target.

FIG. 4 depicts an example of a reaction mechanism between probes in reaction buffer that does not include the target protein. In the initial reaction, in the absence of dGTP, the 'UMI' of the first probe is copied onto the second probe, in the same manner as described above. This reaction happened regardless of whether the antibodies are bound to the target protein. In the subsequent reaction (where dGTP is now present), however, the nucleic acid record generated will not contain primer-binding site 'PCR primer 2' for an amplification reaction. Instead, when the probe containing the copied 'UMI' sequence binds to another probe containing a different UMI sequence, strand displacement does not occur, because there is no competitive binding. The primer domain of the second probe 'a*' is effectively "stuck" to its complementary domain 'a' of the other probe. Thus, a subsequence amplification reaction will not amplify, anything, indicating that the target protein was not present in the reaction buffer.

Probes

The present disclosure provides pairs of nucleic acid probes, typically used to detect a target molecule (e.g., protein or nucleic acid) of interest. Nucleic acid probes are designed to interact with each other through nucleotide base pairing, in a pre-determined way, such that when co-localized on a target protein, their interaction generates an amplifiable nucleic acid record to reflect that the two particular probes were, indeed, co-localized. Likewise, when two probes interact, and they are not co-localized on a target protein, their interaction generates a non-amplifiable nucleic acid record. Probes are considered part of the same pair if both probes of the pair bind to the same target molecule (e.g., different epitopes of the same target protein). Probes are considered part of different pairs if one probe of the pair binds to a target protein that is different from the target protein bound by the other probe of the pair.

FIG. 2 provides an example of a pair of nucleic acid probes of the present disclosure. A first nucleic acid probe (right image) comprises a (i) 5' paired domain comprising a 5' primer-binding subdomain 'PCR primer 2' linked to a 3' barcode subdomain 'UMI', wherein the 3' barcode subdomain is formed by base pairing between a sequence of nucleotides (e.g., A, C, T) that lacks one of A, T, C or G (e.g., G) and a complementary sequence of nucleotides (e.g., A, G, T), and (ii) a 3' impaired primer-binding domain 'a' A nucleotide (e.g., 'C-stopper'), corresponding to the nucleotide lacking from the 3' barcode subdomain, may be located between the 3' barcode subdomain 'UMI' and the 5' primer-binding subdomain 'PCR primer 2'. The 5' primer-binding subdomain 'PCR primer 2' may comprise a 5' molecule that terminate polymerization 'Stopper' A second nucleic acid probe (left image) comprises a 5' primer-binding domain 'PCR primer 1' linked to a 3' primer domain 'a*' that is complementary to the 3' unpaired primer-binding domain 'a' of the first nucleic acid probe.

One of the nucleic acid probes of a particular pair includes, at its 3' end, a primer. A "primer" is a nucleic acid that serves as a starting point for nucleic acid synthesis. A polymerase adds nucleotides to a primer to generate a new nucleic acid strand. Primers and primer domains of the present disclosure are designed to be complementary to and to bind to primer-binding domains. Thus, primer length and composition (e.g., nucleotide composition) depend, at least in part, on the length and composition of a primer-binding domain. In some embodiments, a primer or a primer domain has a length of 4 to 40 nucleotides. For example, a primer or primer domain may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, a primer or primer domain may have a length of 4 to 10, 4 to 15, 4 to 20, 4 to 25, 4 to 30, 4 to 35, or 4 to 40 nucleotides.

A "domain" refers to a discrete, contiguous sequence of nucleotides or nucleotide base pairs, depending on whether the domain is unpaired (contiguous stretch of nucleotides that are not bound to complementary nucleotides) or paired (contiguous stretch of nucleotide base pairs—nucleotides bound to complementary nucleotides), respectively. In some embodiments, a domain is described as having multiple subdomains for the purpose of defining intramolecular (within the same molecular species) and intermolecular (between two separate molecular species) complementarity. One domain (or one subdomain) is "complementary to" another domain (or another subdomain) if one domain contains nucleotides that base pair (hybridize/bind through Watson-Crick nucleotide base pairing) with nucleotides of the other domain such that the two domains form a paired (double-stranded) or partially-paired molecular species/structure. Complementary domains need not be perfectly (100%) complementary to form a paired structure, although perfect complementarity is provided, in some embodiments. Thus, a primer that is "complementary" to a particular domain binds to that domain, for example, for a time sufficient to initiate polymerization in the presence of polymerase. It should be understood that "domain a," "domain b," "domain c," etc., refer to domains having nucleotide sequences that are different from each other. Thus, a "domain a" has a nucleotide sequence that is different from the nucleotide sequence of a "domain b." It should also be understood that "domain a" and "domain a*" refer to domains having nucleotide sequences that are complementary to each other (either partially or completely complementary) such that the two domains are capable of hybridizing (binding) to each other.

A "primer domain" of a nucleic acid is a sequence of nucleotides that functions as a primer. A primer domain has a complementary intermolecular or intramolecular primer-binding domain. Thus, a "primer-binding domain" of a nucleic acid is a sequence of nucleotides to which a complementary primer binds. A primer-binding domain is typically an unpaired domain, although, it should be understood that a primer-binding domain, in some instances, may include an unpaired subdomain adjacent to a paired subdomain. For example, with reference to FIG. 2, the exposed unpaired domain "a" sticking out from the nucleic acid strand is considered to be a primer-binding domain. In some embodiments, a primer-binding domain has a length of 4 to 40 nucleotides (or nucleotide base pairs, or a combination of nucleotides and nucleotide base pairs, depending the unpaired and/or paired nature of the primer-binding domain). For example, a primer-binding domain may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides (and/or nucleotide base pairs). In some embodiments, a primer-binding domain may have a length of 4 to 10, 4 to 15, 4 to 20, 4 to 25, 4 to 30, 4 to 35, or 4 to 40 nucleotides (and/or nucleotide base pairs). In some embodiments, a primer-binding domain is longer than 40 nucleotides. For example, a primer-binding domain mas have a length of 4 to 100 nucleotides. In some embodiments, a primer-binding domain has a length of 4 to 90, 4 to 80, 4 to 70, 4 to 60, or 4 to 50 nucleotides. In some embodiments, a primer-binding domain is designed to accommodate binding of more than one (e.g., 2 or 3 different) primer.

Domains or other discrete nucleotide sequences are considered "adjacent" to each other if they are contiguous with each other (there are no nucleotides separating the two domains), or if they are within 50 nucleotides (e.g., 1-50, 1-40, 1-30, 1-20, 1-10, 1-5) of each other. That is, in some embodiments, two domains may be considered adjacent if the two domains are separated from each other by 1, 2, 3, 4, 5, 6, 7, 8, 9, 10, 11, 12, 13, 14, 15, 16, 17, 18, 19, 20, 25, 30, 35, 40, 45 or 50 nucleotides.

Nucleotide domains and subdomains are described in terms of a 3' and/or 5' position relative to one another, or relative to the entire length of a probe. For example, with reference to FIG. 2, as an example, the hairpin structure shown on the left includes a 5' paired domain and a 3' unpaired domain. The 3' unpaired domain is labeled 'a', and the 5' paired domain includes the terminal loop structure, the 'PCR primer 2' subdomain and the 'UMI' subdomain, and a 3' unpaired domain 'a' Within the context of the whole 5' paired domain, the 'PCR primer 2' subdomain is considered a 5' primer-binding domain, and the 'UMI' subdomain is considered the 3' barcode domain (the 'PCR primer 2' domain is located 5' from the 'UMI' barcode domain). Similarly, single-stranded nucleic acid structure on the right includes a 5' unpaired primer-binding domain and a 3' unpaired primer domain.

In some embodiments, a probe forms a hairpin structure, which is a stretch of contiguous nucleotides that folds through intramolecular base pairing to form a paired domain flanked by a unpaired linear domain and an unpaired loop domain, as shown, for example, in FIG. 2 (left image). While "hairpin" primers, generally containing a loop domain, are depicted in the figures, it should be understood that any hairpin primer mas be substituted with any nucleic acid duplex that includes a 3' unpaired domain (to serve as a primer) and an adjacent 5' paired domain.

An "unpaired domain" of a probe refers to a sequence of nucleotides that is not bound to a complementary sequence of nucleotides. Single-stranded nucleic acids, for example, are considered "unpaired" nucleic acids. One of the probes of a pair of nucleic acid probes generally includes a 3' unpaired primer domain that is complementary to (and binds to) a primer-binding domain of the other probe of the pair. The length of a 3' unpaired primer domain (or primer-binding domain) may vary. In some embodiments, a 3' unpaired primer domain has a length of 5-40 nucleotides. For example, a 3' unpaired primer domain (or primer-binding domain) may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a 3' unpaired primer domain (or primer-binding domain) has a length of 5, 10, 15, 20, 25, 30, 35 or 40 nucleotides. In some embodiments, a 3' unpaired primer domain (or primer-binding domain) has a length of 10, 11, 12, 13, 14, 15, 16, 17, 18, 19, 20, 21, 22, 23, 24 or 25 nucleotides. A 3' unpaired primer domain (or primer-binding domain), in some embodiments, is longer than 40 nucleotides, or shorter than 5 nucleotides.

A "paired domain" of a probe refers to a sequence of nucleotides bound to a complementary sequence of nucleotides (e.g., Watson-Crick nucleobase pairing). Double-stranded nucleic acids, for example, are considered "paired" nucleic acids. A paired domain of a probe is typically located 5' from (and, in some embodiments, directly adjacent to) a 3' unpaired primer-binding domain. The paired domain of hairpin probe is formed by intramolecular base pairing (base pairing between nucleotides within the same molecule) of a single-stranded nucleic acid. The length of a paired domain mas vary. In some embodiments, a paired domain (or subdomain within the paired domain) has a length of 5-40 nucleotides. For example, a paired domain (or subdomain within the paired domain) may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain (or subdomain within the paired domain) has a length of 5, 10, 15, 20, 25, 30, 35 or 40 nucleotides. In some embodiments, a paired domain (or subdomain within the paired domain) has a length of 10, 11, 12, 13, 14, 15, 16, 17, 18, 19, 20, 21, 22, 23, 24 or 25 nucleotides. A paired domain (or subdomain within the paired domain), in some embodiments, is longer than 40 nucleotides, or shorter than 5 nucleotides.

In some embodiments, a 5' paired domain has subdomains (e.g. two subdomains), as depicted, for example, in FIG. 2 (see. e.g., where subdomain PCR primer 2' is adjacent to and located 5' from subdomain "UMI"). In some embodiments, a probe may contain two or more 5' paired domains that are identical to each other (have identical nucleotide sequences). For example, nucleic acid probes depicted in FIGS. 11-13 include a first subdomain "UMI" and a second subdomain "UMI".

A "loop domain" of a hairpin probe refers to an unpaired domain that form a loop-like structure at the end (adjacent to) a 5' paired domain. That is, a loop domain links complementary domains of a nucleic acid to form a 5' paired domain. The length of a loop domain may vary. In some embodiments, a loop domain has a length of 3 to 50 nucleotides. For example, a loop domain may have a length of 3, 4, 5, 6, 7, 8, 9 or 10 nucleotides. In some embodiments, a loop domain has a length of 3-10, 3-15, 32-10, 3-25, 3-30, 3-35, 3-40, 3-35, 3-40, 3-45, 3-50, 4-10, 4-15, 4-10, 4-25, 4-30, 4-35, 4-40, 4-35, 4-40, 4-45 or 4-50 nucleotides. In some embodiments, a loop domain is longer than 50 nucleotides.

A "barcode" domain or subdomain is a sequence of nucleotides that uniquely identifies a particular molecule. Barcodes may also be referred to in the art as "unique molecular identifiers" (UMIs). UMIs associate distinct sequences with a nucleic acid molecule and can be used to uniquely identify an amplified nucleic acid molecule. A barcode domain typically contains a nucleotide sequence that contains only three of the four nucleotides. For example, a barcode domain or subdomain may include (a) only As, Ts, and Cs, (b) only As, Ts, and Gs, (c) only Gs, Ts, and Cs, or (d) only As, Gs, and Cs. Thus, a barcode domain or subdomain may lack (may not include) one of A, T, C or G. The length of a barcode domain or subdomain may vary. In some embodiments, a barcode domain or subdomain has a length of 3 to 50, or 3-200 nucleotides. For example, a barcode domain or subdomain may have a length of 3, 4, 5, 6, 7, 8, 9, 10, 11, 12, 13, 14, 15, 16, 17, 18, 19 or 20 nucleotides. In some embodiments, a barcode domain or subdomain has a length of 3-10, 3-15, 32-10, 3-25, 3-30, 3-35, 3-40, 3-35, 3-40, 3-45, 3-50, 4-10, 4-15, 4-10, 4-25, 4-30, 4-35, 4-40, 4-35, 4-40, 4-45 or 4-50 nucleotides. In some embodiments, a barcode domain or subdomain is longer than 50 nucleotides. In some embodiments, a barcode domain or subdomain has a length of 5-10, 5-20, 5-30, 5-40, 5-50, 5-60, 5-70, 5-80, 5-90, or 5-100 nucleotides.

A nucleic acid probe may have a domain that is considered "unique" or "specific" to a target if the domain is associated only with that target and can be used to identify only that target molecule among a population of target molecules, including other targets with their own unique probes. In some embodiments, a nucleic acid probe comprises a primer-binding domain that is unique. In some embodiments, the nucleic acid probe comprises a barcode subdomain that is unique.

One of the probes of a pair of nucleic acid probes of the present disclosure typically includes at least one molecule or modification that terminates polymerization (represented in FIGS. 2-6, 8, and 10-15 as black dots). A molecule or modification that terminates polymerization (referred to as a "stopper") is typically located at the 5' end of a paired domain, separating the paired domain from a terminal loop domain. In this configuration, the stopper is capable of preventing a strand displacing polymerase from extending through the loop domain. In some embodiments, the molecule that terminates polymerization is one or more natural nucleotides. In some embodiments, stopper may comprise one or more A, T, C, or G nucleotides. For example, the "C-stopper" in the 3' barcode subdomain of the first nucleic acid probe in FIG. 2 comprises at least one C nucleotide that can terminate polymerization in a reaction buffer in the absence of dGTPs. In some embodiments, a stopper is at least one C nucleotide. In some embodiments, a stopper is at least one G nucleotide. In some embodiments, a stopper is at least one A nucleotide. In some embodiments, a stopper is at least one T nucleotide.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with iso-dG but not with dG. Similarly, iso-dG will base pair with iso-dC but not with dC. By incorporating these nucleotides in a pair on opposite sides of the hairpin, at the stopper position, the polymerase will be halted, as it does not have a complementary nucleotide in solution to add at that position.

In some embodiments, RNA bases and/or methylated RNA bases may be used as stop sequences within a hairpin primer. For example, 2'-o-methylated RNA may be used as a molecule that terminates polymerization.

In some embodiments, the molecule that terminates polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3h (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

Inclusion of a molecule or modification that terminates polymerization often creates a "bulge" in an unpaired domain of hairpin primer, because the molecule or modification is not paired. Thus, in some embodiments, hairpin primers are designed to include, opposite the molecule or modification, a single nucleotide (e.g., thymine), at least two of same nucleotide (e.g., a thymine dimer (TT) or trimer (TTT)), or an non-natural modification.

In some embodiments, the efficiency of performance of a "stopper" molecule or modification is improved by lowering dNTP concentrations (e.g., from 200 µM) in a reaction to 100 µM, 10 µM, 1 µM, or less.

Figure 8:
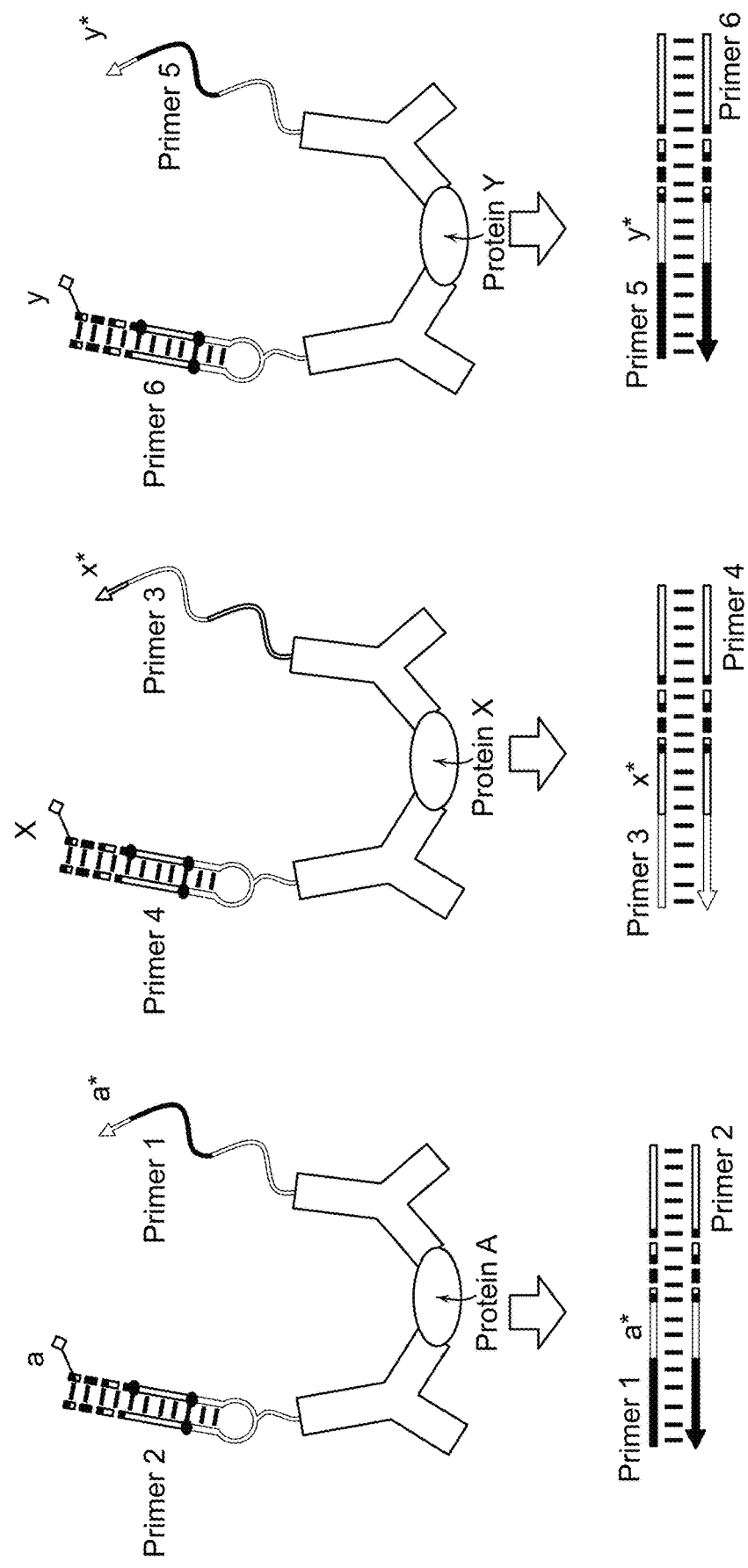
FIG. 8 shows an example of multiple target detection.

The end product of a target detection reaction of the present disclosure, in some embodiments (e.g., in the present of a target molecule), is an amplifiable (can be amplified by, for example, PCR) nucleic acid record that includes at least one barcode flanked by primer binding domains, one primer-binding domain appended from one of the probes of a nucleic acid probe pair, and the other primer-binding domain appended from the other of the probes of the pair. Examples of such amplifiable nucleic acid records are depicted in FIG. 8. Nucleic acids of the present disclosure may comprise DNA, RNA or a combination of DNA and RNA. The nucleic acids may be single-stranded, double-stranded or partially double-stranded (contain at least one single-stranded domain and at least one double-stranded domain).

FIG. 10 provides another example of a pair of nucleic acid probes of the present disclosure. A first nucleic acid probe comprises (i) a 5' paired domain comprising a 5' primer-binding subdomain 'PCR primer 2' linked to a 3' barcode subdomain 'UMI' The 3' barcode subdomain 'UMI' is formed by base pairing between a sequence of nucleotides (e.g., A, T, C) that lacks one of A, T, C or G (e.g., G) and a complementary sequence of nucleotides (e.g., A, G, T) and (ii) a 3' unpaired primer-binding domain 'a'. A nucleotide corresponding to the nucleotide lacking from the 3' barcode subdomain ('C-stopper') is located between the 3' barcode subdomain ('UMI') and the 5' primer-binding subdomain 'a'. A second nucleic acid probe comprises a 5' primer-binding domain 'PCR primer 1' linked to a 3' primer domain 'a*' that is complementary to the 3' unpaired primer-binding domain 'a' of the first nucleic acid probe.

FIG. 11 provides yet another example of a pair of nucleic acid probes of the present disclosure. A first nucleic acid probe comprises (i) a 5' paired domain comprising a barcode 'UMI' formed by base pairing between a unique sequence of nucleotides and a complementary sequence of nucleotides, and a 5' molecule 'Stopper' that terminates polymerization, and (ii) a 3' unpaired primer-binding domain that comprises a central primer-binding subdomain 'PCR primer 2' flanked by a 5' primer-binding subdomain 'a' and a barcode subdomain 'UMI' that lacks one of A, T, C or G (wherein the UMI of (i) and the UMI of (ii) share the same nucleotide sequence) A molecule that terminates polymerization 'Stopper' is located between the 5' primer-binding subdomain 'a' of the 3' unpaired domain and the central primer-binding subdomain 'PCR primer 2'. A second nucleic acid probe comprises a 5' primer-binding domain 'PCR primer 1' linked to a 3' primer domain 'a*' that is complementary to the 5' primer-binding subdomain 'a' of the 3' unpaired primer-binding domain of the first nucleic acid probe.

FIG. 12 provides still another example of a pair of nucleic acid probes of the present disclosure. A first nucleic acid probe that comprises (i) a 5' paired domain comprising a barcode 'UMI' formed by base pairing between a unique sequence of nucleotides and a complementary sequence of nucleotides, and a 5' molecule (black dot) that terminates polymerization, (ii) a central unpaired primer-binding domain 'a', and (iii) a 3' paired domain that comprises a 5' paired subdomain 'PCR primer 2' and a 3' paired barcode subdomain 'UMI' formed by base pairing between a sequence of nucleotides that lacks one of A, T, C or G and a complementary sequence of nucleotides (wherein the UMI of (i) and the UMI of (iii) share the same nucleotide sequence), and a 5' molecule (black dot) that terminates polymerization. A second nucleic acid probe comprises a 5' primer-binding domain 'PCR primer 1' linked to a 3' primer domain 'a*' that is complementary to the 5' primer-binding subdomain 'a' of the 3' unpaired primer-binding domain of the first nucleic acid probe.

FIG. 13 provides another example of a pair of nucleic acid probes of the present disclosure. A first nucleic acid probe comprises (i) a5' paired domain comprising a barcode 'UMI' formed by base pairing between a sequence of nucleotides that lacks one of A, T, C or G and a complementary sequence of nucleotides, wherein the 5' paired domain 'UMI' is flanked by a 5' molecule (black dot) that terminates polymerization and a 3' unpaired primer domain 'a', (ii) a central unpaired domain, and (iii) a 3' paired domain that comprises a 3' paired barcode subdomain UMI formed by base pairing between a unique sequence of nucleotides and a complementary sequence of nucleotides (wherein the UMI of (i) and the UMI of (iii) share the same nucleotide sequence), and 5' paired subdomain 'PCR primer 2'. A second nucleic acid probe comprises a 5' primer-binding domain 'PCR primer 1' linked to a 3' primer domain 'a*' that is complementary to the 5' primer-binding subdomain 'a' of the 3' unpaired primer-binding domain of the first nucleic acid probe.

Figure 5:
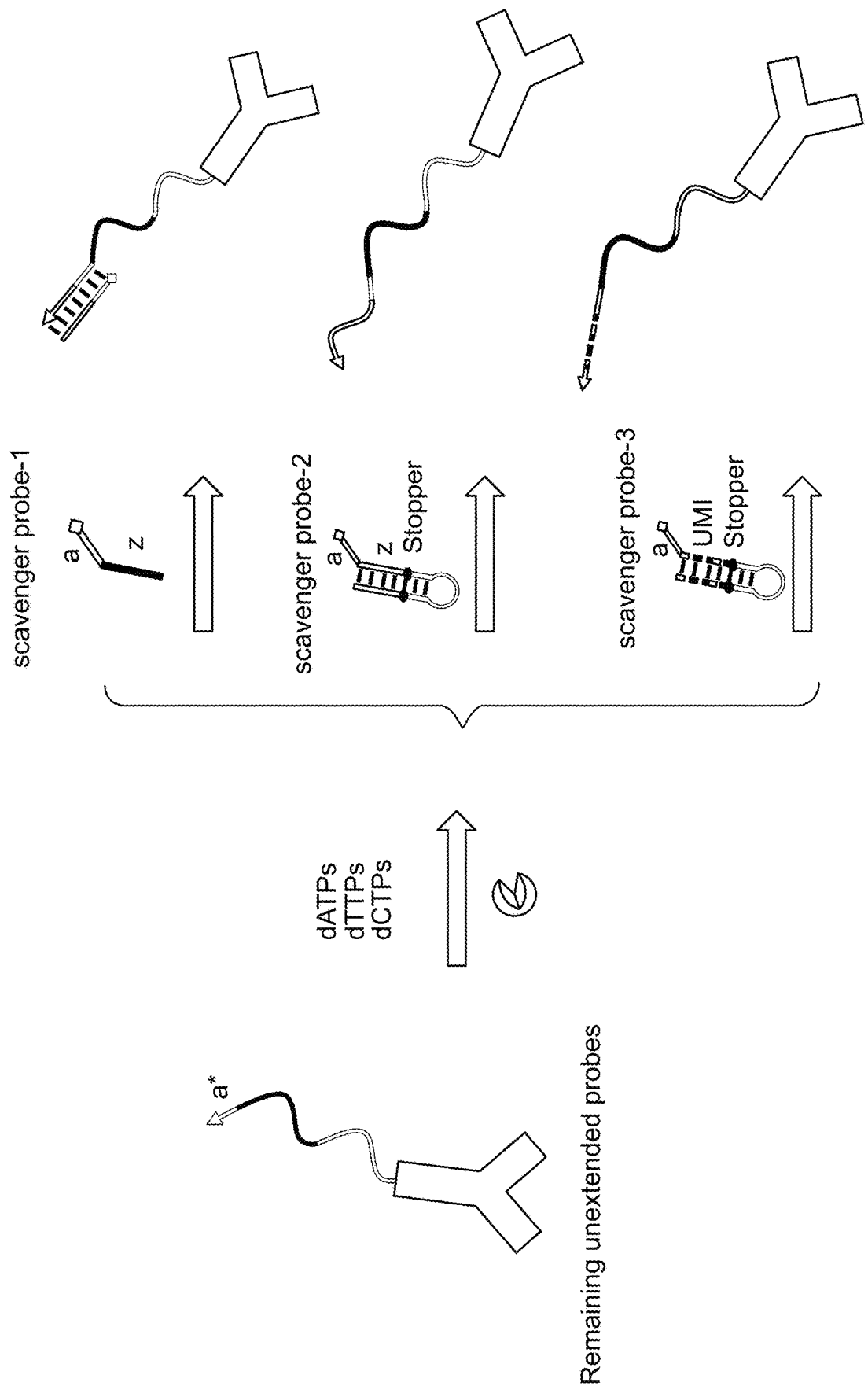
FIG. 5 shows examples of scavenger probes.

Various nucleic acid scavenger probes can be used in the disclosed method to extend a nucleic acid probe without appending a PCR primer-binding domain. Examples of nucleic acid scavenger probes are shown in FIG. 5. In some embodiments, the scavenger probe is a nucleic acid sequence comprising a 5' unpaired domain ("z" domain) and a 3' unpaired primer-binding domain ("a" domain), for example see scavenger probe-1 in FIG. 5. In some embodiments, the scavenger probe is a nucleic acid hairpin comprising a 5' paired domain ("z" domain), a 3' unpaired (toehold) primer-binding domain ("a" domain), and a "stopper" molecule, for example see scavenger probe-2 in FIG. 5. In some embodiments, the scavenger probe is a nucleic acid hairpin comprising a 5' paired barcode domain ("UMI" domain), a 3' unpaired (toehold) primer-binding domain ("a" domain), and a "stopper" molecule, for example see scavenger probe-3 in FIG. 5.

Provided herein, in some embodiments, are pairs of nucleic acid probes. Such pairs of nucleic acid probes are intended to be used in combination with each other to detect a target. Provided herein, in some embodiments, are pluralities of nucleic acid probes. A "plurality" comprises at least two nucleic acid probes. In some embodiments, a plurality comprises 2 to 2 million nucleic acid probes (e.g., unique probes). For example, a plurality may comprise 100, 500, 1000, 5000, 10000, 100000, 1000000, or more, nucleic acid probes. The present disclosure is not limited in this aspect.

Nucleic acid probes, as provided herein, may be linked to (labeled with) a detectable molecule (e.g., a molecule that emits a detectable signal, such as a fluorescent or chemiluminescent signal). In some embodiments, the label is a fluorophore. A primer linked to a fluorophore or other fluorescent/chemiluminescent molecule is referred to simply as a "fluorescent primer." Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE). Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorophores and molecules that emit a detectable signal are encompassed by the present disclosure.

Figure 28:
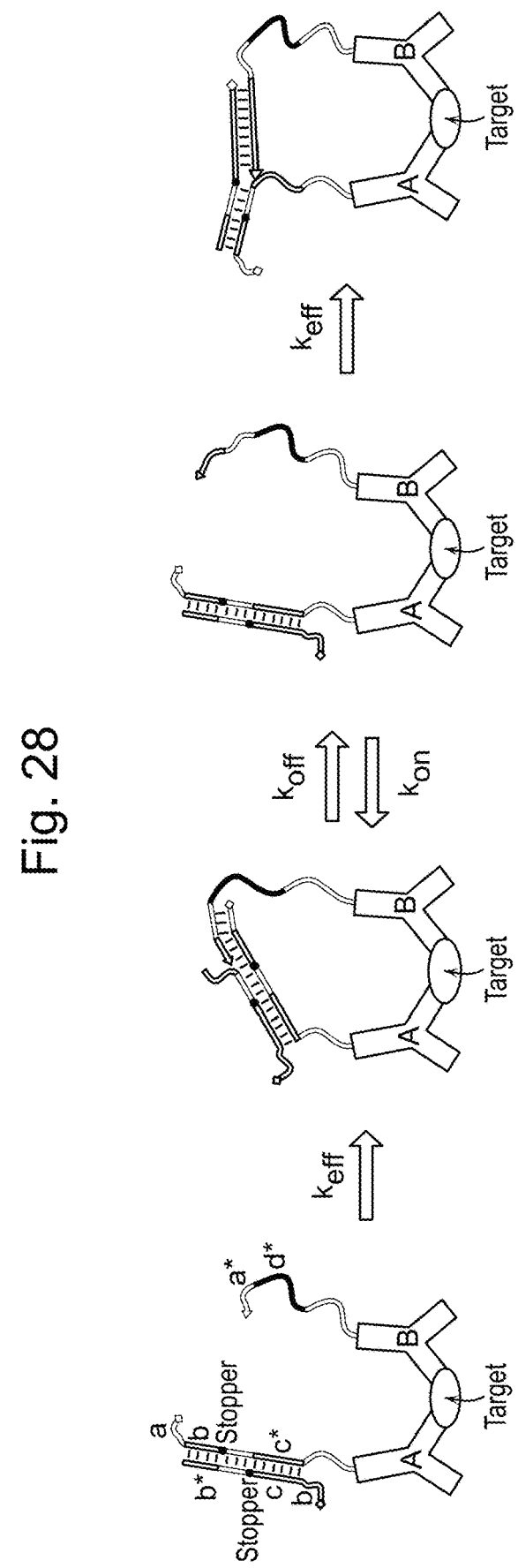
FIG. 28 shows an example of a successive proximity extension and expedited dissociation (SPEED) reaction using a probe with two toehold domains and two stopper molecules.
Figure 29:
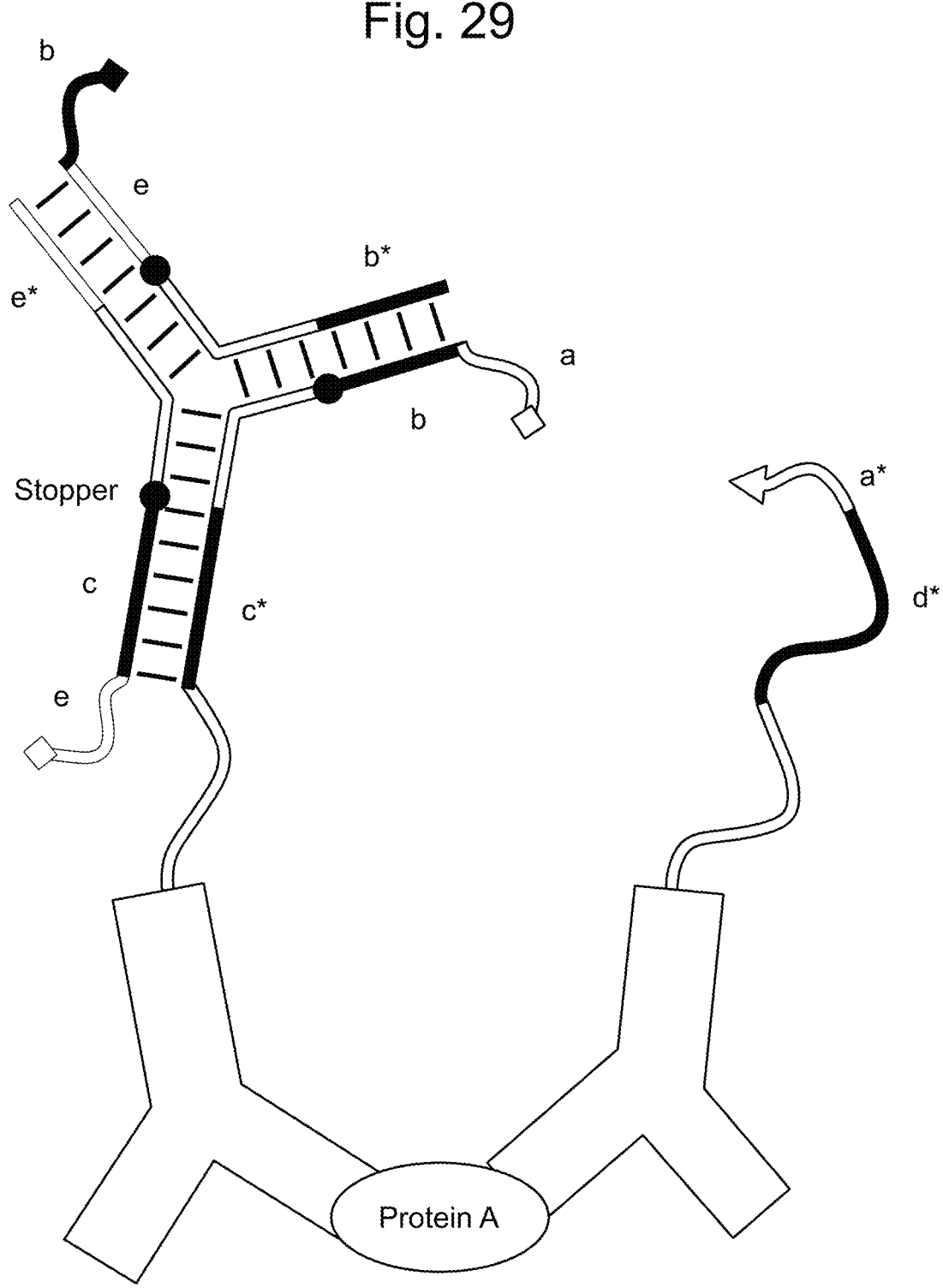
FIG. 29 shows another example of a successive proximity extension and expedited dissociation (SPEED) reaction using a probe with three toehold domains and three stopper molecules.
Figure 35:
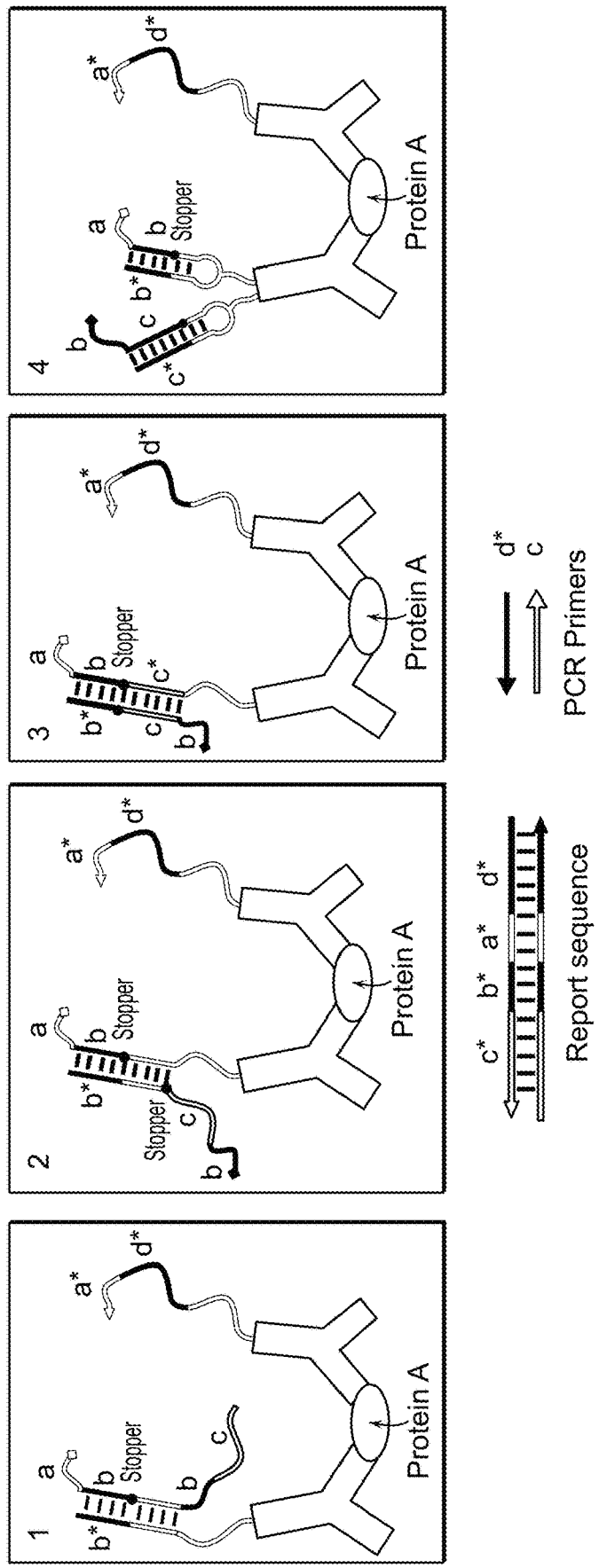
FIG. 35 shows schematics of four different SPEED probe configurations, each of which produce the same reporter sequence.

Additional examples of probe pairs are shown in FIGS. 28, 29 and 35.

Target-Binding Molecules

Nucleic acid probes of the present disclosure typically bind to a target through a target-binding molecule. In some embodiments, the target-binding molecule is attached to the 5' end of the probe (e.g., the end distal to the primer-binding region). In some embodiments, the target-binding molecule is attached to the single-stranded loop region of a probe arranged in the form of a hairpin (see. e.g., FIG. 2).

A probe, as provided herein, may be linked to (labeled with) a molecule that binds specifically to a target (e.g., a molecule that binds a protein, such as an antibody, see FIG. 2). Binding molecules may be, without limitation, amino acid based or nucleic acid based. An example of amino acid based binding molecules are antibodies and antigen-binding antibody fragments. The antibodies and fragments may be monoclonal antibodies. An example of a nucleic acid based binding molecule is an aptamer.

Examples of target-binding molecules for use as provided herein include, without limitation, biotin, antibodies, aptamers, nanobodies, nucleic acids, drugs (e.g., small molecule drugs) and atoms (e.g., Li). Other targeting-binding molecules are contemplated. In some embodiments, a targeting-binding molecule may be attached to a probe through hybridization or "click chemistry". See, e.g., Kolb H. C., et al. Angewandte Chemie International Edition 2001, 40 (11): 2004-2021; and Evans R. A. Australian Journal of Chemistry, 2007, 60 (6):384-395.

As used herein, "antibody" includes full-length antibodies and any antigen binding fragment (e.g., "antigen-binding portion") or single chain thereof. The term "antibody" includes, without limitation, a glycoprotein comprising at least two heavy (H) chains and two light (L) chains interconnected by disulfide bonds, or an antigen binding portion thereof. Antibodies may be polyclonal or monoclonal, xenogeneic, allogeneic, or syngeneic; or modified forms thereof (e.g., humanized, chimeric).

As used herein, "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the VH, VL, CL and CH1 domains; (ii) a F(ab')2 fragment, a bivalent fragment comprising two Fab fragments linked by a disulfide bridge at the hinge region. (iii) a Fd fragment consisting of the VH and CH1 domains; (iv) a Fv fragment consisting of the VH and VL domains of a single arm of an antibody. (v) a dAb fragment (Ward et al., Nature 341:544 546, 1989), which consists of a VH domain, and (vi) an isolated complementarity determining region (CDR) or (vii) a combination of two or more isolated CDRs, which may optionally be joined by a synthetic linker. Furthermore, although the two domains of the Fv fragment, VH and VL, are coded for by separate genes, they can be joined, using recombinant methods, by a synthetic linker that enables them to be made as a single protein chain in which the VH and VL regions pair to form monovalent molecules (known as single chain Fv (scFv); see, e.g., Bird et al. Science 242 423 426, 1988, and Huston et al. Proc. Natl. Acad Sci. USA 85.5879-5883, 1988). Such single chain antibodies are also encompassed within the term "antigen-binding portion" of an antibody. These antibody fragments are obtained using conventional techniques known to those with skill in the art, and the fragments are screened for utility in the same manner as are intact antibodies.

As used herein, "nucleic acid aptamer" refers to a small RNA or DNA molecules that can form secondary and tertiary structures capable of specifically binding proteins or other cellular targets (see, e.g., Ni X, et al. Curr Med Chem. 18(27); 4206-4214, 2011).

In some embodiments, it may be preferable to label the pair of nucleic acid probes with molecules that bind distinct epitopes on the target protein. For example, the first probe may be conjugated to a molecule that binds specifically to a first epitope on a target protein, and the second probe may be conjugated to a molecule that binds specifically to a second epitope on the target protein.

Targets

Virtually any target of interest may be detected using the disclosed methods provided that a suitable binding molecule exists. The examples included in the disclosure depicting detection of a protein target are for the purpose of illustration and are not intended to limit the scope of the invention.

Examples of targets include, without limitation, proteins, saccharides (e.g., polysaccharides), lipids, nucleic acids (e.g., DNA, RNA, microRNAs), and small molecules. Targets may be DNA or RNA. In some embodiments, targets are RNA interference molecules, such as short-interfering RNAs (siRNAs) or micro RNAs (microRNAs). In some embodiments, targets are antisense molecules, such as DNA antisense synthetic oligonucleotides (ASOs).

In some embodiments, a molecular target is a biomolecule. As used herein, a "biomolecule" is any molecule that is produced by a having organism, including large macromolecules such as proteins, polysaccharides, lipids and nucleic acids (e.g., DNA and RNA such as mRNA), as well as small molecules such as primary metabolites, secondary metabolites, and natural products. Examples of molecular targets, specifically biomolecules, include, without limitation. DNA. RNA. cDNA, or the DNA product of RNA subjected to reverse transcription, A23187 (Calcimycin, Calcium Ionophore), Abamectine, Abietic acid, Acetic acid, Acetylcholine, Actin, Actinomycin D, Adenosine, Adenosine diphosphate (ADP), Adenosine monophosphate (AMP), Adenosine triphosphate (ATP), Adenylate cyclase, Adonitol, Adrenaline, epinephrine, Adrenocorticotropic hormone (ACTH), Aequorin, Aflatoxin, Agar, Alamethicin, Alanine, Albumins, Aldosterone, Aleurone, Alphaamanitin, Allantoin, Allethrin, α-Amanatin, Amino acid, Amylase, Anabolic steroid, Anethole, Angiotensinogen, Anisomycin, Antidiuretic hormone (ADH), Arabinose, Arginine, Ascomycin, Ascorbic acid (vitamin C), Asparagine, Aspartic acid, Asymmetric dimethylarginine, Atrial-natriuretic peptide (ANP), Auxin, Avidin, Azadirachtin A $C_{35}H_{44}O_{16}$, Bacteriocin, Beauvericin, Bicuculline, Bilirubin, Biopolymer, Biotin (Vitamin H), Brefeldin A, Brassinolide, Brucine, Cadaverine, Caffeine, Calciferol (Vitamin D), Calcitonin, Calmodulin, Calmodulin, Calreticulin, Camphor—($C_{10}H_{16}O$), Cannabinol, Capsaicin, Carbohydrase, Carbohydrate, Carnitine, Carrageenan, Casein, Caspase, Cellulase, Cellulose—($C_6H_{10}O_5$), Cerulenin, Cetrimonium bromide (Cetrimide)—$C_{19}H_{42}BrN$, Chelerythrine, Chromomycin A3, Chaparonin, Chitin, -Chloralose, Chlorophyll, Cholecystokinin (CCK), Cholesterol, Choline, Chondroitin sulfate, Cinnamaldehyde, Citral, Citric acid, Citrinin, Citronellal, Citronellol, Citrulline, Cobalamin (vitamin B12), Coenzyme, Coenzyme Q, Colchicine, Collagen, Coniine, Corticosteroid, Corticosterone, Corticotropin releasing hormone (CRH), Cortisol, Creatine, Creatine kinase, Crystallin, α-Cyclodextrin, Cyclodextrin glycosyltransferase, Cyclopamine, Cyclopiazonic acid, Cysteine, Cystine, Cytidine, Cytochalasin, Cytochalasin E, Cytochrome, Cytochrome C, Cytochrome c oxidase, Cytochrome c peroxidase, Cytokine, Cytosine—$C_4H_5N_3O$, Deoxycholic acid, DON (DeoxyNivalenol), Deoxyribofuranose, Deoxyribose, Deoxyribose nucleic acid (DNA), Dextran, Dextrin, DNA, Dopamine, Enzyme, Ephedrine, Epinephrine—$C_9H_{13}NO_3$, Erucic acid—CH3(CH2)7CH═CH(CH2)11COOH, Erythritol, Erythropoietin (EPO), Estradiol, Eugenol, Fatty acid, Fibrin, Fibronectin, Folic acid (Vitamin M), Follicle stimulating hormone (FSH), Formaldehyde, Formic acid, Formnoci, Fructose, Fumonisin B1, Gamma globulin, Galactose, Gamma globulin, Gamma-aminobutyric acid, Gamma-butyrolactone, Gamma-hydroxybutyrate (GHB), Gastrin, Gelatin, Geraniol, Globulin, Glucagon, Glucosamine, Glucose—C6H12O6, Glucose oxidase, Gluten, Glutamic acid, Glutamine, Glutathione, Gluten, Glycerin (glycerol), Glycine, Glycogen, Glycolic acid, Glycoprotein (e.g., glycoprotein enzymes such as prostate-specific antigen (PSA)), Gonadotropin-releasing hormone (GnRH), Granzyme, Green fluorescent protein, Growth hormone, Growth hormone releasing hormone (GHRH), GTPase, Guanine, Guanosine, Guanosine triphosphate (+GTP), Haptoglobin, Hematoxylin, Heme, Hemerythrin, Hemocyanin, Hemoglobin, Hemoprotein, Heparan sulfate, High density lipoprotein, HDL, Histamine, Histidine, Histone, Histone methyltransferase, HLA antigen, Homocystine, Hormone, human chorionic gonadotropin (hCG), Human growth hormone, Hyaluronate, Hyaluronidase, Hydrogen peroxide, 5-Hydroxymethylcytosine, Hydroxyproline, 5-Hydroxytryptamine, Indigo dye, Indole, Inosine, Inositol, insulin, Insulin-like growth factor, Integral membrane protein, Integrase, Integrin, Intein, Interferon, Inulin, Ionomycin, Ionone, Isoleucine, Iron-sulfur cluster, K252a, K252b, KT5720, KT5823, Keratin, Kinase, Lactase, Lactic acid, Lactose, Lanolin, Lauric acid, Leptin, Leptomycin B, Leucine, Lignin, Limonene, Linalool, Linoleic acid, Linolenic acid, Lipase, Lipid, Lipid anchored protein, Lipoamide, Lipoprotein, Low density lipoprotein, LDL, Luteinizing hormone (LH), Lycopene, Lysine, Lysozyme, Malic acid, Maltose, Melatonin, Membrane protein, Metalloprotein, Metallothionein, Methionine, Mimosine, Mithramycin A, Mitomycin C, Monomer, Mycophenolic acid, Myoglobin, Myosin, Natural phenols, Nucleic Acid, Ochratoxin A, Oestrogens, Oligopeptide, Oligomycin, Orcin, Orexin, Omithine, Oxalic acid, Oxidase, Oxytocin, p53, PABA, Paclitaxel, Palmitic acid, Pantothenic acid (vitamin B5), parathyroid hormone (PTH), Paraprotein, Pardaxin, Parthenolide, Patulin, Paxilline, Penicillic acid, Penicillin, Penitrem A, Peptidase, Pepsin, Peptide, Perimycin, Peripheral membrane protein, Perosamine, Phenethylamine, Phenylalanine, Phosphagen, phosphatase, Phospholipid, Phenylalanine, Phytic acid, Plant hormones, Polypeptide, Polyphenols, Polysaccharides, Porphrin, Prion, Progesterone, Prolactin (PRL), Proline, Propionic acid, Protamine, Protease, Protein, Proteinoid, Putrescine, Pyrethrin, Pyridoxine or pyridoxamine (Vitamin B6), Pyrrolysine, Pyruvic acid, Quinone, Radicicol, Raffinose, Renin, Retinene, Retinol (Vitamin A), Rhodopsin (visual purple), Riboflavin (vitamin 1B2), Ribofuranose, Ribose, Ribozyme, Ricin, RNA—Ribonucleic acid, RuBisCO, Safrole, Salicylaldehyde, Salicylic acid, Salvinorin A—C23H28O8, Saponin, Secretin, Selenocysteine, Selenomethionine, Selenoprotein, Serine, Serine kinase, Serotonin, Skatole, Signal recognition particle, Somatostatin, Sorbic acid, Squalene, Staurosporin, Stearic acid, Sterigmatocystin, Sterol, Strychnine, Sucrose (sugar), Sugars (in general), superoxide, tau protein, T2 Toxin, Tannic acid, Tannin, Tartaric acid, Taurine, Tetrodotoxin, Thaumatin, Topoisomerase, Tyrosine kinase, Taurine, Testosterone, Tetrahydrocannabinol (THC), Tetrodotoxin, Thapsigargin, Thaumatin, Thiamine (vitamin B1)—C12H17CN4OS·HCl, Threonine, Thrombopoietin, Thymidine, Thymine, Triacsin C, Thyroid-stimulating hormone (TSH), Thyrotropin-releasing hormone (TRH), Thyroxine (T4), Tocopherol (Vitamin E), Topoisomerase, Triiodothyronine (T3), Transmembrane receptor, Trichostatin A, Trophic hormone, Trypsin, Tryptophan, Tubulin, Tunicamycin, Tyrosine, Ubiquitin, Uracil, Urea, Urease, Uric acid—C5H4N4O3, Uridine, Valine, Valinomycin, Vanabins, Vasopressin, Verruculogen, Vitamins (in general), Vitamin A (retinol), Vitamin B, Vitamin B1 (thiamine), Vitamin B2 (riboflavin), Vitamin B3 (niacin or nicotinic acid), Vitamin B4 (adenine), Vitamin 85 (pantothenic acid), Vitamin B6 (pyridoxine or pyridoxamine), Vitamin B12 (cobalamin), Vitamin C (ascorbic acid), Vitamin D (calciferol), Vitamin E (tocopherol), Vitamin F, Vitamin H (biotin), Vitamin K (naphthoquinone), Vitamin M (folic acid), Wortmannin and Xylose.

In some embodiments, a molecular target is a protein target such as, for example, proteins of a cellular environment (e.g. intracellular or membrane proteins). Examples of proteins include, without limitation, fibrous proteins such as cytoskeletal proteins (e.g., actin, arp2/3, coronin, dystrophin, FtsZ, keratin, myosin, nebulin, specton, tau, titin, tropomyosin, tubulin and collagen) and extracellular matrix proteins (e.g., collagen, elastin, f-spondin, pikachurin, and fibronectin); globular proteins such as plasma proteins (e.g., serum amyloid P component and serum albumin), coagulation factors (e.g., complement proteins, C1-inhibitor and C3-convertase, Factor VIII, Factor XIII, fibrin, Protein C, Protein S, Protein Z, Protein Z-related protease inhibitor, thrombin, Von Willebrand Factor) and acute phase proteins such as C-reactive protein; hemoproteins, cell adhesion proteins (e.g. cadherin, ependymin, integrin, Ncam and selectin); transmembrane transport proteins (e.g., CFTR, glycophorin D and scramblase) such as ion channels (e.g., ligand-gated ion channels such nicotinic acetylcholine receptors and GABAa receptors, and voltage-gated ion channels such as potassium, calcium and sodium channels), synport/antiport proteins (e.g., glucose transporter); hormones and growth factors (e.g., epidermal growth factor (EGF), fibroblast growth factor (FGF), vascular endothelial growth factor (VEGF), peptide hormones such as insulin, insulin-like growth factor and oxytocin, and steroid hormones such as androgens, estrogens and progesterones), receptors such as transmembrane receptors (e.g., G-protein-coupled receptor, rhodopsin) and intracellular receptors (e.g., estrogen receptor); DNA-binding proteins (e.g., histones, protamines, CI protein); transcription regulators (e.g., c-myc, FOXP2, FOXP3, MyoD and P53); immune system proteins (e.g., immunoglobulins, major histocompatibility antigens and T cell receptors); nutrient storage/transport proteins (e.g., ferritin); chaperone proteins; and enzymes.

The probes, systems, methods and kits of the present disclosure may be used to detect a single target molecule or multiple target molecules. For example, at least 1, 2, 3, 4, 5, 6, 7, 8, 9, 10, 15, 20, 25, 30, 35, 40, 50, 60, 70, 80, 90 or 100 different target molecules may be detected, e.g., in a single reaction.

Advantageously, the probes, systems, methods and/or kits of the present disclosure may be used to detect target molecules having low copy numbers present in a reaction. For example, a copy number of 10-100 (e.g., 10, 15, 20, 25, 30, 35, 40, 45, 50, 55, 60, 65, 70, 75, 80, 85, 90, 95 or 100) may be detected using the probes, systems, methods and/or kits, as provided herein.

Reaction Conditions

Target detection reactions of the present disclosure may proceed as "one-pot synthesis" reactions, whereby a pair of nucleic acid probes is subjected to successive and/or simultaneous reactions (e.g., annealing, strand displacement, extension, etc.) in a single vessel. Such reactions may include a target molecule, a pair of nucleic acid probes, a polymerase and nucleotide triphosphates. Typically, all the components of an reaction are provided in a reaction buffer.

In some embodiments, the polymerase is a DNA polymerase (DNAP), such as a DNA polymerase having DNA strand displacing activity (a strand displacement polymerase). "Strand displacement" describes the ability to displace downstream DNA encountered during synthesis. Examples of polymerases having DNA strand displacement activity that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB ~1M0330). Other polymerases having strand displacement activity may be used. In some embodiments, the polymerase is a RNA polymerase.

In some embodiments, the polymerase is phi29 DNA polymerase. In such embodiments, the reaction conditions may be as follows 1× reaction buffer (e.g. 50 mM Tris-HCl, 10 mM MgCl2, 10 mM (NH4)2SO4, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM (NH4)2SO4, 10 mM KCl, 2 mM MgSO4, 0.1% TRITON® X-100), pH 8.8, incubated at 65° C.

In some embodiments, the polymerase is Bsu DNA polymerase. In such embodiments, the reaction conditions may be as follows: 1× reaction buffer (e.g., 50 mM NaCl, 10 mM Tris-HCl, 10 mM MgCl2, 1 mM DTT), pH 7.9, incubated at 37° C.

The concentration of target sequence, primer(s) and dNTPs in an target detection reaction system may be varied depending, for example, on the particular application (e.g., exponential amplification, real-time monitoring, etc.) and kinetics required for that particular application.

The concentration of primer(s) in an target detection reaction may be, for example, 10 pM to 1000 pM. In some embodiments, the probe concentration in a reaction is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 pM. In some embodiments, the probe concentration in a reaction is 100-200, 100-300, 100-400, 100-500, 100-600, 100-70, 100-800, 100-900 or 100-1000 pM. In some embodiments, the probe concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 pM. In some embodiments, the probe concentration in a reaction is 100, 200, 300, 400, 500, 600, 700, 800, 900 or 1000 pM. The concentration of probe in a reaction may be less than 10 pM or greater than 1000 pM.

The concentration of nucleotide triphosphates (e.g., dNTPs or rNTPs) in an target detection reaction may be, for example, 2-1000 μM. In some embodiments, the dNTP or rNTP concentration in an target detection reaction is 2-10 μM, 2-15 μM, 2-20 μM, 2-25 μM, 2-30 μM, 2-35 μM, 2-40 μM, 2-45 μM, 2-50 μM, 2-55 μM, 2-60 μM, 2-65 μM, 2-70 μM, 2-75 μM, 2-80 μM, 2-85 μM, 2-90 μM, 2-95 μM, 2-100 μM, 2-110 μM, 2-120 μM, 2-130 μM, 2-140 μM, 2-150 μM, 2-160 μM, 2-170 μM, 2-180 μM, 2-190 μM, 2-200 μM, 2-250 μM, 2-300 μM, 2-350 μM, 2-400 μM, 2-450 μM, 2-500 μM, 2-600 μM, 2-700 μM, 2-800 μM, 2-900 μM or 2-1000 μM. For example, the dNTP or rNTP concentration in an target detection reaction may be 2 μM, 5 μM, 10 μM, 15 μM, 20 μM, 25 μM, 30 μM, 35 μM, 4 μM, 45 μM, 50 μM, 55 μM, 60 μM, 65 μM, 70 μM, 75 μM, 80 μM, 85 μM, 90 μM, 95 μM, 100 μM, 105 μM, 110 μM, 115 μM, 120 μM, 125 μM, 130 μM, 135 μM, 140 μM, 145 μM, 150 μM, 155 μM, 160 μM, 165 μM, 170 μM, 175 μM, 180 μM, 185 μM, 190 μM, 195 μM or 200 μM. In some embodiments, the dNTP or rNTP concentration in an amplification reaction is 10-20 μM, 10-30 μM, 10-40 μM, 10-50 μM, 10-60 μM, 10-70 μM, 10-80 μM, 10-90 μM or 10-100 μM.

The kinetics of a target detection reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, a "temperature at which a strand displacing polymerase is active" (and an amplification reaction is performed) may vary from, for example, 4° C. to 65° C. (e.g., 4° C., 25° C., 37° C., 42° C. or 65° C.). In some embodiments, temperature at which a strand displacing polymerase is active is 4-25° C., 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a temperature at which a strand displacing polymerase is active is at room temperature, while in other embodiments, an amplification reaction is performed at 37° C.

An target detection reaction may be performed (incubated) for 1 minute (min) to an hour (hr), or longer. In some embodiments, an target detection reaction is carried out for 1 min, 2 min, 3 min, 4 min, 5 min, 6 min, 7 min, 8 min, 9 min, 10 min, 15 min, 20 min, 25 min, 30 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

In some embodiments, nucleotide triphosphate variants are used. For example, hot start/clean amp dNTPs, phosphorothioate dNTPs, or fluorescent dNTPs. Other nucleotide triphosphate variants may be used.

Reaction buffers that may be used for an target detection reaction include, without limitation, "Thermo-Pol Buffer" (New England Biolabs), phosphate buffered saline (with or without Mg or Na supplementation), any commercial or laboratory-prepared cell media, water or any pH-buffered solution supplemented with cationic salts sufficient for DNA hybridization and polymerase operation. Reaction buffer, in some embodiments, may have a salt concentration of 0.25-15 mM Mg and/or 50-250 mM Na.

Detection

Single-molecules are detected by the presence of an amplifiable nucleic acid molecules (also referred to as a nucleic acid records or simply as "records"). In some embodiments, the records are double-stranded. In some embodiments, the records are single-stranded. The length of the records may vary. For example, a barcoded record may have a length of 30 to 500 nucleotides (or nucleotide base pairs). In some embodiments, a barcoded record has a length of 30 to 100, 30 to 200, 30 to 300, 30 to 400, 50 to 100, 50 to 200, 50 to 300, 50 to 400 or 50 to 500 nucleotides (or nucleotide base pairs). In some embodiments, a barcoded record has a length of 80 to 100 nucleotides (or nucleotide base pairs), or 90 nucleotides (or nucleotide base pairs).

Figure 6:
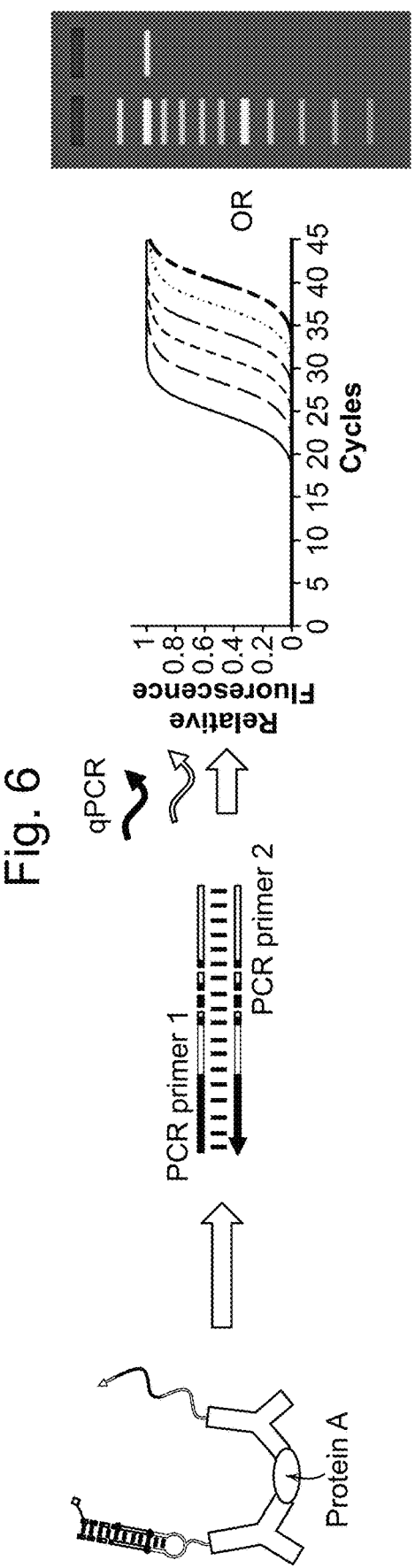
FIG. 6 shows an example of target detection using qPCR or gel electrophoresis.
Figure 7:
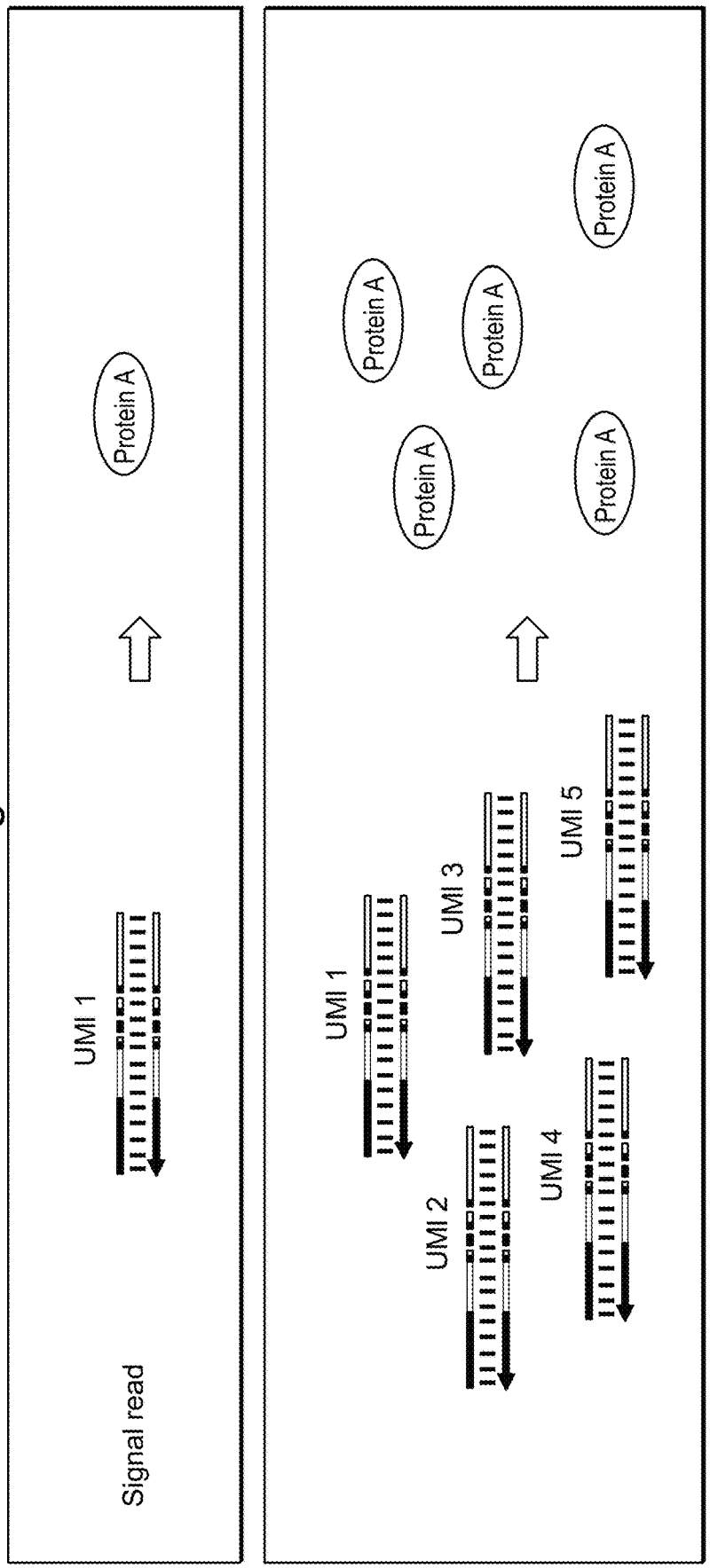
FIG. 7 shows examples of detection of a single target molecule or a number of target molecules. UMI encoded in the product sequence was used to digitally count the number of target molecules.
Figure 9:
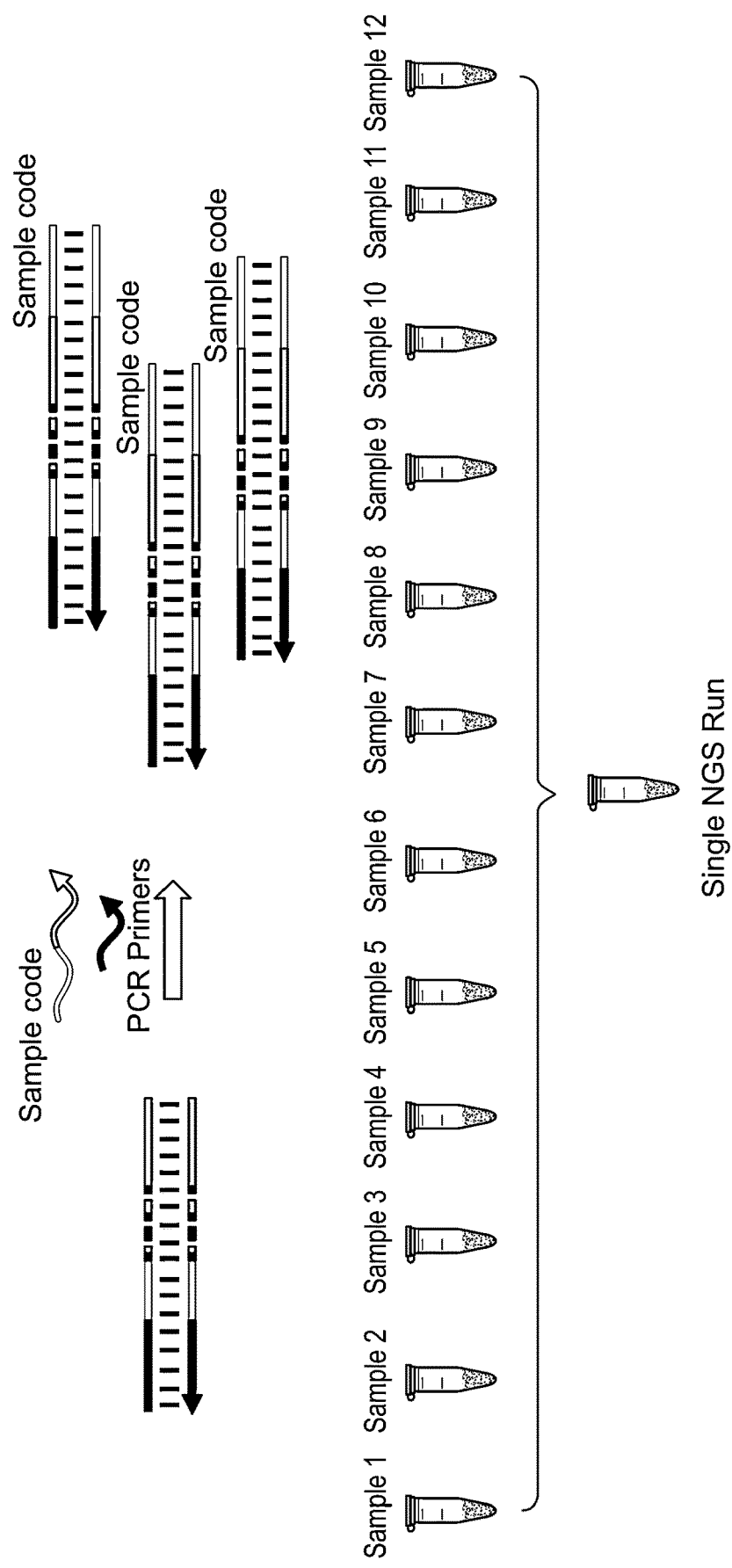
FIG. 9 shows an example of different samples combined and analyzed by a single sequencing reaction.

In some embodiments, barcoded records are "decoded" by direct observation by gel electrophoresis or amplification and quantification by PCR (see, e.g., FIG. 6). High-throughput sequencing is also encompassed by the present disclosure and may be used to detect the number of amplifiable nucleic acid molecules (see. e.g., FIG. 7 and FIG. 9). In some embodiments, primer-binding domains and PCR-primer-binding domains have distinct sequences and can be used to detect multiple different targets in a multiplexed assay format (see, e.g., FIG. 8).

Systems and Kits

Also provided herein are target detection systems and kits. A target detection system or kit may comprise at least one (e.g., at least 2, 3, 4, 5, 6, 7, 8, 9, 10, 20, 50, or 100) pair of nucleic acid probes of the present disclosure. In some embodiments, a target detection system or kit further comprises a primer that is complementary to the 5' primer-binding subdomain of the first nucleic acid probe, and a primer that is at least 95% identical to (or identical to) the 5' primer-binding domain of the second nucleic acid probe.

In some embodiments, a target detection system or kit further comprises a strand displacing polymerase.

In some embodiments, a target detection system or kit further comprises a nucleic acid scavenger probe that comprises a 3' primer-binding domain that is complementary to the 3' primer domain of the second nucleic acid probe. The scavenger probe may comprise, for example, a 3' unpaired domain that is complementary to the 3' primer domain of the second nucleic acid probe.

In some embodiments, a target detection system or kit further comprises at least one (e.g., at least 2, 3, 4, 5, 6, 7, 8, 9, 10, 20, 50, or 100) target molecule (e.g., protein).

Additional Embodiments

Additional embodiments of the present disclosure are represented by the following numbered paragraphs.
1. A pair of nucleic acid probes, comprising:
 (a) a first nucleic acid probe that comprises a
  (i) 5' paired domain comprising a 5' primer-binding subdomain linked to a 3' barcode subdomain, wherein the 3' barcode subdomain is formed by base pairing between a sequence of nucleotides that lacks one of A, T, C or G and a complementary sequence of nucleotides, and
  (ii) a 3' unpaired primer-binding domain,
  wherein a nucleotide corresponding to the nucleotide lacking from the 3' barcode subdomain is located between the 3' barcode subdomain and the 5' primer-binding subdomain, and wherein the 5' primer-binding subdomain comprises a 5' molecule that terminate polymerization, and
 (b) a second nucleic acid probe that comprises a 5' primer-binding domain linked to a 3' primer domain that is complementary to the 3' unpaired primer-binding domain of the first nucleic acid probe. See. e.g., FIG. 2. In some instances, the second nucleic acid probe does not include a barcode domain.
2. The pair of nucleic acid probes of paragraph 1, wherein the first probe is conjugated to a molecule that binds specifically to a first epitope on a target protein, and second probe is conjugated to a molecule that binds specifically to a second epitope on the target protein. In some embodiments, multiple target molecules are detected, thus, the first probe may be conjugated to an affinity molecule that binds specifically to a first target molecule, and second probe may be conjugated to an affinity molecule that binds specifically to a second target molecule.
3. The pair of nucleic acid probes of paragraph 2, wherein the molecules are antibodies or aptamers.

4. A target detection system comprising the pair of nucleic acid probes of any one of paragraphs 1-3.
5. The target detection system of paragraph 4 further comprising
 a primer that is complementary to the 5' primer-binding subdomain of the first nucleic acid probe, and
 a primer that is at least 95% identical to (e.g., at least 96%, 97%, 98%, 99% or 100% identical to) the 5' primer-binding domain of the second nucleic acid probe.
6. The target detection system of paragraph 4 or 5 further comprising a strand displacing polymerase.
7. The target detection system of any one of paragraphs 4-6 further comprising a nucleic acid scavenger probe that comprises a 3' primer-binding domain that is complementary to the 3' primer domain of the second nucleic acid probe.
8. The target detection system of paragraph 7, wherein the scavenger probe comprises a 3' unpaired domain that is complementary to the 3' primer domain of the second nucleic acid probe.
9. The target detection system of any one of paragraphs 4-8 further comprising at least one target molecule.
10. A method of detecting at least one (e.g., a plurality of, e.g., at least 2, 3, 4, 5, 6, 7, 8, 9, or 10) target molecule, comprising:
 incubating in reaction buffer, comprising strand displacing polymerase and optionally at least one target molecule, at a temperature at which the strand displacing polymerase is active.
 (a) the pair of nucleic acid probes of any one of paragraphs 1-3, and
 (b) a mixture of dNTPs that lacks one of dATP, dTTP, dCTP or dGTP, wherein the dNTP that is lacking corresponds to the complement of the nucleotide that is lacking from the 3' barcode subdomain of the first nucleic acid probe;
 optionally adding to the reaction buffer a nucleic acid scavenger probe and incubating the reaction buffer at a temperature at which the strand displacing polymerase is active; and then
 incubating the reaction buffer, in the presence of dATP, dTTP, dCTP and dGTP at a temperature at which the strand displacing polymerase is active, thereby producing a record of an interaction between the pair of nucleic acid probes.
11. The method of paragraph 10 further comprising performing a nucleic acid amplification reaction of the record using a primer that is complementary to the 5' primer-binding subdomain of the first nucleic acid probe and a primer that is at least 95% identical to (e.g., at least 96%, 97%, 98%, 99% or 100% identical to) to the 5' primer-binding domain of the second nucleic acid probe, optionally wherein the amplification reaction in performed in the presence of the pair of nucleic acid probes.
12. A plurality of the pair of nucleic acid probes of any one of paragraphs 1-3, wherein at least one (e.g., at least 2, 3, 4, 5, or more) primer-binding domain is unique, wherein each primer-binding domain is unique, or wherein different barcode subdomain sequences are presence in the plurality.
13. The plurality of paragraph 12, wherein the plurality comprises at least 10 of the pairs of nucleic acid barcode probes.
14. A pair of nucleic acid probes, comprising:
 (a) a first nucleic acid probe that comprises
  (i) a 5' paired domain comprising a 5' primer-binding subdomain linked to a 3' barcode subdomain, wherein the 3' barcode subdomain is formed by base pairing between a sequence of nucleotides that lacks one of A, T, C or G and a complementary sequence of nucleotides, and
  (ii) a 3' unpaired primer-binding domain, wherein a nucleotide corresponding to the nucleotide lacking from the 3' barcode subdomain is located between the 3' barcode subdomain and the 5' primer-binding subdomain; and
(b) a second nucleic acid probe that comprises a 5' primer-binding domain linked to a 3' primer domain that is complementary to the 3' unpaired primer-binding domain of the first nucleic acid probe.

15. A method of detecting a target molecule, comprising:
incubating in reaction buffer, comprising strand displacing polymerase and optionally a target protein, at a temperature at which the strand displacing polymerase is active,
(a) the pair of nucleic acid probes of paragraph 14, and
(b) a mixture of dNTPs that lacks one of dATP, dTTP, dCTP or dGTP, wherein the dNTP that is lacking corresponds to the complement of the nucleotide that is lacking from the 3' barcode subdomain of the first nucleic acid probe; and then
incubating the reaction buffer, in the presence of the dNTP that is lacking from the mixture of dNTPs of (b) at a temperature at which the strand displacing polymerase is active, thereby producing a record of an interaction between the pair of nucleic acid probes.

16. A pair of nucleic acid probes, comprising.
(a) a first nucleic acid probe that comprises
  (i) a 5' paired domain comprising a barcode formed by base pairing between a barcode sequence of nucleotides and a complementary sequence of nucleotides, and a 5' molecule that terminates polymerization, and
  (ii) a 3' unpaired primer-binding domain that comprises a central primer-binding subdomain flanked by a 5' primer-binding subdomain and a barcode subdomain that is identical to the barcode sequence of nucleotides of (i), wherein a molecule that terminates polymerization is located between the 5' primer-binding subdomain of the 3' unpaired domain and the central primer-binding subdomain; and
(b) a second nucleic acid probe that comprises a 5' primer-binding domain linked to a 3' primer domain that is complementary to the 5' primer-binding subdomain of the 3' unpaired primer-binding domain of the first nucleic acid probe.

17. A method of detecting a target molecule, comprising:
incubating in reaction buffer, comprising strand displacing polymerase and optionally a target protein, at a temperature at which the strand displacing polymerase is active,
(a) the pair of nucleic acid probes of paragraph 16, and
(b) a mixture of dNTPs that comprises dATP, dTTP, dCTP or dGTP.

18. A pair of nucleic acid probes, comprising:
(a) a first nucleic acid probe that comprises
  (i) a 5' paired domain comprising a barcode formed by base pairing between a barcode sequence of a nucleotides and a complementary sequence of nucleotides, and a 5' molecule that terminates polymerization, and
  (ii) a central unpaired primer-binding domain, and
  (iii) a 3' paired domain that comprises a 5' paired subdomain and a 3' paired barcode subdomain formed by base pairing between a sequence of nucleotides that is identical to the barcode sequence of nucleotides of (i) and a complementary sequence of nucleotides, and a 5' molecule that terminates polymerization, and
(b) a second nucleic acid probe that comprises a 5' primer-binding domain linked to a 3' primer domain that is complementary to the central unpaired primer-binding domain of the first nucleic acid probe.

19. A method of detecting a target molecule, comprising.
incubating in reaction buffer, comprising strand displacing polymerase and optionally a target protein, at a temperature at which the strand displacing polymerase is active,
(a) the pair of nucleic acid probes of paragraph 18, and
(b) a mixture of dNTPs that comprises dATP, dTTP, dCTP or dGTP.

20. A pair of nucleic acid probes, comprising:
(a) a first nucleic acid probe that comprises
  (i) a 5' paired domain comprising a barcode formed by base pairing between a barcode sequence of nucleotides and a complementary sequence of nucleotides, wherein the 5' paired domain is flanked by a 5' molecule that terminates polymerization and a 3' unpaired primer domain,
  (ii) a central unpaired domain, and
  (iii) a 3' paired domain that comprises a 3' paired barcode subdomain formed by base pairing between a sequence of nucleotides that is identical to the barcode sequence of nucleotides of (i) and a complementary sequence of nucleotides, and a 5' paired subdomain; and
(b) a second nucleic acid probe that comprises a 5' primer-binding domain linked to a 3' primer domain that is complementary to the central unpaired primer-binding domain of the first nucleic acid probe.

21. A method of detecting a target molecule, comprising:
incubating in reaction buffer, comprising strand displacing polymerase and optionally a target protein, at a temperature at which the strand displacing polymerase is active,
(a) the pair of nucleic acid probes of paragraph 20, and
(b) a mixture of dNTPs that comprises dATP, dTTP, dCTP or dGTP.

22. A pair of nucleic acid probes, comprising:
(a) a first nucleic acid probe that comprises a
  (i) a first nucleic acid strand that comprises in the 5' to 3' direction domain b*, a stopper molecule, domain, and toehold domain b, and
  (ii) a second nucleic acid strand that comprises in the 5' to 3' direction domain c*, a stopper molecule, domain b, and toehold domain a, and
  wherein toehold domain b and toehold domain a are unpaired, domain c is complementary to and bound to domain c*, and domain b* is complementary to and bound to domain b; and
(b) a second nucleic acid probe that comprises a nucleic acid strand that comprises in the 5' to 3' direction domain d* and domain a*,
wherein domain a* is complementary to toehold domain a of the first nucleic acid probe. See. e.g., FIG. 28. In some embodiments, domain d is at least 95% (e.g., at least 96%, 97%, 98%, 99%, or 100%) identical to one of the PCR primers used to generate a record for sequencing (see, e.g., FIG. 32).

23. A pair of nucleic acid probes, comprising:
(a) a first nucleic acid probe that comprises a (i) a first nucleic acid strand that comprises domain b*, and
(ii) a second nucleic acid strand that comprises in the 5' to 3' direction domain c, toehold domain b, a stopper molecule, and toehold domain a,
wherein toehold domain a, toehold domain b, and domain c are unpaired, and domain b is complementary to and bound to domain b*,
(b) a second nucleic acid probe that comprises a nucleic acid strand that comprises in the 5' to 3' direction domain d* and domain a*, wherein domain a* is complementary to toehold domain a of the first nucleic acid probe. See, e.g., FIG. 35(1). In some embodiments, domain d is at least 95% (e.g., at least 96%, 97%, 98%, 99%, or 100%) identical to one of the PCR primers used to generate a record for sequencing (see, e.g., FIG. 32).

24. A pair of nucleic acid probes, comprising:
(a) a first nucleic acid probe that comprises a
(i) a first nucleic acid strand that comprises in the 5' to 3' direction domain b*, a stopper molecule, domain c, and toehold domain b, and
(ii) a second nucleic acid strand that comprises in the 5' to 3' direction a stopper molecule, domain b, and toehold domain a, and
wherein toehold domain b, domain c, and domain a are unpaired, and domain b is complementary to and bound to domain b*;
(b) a second nucleic acid probe that comprises a nucleic acid strand that comprises in the 5' to 3' direction domain d* and domain a*,
wherein domain a* is complementary to toehold domain a of the first nucleic acid probe. See, e.g., FIG. 35(2). In some embodiments, domain d is at least 95% (e.g., at least 96%, 97%, 98%, 99%, or 100%) identical to one of the PCR primers used to generate a record for sequencing (see, e.g., FIG. 32).

25. A pair of nucleic acid probes, comprising:
(a) a first nucleic acid probe that comprises a
(i) a first nucleic acid strand that comprises in the 5' to 3' direction domain b*, a stopper molecule, domain c, and toehold domain b, and
(ii) a second nucleic acid strand that comprises in the 5' to 3' direction domain c*, a stopper molecule, domain b, and toehold domain a,
wherein toehold domain b and toehold domain a are unpaired, domain c is complementary to and bound to domain c*, and domain b* is complementary to and bound to domain b; and
(b) a second nucleic acid probe that comprises a nucleic acid strand that comprises in the 5' to 3' direction domain d* and domain a*,
wherein domain a* is complementary to toehold domain a of the first nucleic acid probe. See, e.g., FIG. 35(3). In some embodiments, domain d is at least 95% (e.g., at least 96%, 97%, 98%, 99%, or 100%) identical to one of the PCR primers used to generate a record for sequencing (see, e.g., FIG. 32).

26. A pair of nucleic acid probes, comprising:
(a) a first nucleic acid probe that comprises
(i) a first nucleic acid strand that comprises in the 5' to 3' direction domain c*, a stopper molecule, domain c, and toehold domain b,
wherein toehold domain b is unpaired, and domain c is complementary to and bound to domain c*, and
(ii) a second nucleic acid strand that comprises the 5' to 3' direction domain b*, a stopper molecule, domain b, and toehold domain a, wherein toehold domain a is unpaired, and domain b is complementary to and bound to domain b*; and
(b) a second nucleic acid probe that comprises a nucleic acid strand that comprises in the 5' to 3' direction domain d* and domain a*, wherein domain a* is complementary to toehold domain a of the first nucleic acid probe. See, e.g., FIG. 35(4). In some embodiments, domain d is at least 95% (e.g., at least %, 97%, 98%, 99%, or 100%) identical to one of the PCR primers used to generate a record for sequencing (see, e.g., FIG. 32).

27. The pair of nucleic acid probes of any one of paragraphs 22-26, wherein the first probe is conjugated to an affinity molecule that binds specifically to a first region on a target molecule, and the second probe is conjugated to an affinity molecule that binds specifically to a second region on the target molecule.

28. The pair of nucleic acid probes of paragraph 27, wherein the target molecule is a protein.

29. The pair of nucleic acid probes of paragraph 28, wherein the affinity molecules are antibodies.

30. The pair of nucleic acid probes of paragraph 28, wherein the affinity molecules are aptamers.

31. A target detection system comprising the pair of nucleic acid probes of any one of paragraphs 22-30.

32. The target detection system of paragraph 31 further comprising a primer that is complementary to the domain c* and/or is at least 95% (e.g., at least 96, 97, 98, 99 or 100%) identical to domain v, and a primer that is at least 95% (e.g., at least 9, 97, 98, 99 or 100%) identical to domain d*.

33 The target detection system of paragraph 31 or 32 further comprising a strand displacing polymerase.

34. The target detection system of any one of paragraphs 31-33 further comprising the target molecule.

35. A method of detecting a target molecule, comprising:
incubating in reaction buffer at a temperature at which the strand displacing polymerase is active the pair of nucleic acid probes of any one of paragraphs 22-30, strand displacing polymerase, deoxyribonucleoside triphosphates, and a target molecule to produce a record of an interaction between the pair of nucleic acid probes.

36. The method of paragraph 35 further comprising performing a nucleic acid amplification reaction of the record using a primer that is complementary to the domain c* and/or is at least 95% (e.g., at least 96, 97, 98, 99 or 100%) identical to domain c, and a primer that is at least 95% (e.g., at least 96, 97, 98, 99 or 100%) identical to domain d*.

37. A plurality of the pair of nucleic acid probes of any one of paragraphs 22-30, wherein each primer-binding domain is unique.

38. The plurality of paragraph 37 comprising at least 10 of the pairs of nucleic acid barcode probes.

39. A pair of nucleic acid probes, comprising:
(a) a first nucleic acid probe that comprises
(i) a first nucleic acid strand that comprises in the 5' to 3' direction domain b*, a stopper molecule, domain e, and toehold domain b,
(ii) a second nucleic acid strand that comprises the 5' to 3' direction domain c*, a stopper molecule, domain b, and toehold domain a, and
(iii) a third nucleic acid strand that comprises the 5' to 3' direction domain e*, a stopper molecule, domain c, and toehold domain e, wherein toehold domain b, toehold domain a, and toehold domain e are unpaired, domain e is complementary to and bound to domain e*, domain b is complementary to and bound to domain b*, and domain c is complementary to and bound to domain c*; and (b) a second nucleic acid probe that comprises a nucleic acid strand that comprises in the 5' to 3' direction domain d* and domain a*, wherein domain a* is complementary to toehold domain a of the first nucleic acid probe. See. e.g., FIG. 29. In some embodiments, domain d is at least 95% (e.g., at least 96%, 97%, 98%, 99%, or 100%) identical to one of the PCR primers used to generate a record for sequencing (see, e.g., FIG. 32).

40. A pair of nucleic acid probes, comprising:
    (a) a first nucleic acid probe that comprises
        (i) a first nucleic acid strand that comprises in the 5' to 3' direction a 5' domain, a stopper molecule, a 3' domain, and a toehold domain, and
        (ii) at least one addition nucleic acid strand that comprises in the 5' to 3' direction 5' domain, a stopper molecule, a 3' domain, and a toehold domain, w % herein each toehold domain is unpaired, and each 5' domain of the first nucleic acid probe is complementary to and bound to a single 3' domain of the first nucleic acid probe, and
    (b) a second nucleic acid probe that comprises a nucleic acid strand that comprises in the 5' to 3' direction a 5' domain and a 3' domain, wherein the 3' domain of the second nucleic acid probe is complementary to the toehold domain of the first nucleic acid strand of the first nucleic acid probe. See, e.g., FIG. 29. In some embodiments, the 5' domain of the second nucleic acid probe is at least 95% (e.g., at least 96%, 97%, 98%, 99%, or 1(10%) identical to one of the PCR primers used to generate a record for sequencing (see. e.g., FIG. 32).

41. The pair of nucleic acid probes of paragraph 40, wherein the first probe is conjugated to an affinity molecule that binds specifically to a first region on a target molecule, and the second probe is conjugated to an affinity molecule that binds specifically to a second region on the target molecule.

42. A target detection system comprising the pair of nucleic acid probes of paragraph 40 or 41.

43. The target detection system of paragraph 42 further comprising
    a primer that is complementary to the domain c* and/or is at least 95% identical to domain c; and
    a primer that is at least 95% identical to domain d*.

44. The target detection system of paragraph 42 or 43 further comprising a strand displacing polymerase.

45. The target detection system of paragraph 42 or 43 further comprising the target protein.

46. A method of detecting a target molecule, comprising:
    incubating in reaction buffer at a temperature at which the strand displacing polymerase is active the pair of nucleic acid probes of paragraph 40 or 41, strand displacing polymerase, deoxyribonucleoside triphosphates, and a target molecule to produce a record of an interaction between the pair of nucleic acid probes.

47. The method of paragraph 46 further comprising performing a nucleic acid amplification reaction of the record using a primer that is complementary to the domain c* and/or is at least 95% identical to domain c, and a primer that is at least 95% identical to domain d*.

48. A plurality of the pair of nucleic acid probes of paragraph 40 or 41, wherein each primer-binding domain is unique, or wherein the plurality comprises different primer binding domains.

49. The plurality of paragraph 48 comprising at least 10 of the pairs of nucleic acid barcode probes.

50. The pair, system, or method of any of the preceding paragraphs, wherein the molecules are antibodies, optionally wherein the antibodies are monoclonal antibodies.

51. The pair, system, or method of any of the preceding paragraphs, wherein the molecules are antibodies, optionally w herein the antibodies are polyclonal antibodies.

52. The pair, system, or method of any of the preceding paragraphs, wherein the molecules are aptamers.

53. The pair, system, or method of any of the preceding paragraphs, wherein the antibodies or aptamers have an affinity ($K_D$) for their binding partner (e.g., antigen) of 50 nM or less (e.g., 50 nM, 10 nM, 1 nM, 500 pM, 100 pM, 50 pM, 10 pM, 5 pM, 1 pM or less).

54. The pair, system, or method of any of the preceding paragraphs, wherein the antibodies or aptamers have an affinity ($K_D$) for their binding partner (e.g., antigen) of 5 nM or greater (e.g., 5 nM, 10 nM, 100 nM, 500 nM, 1 uM, or greater), e.g., 5 nM to 1 uM, 5 nM to 500 nM, 5 nM to 100 nM, 10 nM to 100 nM, or 10 nM to 1 uM.

55. A kit comprising the pair of nucleic acid probes of any one of paragraphs 1-3, 14-16, 18, 20, 22-30, and 39-41, or the target detection system of any one of claims 4-9 and 32-34.

EXAMPLES

Example 1. Primer Extension is Specific

Figure 14:
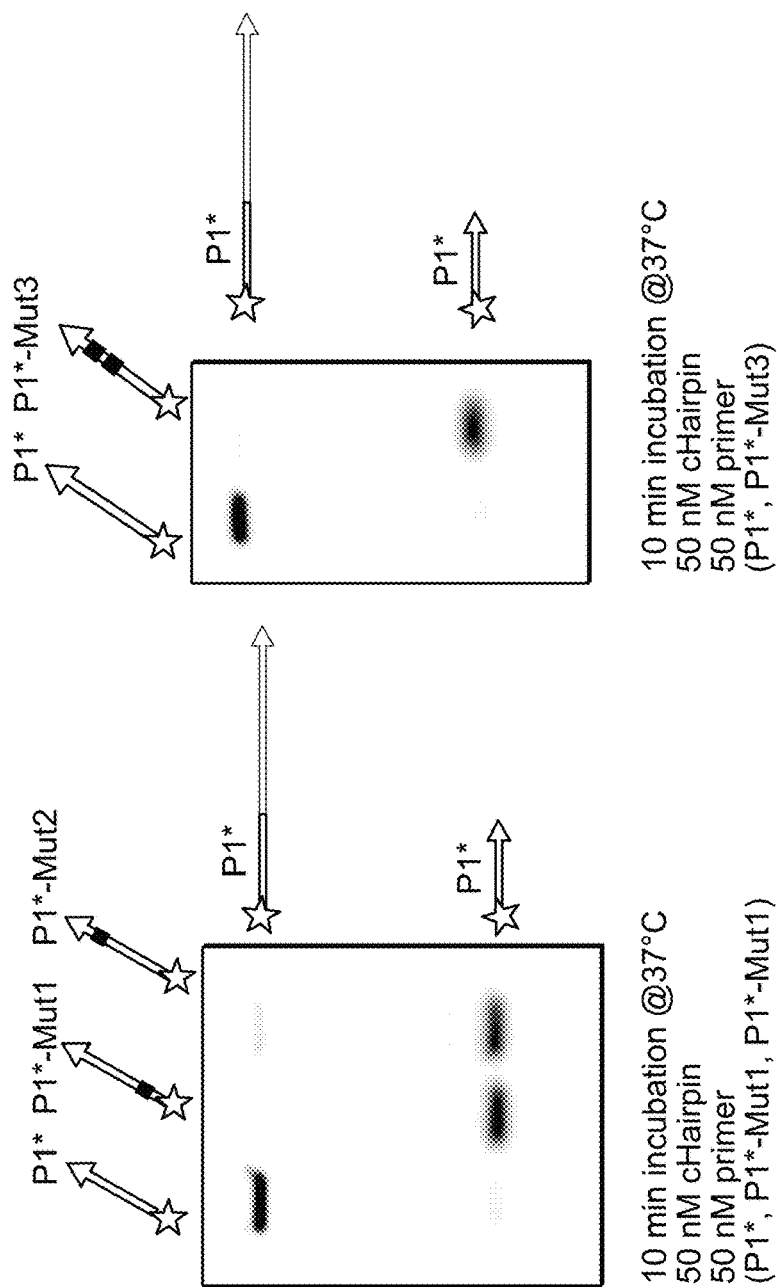
FIG. 14 shows an example of strand displacement-mediated primer extension specificity. The correctly-coded primers are extended efficiently.

This example demonstrates that primers used in the Conditional Primer Extension (CPE) method are specifically extended to append a domain, for example a primer-binding domain. As shown in FIG. 14, primers (arrows) that base-pair to the nucleic acid are extended by the polymerase to append the domain whereas mismatched primers are unable to be extended. Primers were fluorescently labeled for detection by gel electrophoresis.

The schematic on the left shows the generation of a target primer. To examine the specificity of primer extension, the extension of primers with different base pair mutations were compared to the "correct" (target) primer. Gel electrophoresis was performed after incubating 50 nM cHairpin and 50 nM primer (either P1*, P1*-Mut1, P1*-Mut2, or P1*-Mut3) for 10 minutes at 37° C. As shown in FIG. 14, only the correctly-coded primers were extended efficiently. Single-base mismatch in the branch migration domain decreases the primer extension rate significantly.

Example 2. Primer Extension Appends Multiple Domains

This example demonstrates that primers used in the Conditional Primer Extension method are extended to append multiple domains. As shown in FIG. 15, primers that base-pair to a nucleic acid are extended to append the primer-binding domain ("*" domain). The appended domain base-pairs to the nucleic acid and is extended to append a second primer-binding domain. The reaction repeats with base-pairing of the first primer-binding domain ("1*" domain) and second primer-binding domain thereby appending the hairpin onto the primer. Primers were fluorescently labeled for detection by gel electrophoresis.

Example 3. Barcode (UMI) Copying Process

Figure 16:
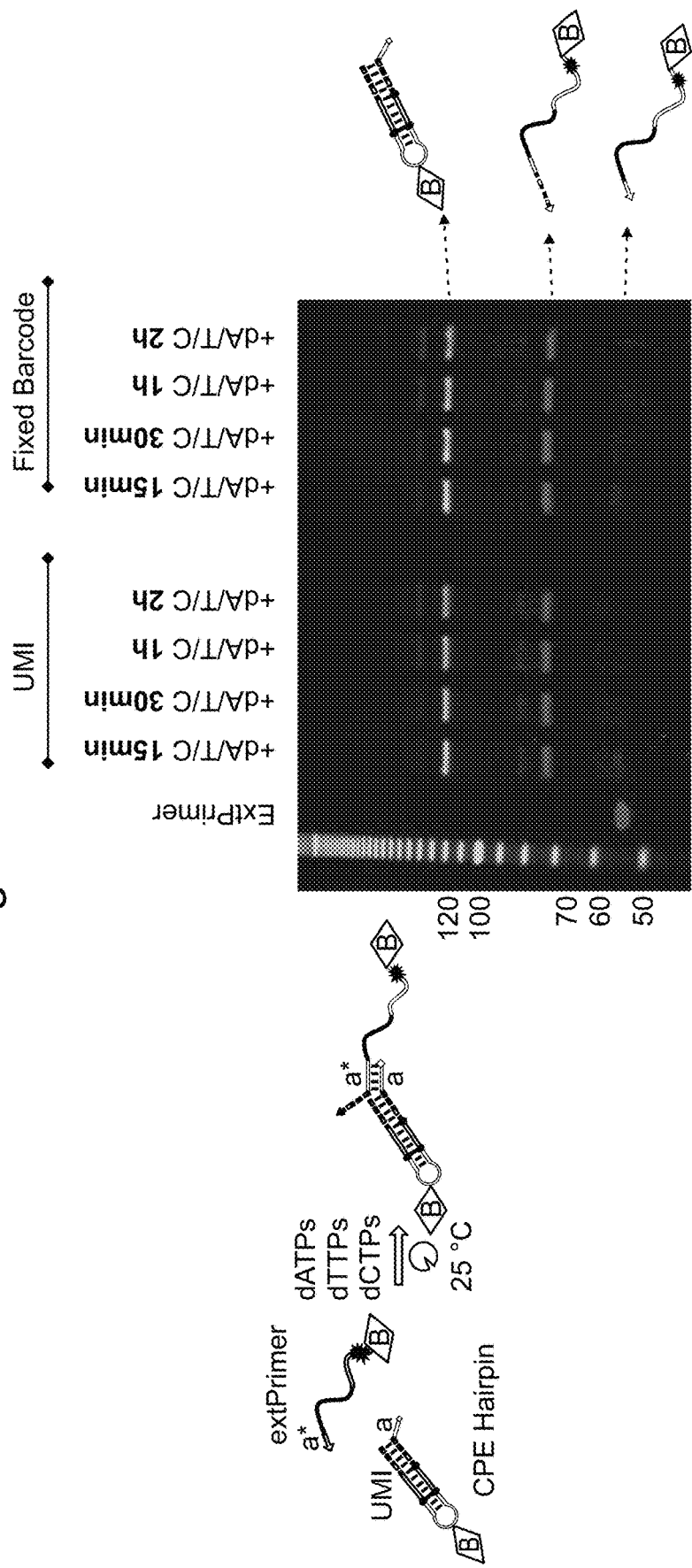
FIG. 16 shows data from a barcode (UM) copying process. The "C-stopper" of the conditional primer exchange (CPE) hairpin is able to stop the polymerase effectively after copying the barcodes on the extension primer.
Figure 21:
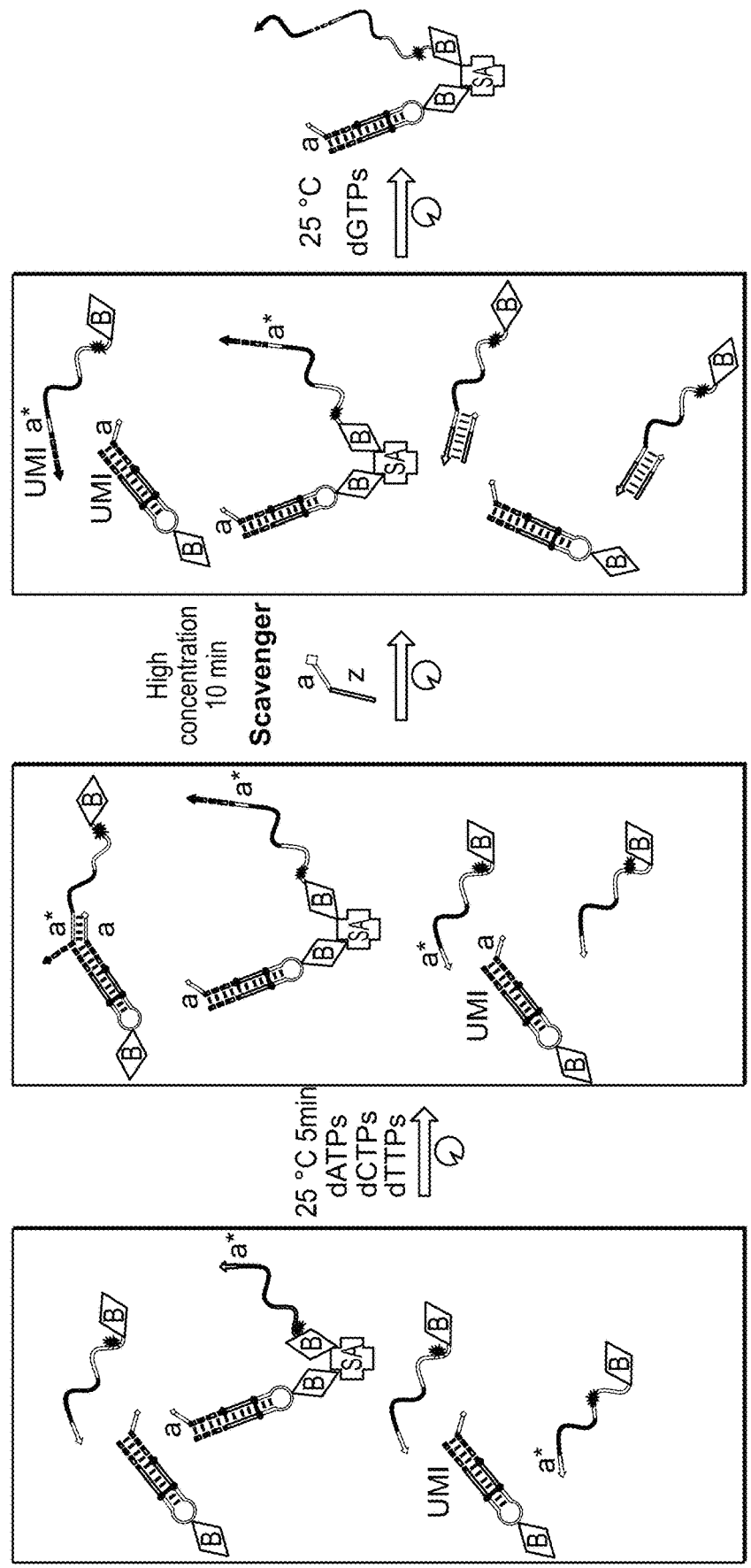
FIG. 21 shows schematics of using scavenger strands to destroy the remaining unextended extension primers following the UMI imprinting stage. A high concentration of scavenger strands is able to shorten the incubation time required for UMI imprinting, when relatively low concentration of probe used.

This example demonstrates a barcode (UMI) copying process. 20 nM CPE hairpin was incubated with 10 nM extension primer (extPrimer) at 25° C. in the presence of dATP, dTTP, and dCTP for the incubation times indicated in FIG. 16. As shown in the figure, the "C-stopper" of the CPE hairpin effectively stopped the polymerase after copying the barcodes on the extension primer.

To explore the effectiveness of UMI, 20 nM CPE hairpin with UMI was incubated with 10 nM extension primer at 20° C. for 1 h and then at 37° C. for 30 min in the presence of dATP, dTTP, dCTP, and polymerase. Then, dGTP was added into the mixture and the mixture was incubated at 20° C. for the times indicated in FIG. 17. Gel electrophoresis showed that, when extension primers imprinted with UMI are not colocalized with CPE hairpin, they generate little to no full records after dissociation from the original hairpin.

As a control experiment, 20 nM CPE hairpin with UMI or fixed barcode was incubated with 10 nM extension primer at 20° C. for 1 h and then at 37° C. for 30 min in the presence of dATP, dTTP, dCTP, and polymerase. Then, dGTP was added into the mixture and the mixture was incubated at 20° C. for 30 min. As shown in FIG. 18, when the extension primers imprinted with fixed barcodes were not colocalized with CPE hairpin, there was a high yield of full records. This was found to be in contrast to the extension primers imprinted with UMI, which did not show full records after dissociating from the CPE hairpin.

To further examine co-localization, 20 nM biotin-labeled CPE hairpin imprinted with UMI were incubated with or without 10 nM streptavidin at 20° C. for 1 h and then at 37° C. for 30 mm in the presence of dATP, dTTP, dCTP, and polymerase. Then, dGTP was added into the mixture and the mixture was incubated at 20° C. for 30 min. As shown in FIG. 19, when extension primers imprinted with UMI were co-localized with CPE hairpin, a high yield of full records after dissociation resulted.

Dissociation kinetics were then characterized. As shown in FIG. 20, single molecule imaging was used to examine UMI barcode-imprinted extension primer. Three extension primers with different UMI barcode lengths were tested, and it was found that UMI-imprinted extension primer dissociates from CPE hairpin rapidly.

Example 4. Background Reaction Suppression

Figure 22:
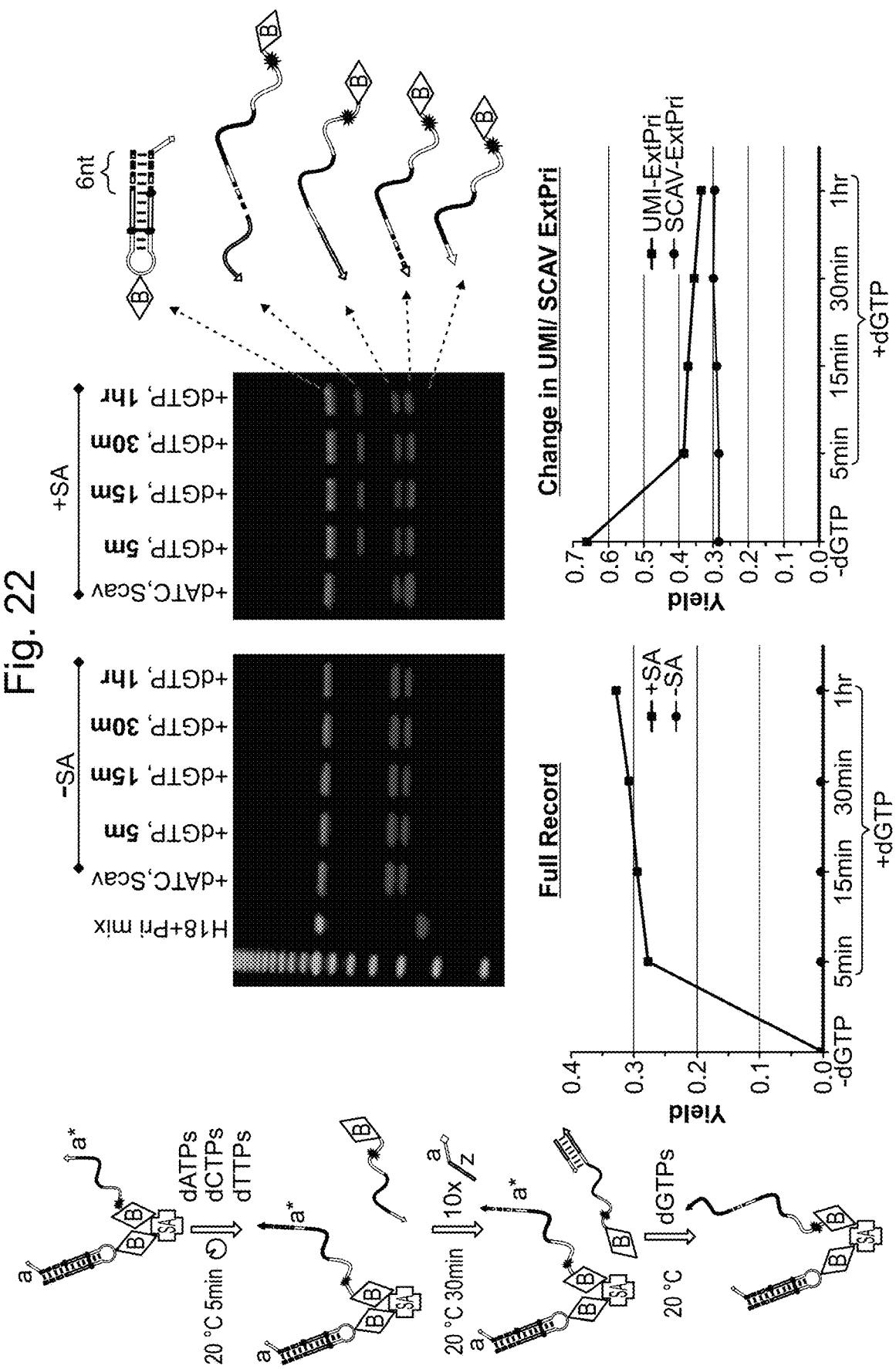
FIG. 22 shows data demonstrating suppression of background record generation in the presence of scavenger strands. Full records were not observed following a one-hour CPE reaction, in the absence of streptavidin. In the presence of streptavidin, however, full records were extended from the UMI imprinted extension primer.

To examine background reaction suppression in scavenger-aided CPE reactions, 10 nM biotin-labeled CPE hairpin imprinted with random barcodes and 10 nM extension primer were incubated with or without 5 nM streptavidin at 25° C. for the indicated times. As shown in FIG. 22, no observable full records were generated over 1 h of reaction time in the absence of streptavidin. The full records were extended from UMI-imprinted extension primer when streptavidin was present.

Figure 23:
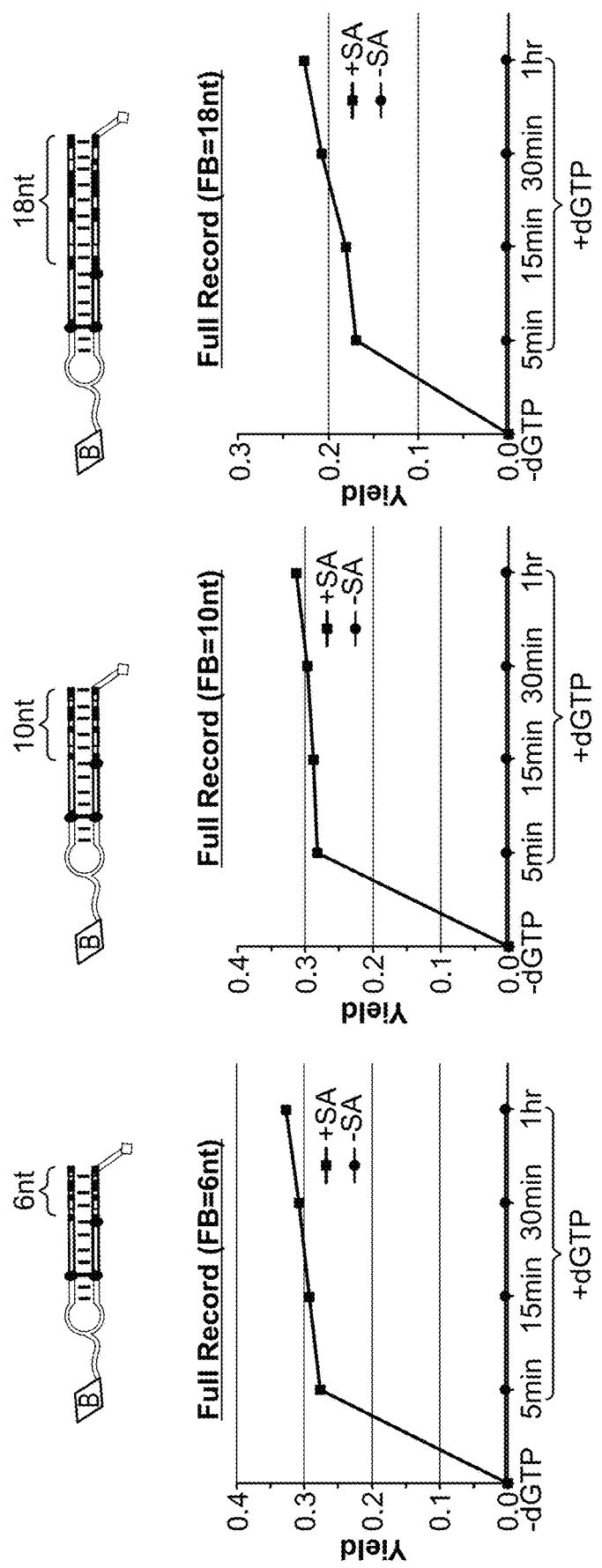
FIG. 23 shows data demonstrating suppression of background record generation in the presence of CPE probes having various barcode lengths. In the absence of streptavidin target, full records were not observed for any of the barcode lengths tested.

Next, the effect of different barcode lengths were examined using the protocol described above. As shown in FIG. 23, when target streptavidin was absent, no observable full records were generated from all the tested CPE probes.

Figure 24:
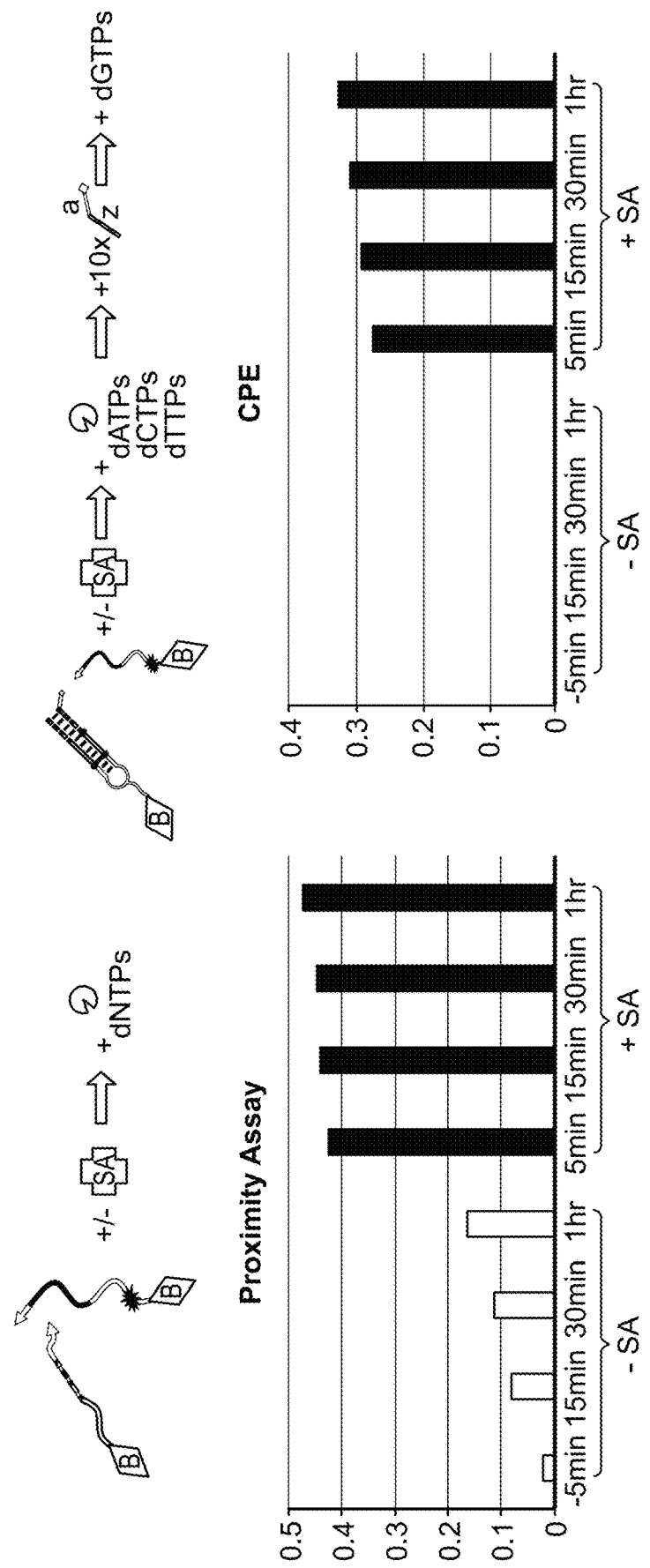
FIG. 24 shows data from experiments comparing background levels observed using a proximity extension assay verses the conditional primer extension (CPE) reaction of the present disclosure. Significant background record levels were observed using the proximity extension reaction, but were not observed using the CPE reaction.

Further, the background signal in the CPE process was compared to another proximity approach. As shown in FIG. 24, significant background reactions occurred in the traditional proximity extension reaction compared to CPE using the same probe concentration and similar probe binding strength. CPE showed negligible background reactions without streptavidin.

Figure 25:
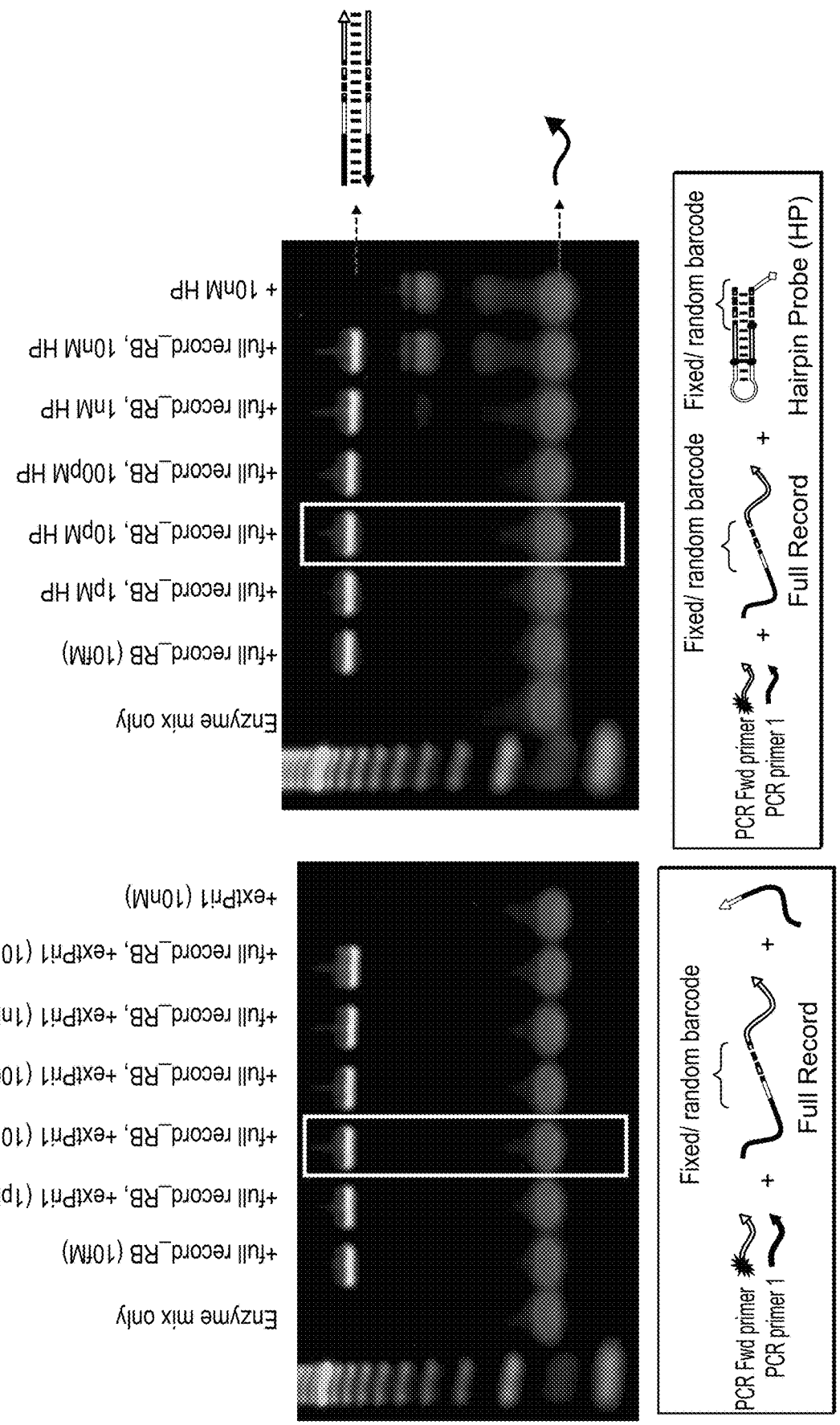
FIG. 25 shows data demonstrating the negligible effect of extension primer and CPE hairpin concentration on the PCR amplification of full records (a CPE probe with 18 nt barcode length was used).

The effect of extension primers and CPE hairpin on the amplification of full records was next examined. Using CPE probes with 18 nucleotide (nt) barcodes, it was shown that different concentrations of CPE hairpin or extension primers resulted in specifically amplified full records; the effect of CPE hairpin and extension primers was negligible (FIG. 25).

Figure 26:
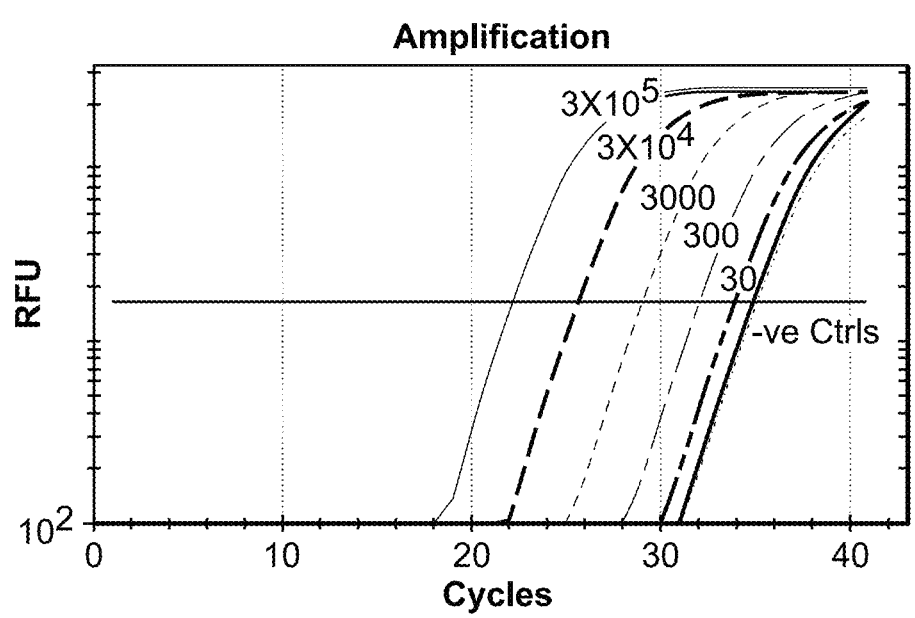
FIG. 26 shows data demonstrating full record amplification in a mixture containing all the components of a CPE reaction, including 10 pM extension primer, 10 pM CPE hairpin and 100 nM scavenger. Surprisingly, less than 30 copies of full records were detected when all the components of CPE reaction present in the PCR mixture.

Next, the effect of all the components of the CPE reaction in the PCR reaction was examined. A mixture containing 10 pM CPE hairpin (with an 18 nt barcode), dATP, dTTP, dCTP, and polymerase was incubated for 30 mm at 20° C. Extension primer (10 pM) was added, and the resulting mixture was incubated for 30 min at 20° C. and then 30 min at 85° C. (to deactivate the polymerase). Amplification was then measured. As shown in FIG. 26, fewer than 30 copies of full records were easily detected when all of the components of the CPE reaction were present in the PCR mixture.

Figure 27:
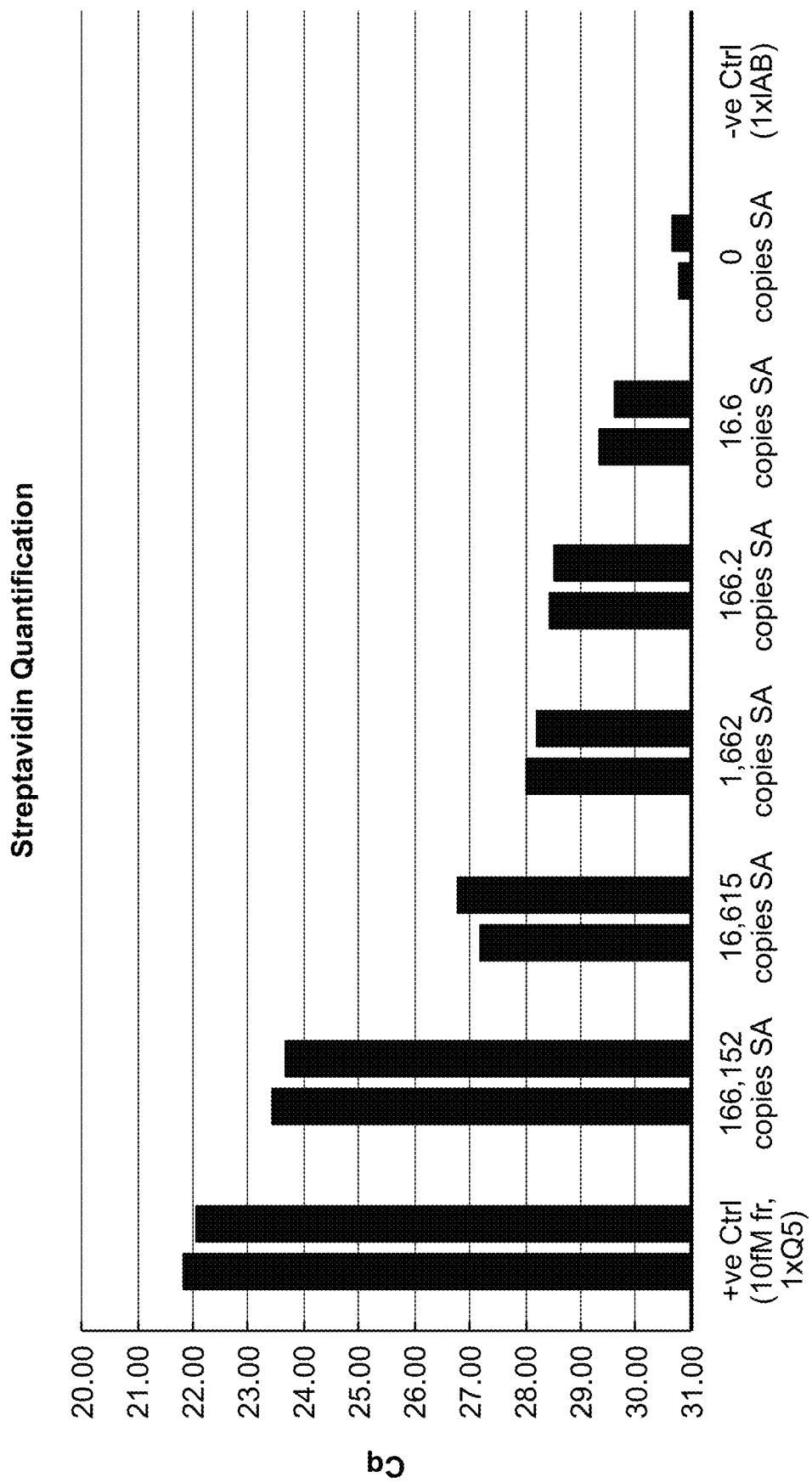
FIG. 27 shows data demonstrating the sensitivity of a CPE reaction. Streptavidin (SA) was detected using biotin-labeled CPE probes, and the background signal generated (0 copy SA) was very low. Approximately 16 copies of streptavidin were detected.

Background signal was also examined using streptavidin detection with biotin-labeled CPE probes comprising 18 nt barcodes. As shown in FIG. 27, the background signal generated (0 copy streptavidin) w as very low, as approximately 16 copies of streptavidin were detected. The two bars in FIG. 27 represent two repeats.

Example 5. Successive Proximity Extension and Expedited Dissociation (SPEED)

Examples of Successive Proximity Extension and Expedited Dissociation (SPEED) are shown in FIGS. 28 and 29. FIG. 28 shows a double-extension (DE) version, while FIG. 29 shows a triple-extension (TE) version. The extension number refers to the number of toeholds on the probe. As the toehold number increases, the theoretical limit of detection (LOD) also increases, according to the following formula.

$$LOD = 3\alpha \frac{([A] + K_{D(A)})([B]_0 + K_{D1B1})}{C_{L(AB)}} \cdot \frac{[A]_0^2}{C_{L(AB)}^2},$$

where $\alpha$=noise/background signal, $C_{L(AB)}$=local concentration when antibody A and B bind on a same target protein, $[A]_0$, $[B]_0$=initial concentrations of antibody A and B, $K_{D(A)}$, $K_{D(B)}$=$K_D$ value of antibody A and B, and where the exponent of "2" ($[A]_0^2$ and $C_{L(AB)}^2$ pertains to a toehold number of 3 (for toehold numbers of "n," the exponent in the above equation would be "n−1").

The SPEED (DE) reaction mechanism was explored using biotin-labeled SPEED probes and streptavidin as a target, 10 nM biotin-labeled probe and 10 nM biotin-labeled primers were incubated at 37° C. in the presence (5 nM) or absence of streptavidin at 37° C. for the times indicated in FIG. 30. Two extension steps were observed on the gel when streptavidin was present in the reaction, as shown in FIG. 30. Quantification of the gel data showed a dramatically increased signal-to-background ratio when the second extension product was the reaction signal.

Figure 32:
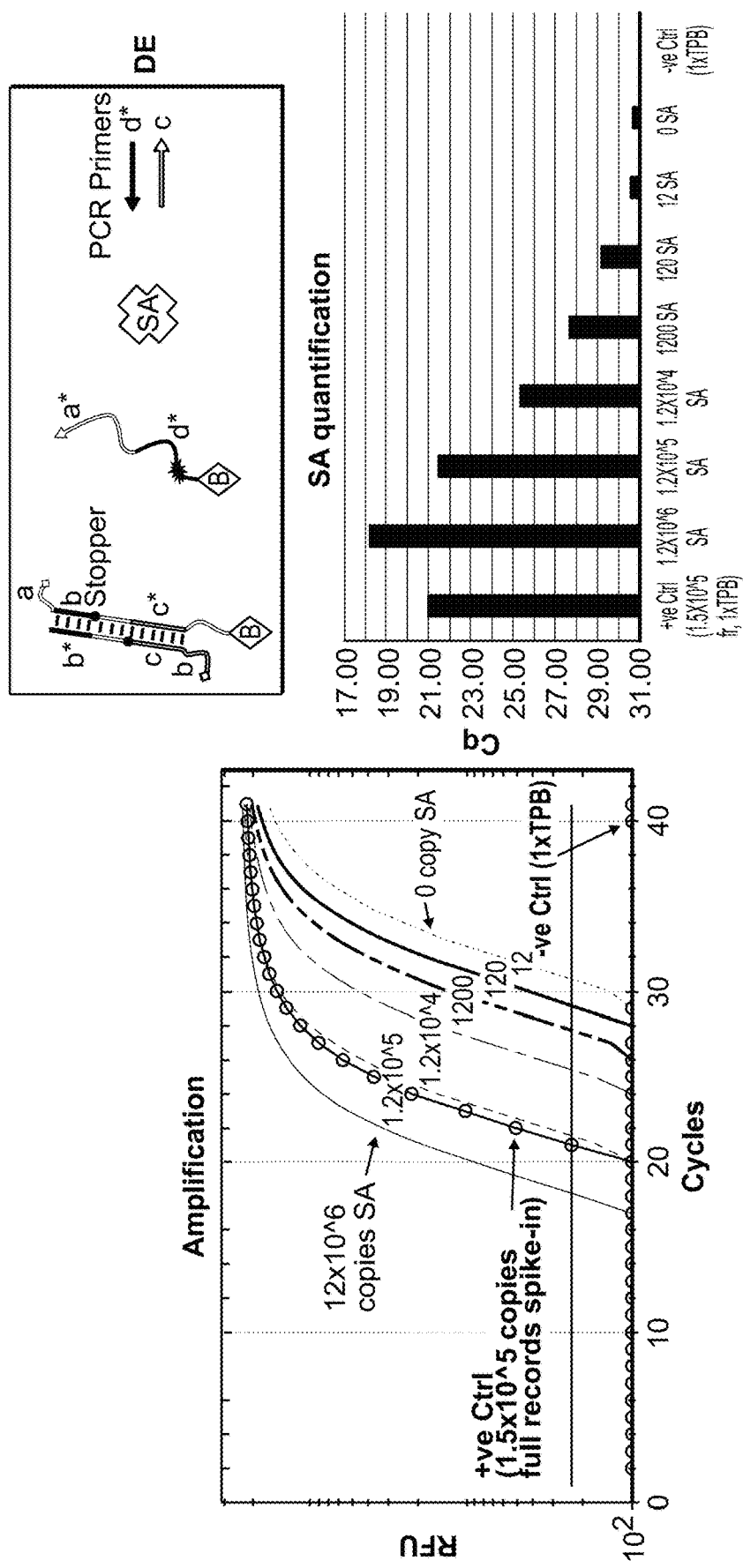
FIG. 32 shows data demonstrating the sensitivity of a SPEED reaction (by qPCR). The reaction was able to detect as low as ~120 copies of streptavidin.

The effect of different lengths and sequences of the two toeholds of SPEED (DE) probes was examined using the same protocol described above. As shown in FIG. 31, there were no observable products from the first and second extensions generated when streptavidin was absent. In contrast, there was a high yield of second extension products, which were quickly generated in the presence of streptavidin. The SPEED reaction was also shown to perform well under room temperature (RM) conditions. The other reactions were incubated at 37° C.

qPCR was then used to examine the sensitivity of the reaction with low concentrations of probe, 50 pM biotin-labeled SPEED probes were incubated at 37° C. with streptavidin, biotin-labeled primers, and PCR primers. As shown in FIG. 32, the reaction was able to detect approximately 120 copies of streptavidin readily.

The ability to eliminate possible background signal from PCR amplification process was then examined by comparing the SPEED probe system to the traditional PEA probe system. As depicted in FIG. 33, when a high concentration of probe is required to boost the binding between affinity probes and targets, the PEA probe would introduce background signal during PCR amplification due to the complementarity of the toehold domain. In contrast, the SPEED probe, equipped with C-stoppers, does not introduce background signal during the PCR amplification process because the extension sequence generated matches no PCR primer sequences and therefore cannot be amplified by the PCR primers.

The reduced background noise using high concentrations of SPEED probe was further examined in FIGS. 34A-34B. As shown in FIG. 34A, gel data demonstrates there was no observable full record amplification after 25 cycles of PCR in the probe concentration range from 1 pM to 1 nM, while FIG. 34B shows qPCR data demonstrating that the SPEED reaction is still able to detect as low as approximately 1200 copies of streptavidin when 1 nM of biotin-labeled SPEED probes are applied. The SPEED reactions were incubated at 37° C. Data from two repeats are shown.

SPEED probes can comprise a number of different designs. Some examples of probes designed to produce the same reporter sequence are given in FIG. 35. Panel 1 shows two toeholds on the same strand of the SPEED probe and the second extension domain "c" is in single-stranded form. Panel 2 shows two toeholds on different strands of SPEED probe and the second extend domain "c" is in single-stranded form. Panel 3 shows an example of eliminating the space between the stoppers of the SPEED probe. Panel 4 shows that the first and second extension domains "b" "c" can be separate to two probes conjugated on the same affinity molecule.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition for producing a nucleic acid, the composition comprising:
   (a) a strand displacing polymerase and a mixture of dNTPs;
   (b) a nucleic acid probe linked to a first target-binding molecule, wherein the nucleic acid probe comprises, in the following order, a first toehold domain, a first double-stranded domain, a first stopper, a second double-stranded domain, a second stopper, a third double-stranded domain, and a second toehold domain, wherein the first stopper and the second stopper are molecules or modifications that terminate polymerization by the strand displacing polymerase; and
   (c) a nucleic acid primer strand linked to a second target-binding molecule, wherein the nucleic acid primer strand comprises a first single-stranded primer domain that can bind to the first toehold domain of the nucleic acid probe.

2. The composition of claim 1, further comprising:
   (d) a target protein that binds to the first target-binding molecule and/or the second target-binding molecule.

3. The composition of claim 2, wherein the target protein binds to the first target binding molecule and the second target-binding molecule.

4. The composition of claim 1, wherein:
   (i) the mixture of dNTPs lacks one dNTP chosen from: dATP, dTTP, dCTP, and dGTP; and
   (ii) the first stopper and/or second stopper are/is complements or a complement of the dNTP lacking from the mixture of dNTPs.

5. The composition of claim 1, wherein the first stopper and/or the second stopper are/is synthetic non-DNA linkers or modified bases or a synthetic non-DNA linker or a modified base.

6. The composition of claim 1, wherein the strand displacing polymerase is phi29 DNA polymerase; Bst DNA polymerase; or Bsu DNA polymerase.

7. The composition of claim 1, wherein (1) the mixture of dNTPs consists of dATP, dTTP, and dCTP, and the first stopper and/or second stopper are/is dC; (2) the mixture of dNTPs consists of dATP, dTTP, and dGTP, and the first stopper and/or second stopper are/is dG; (3) the mixture of dNTPs consists of dTTP, dCTP, and dGTP, and the first stopper and/or second stopper are/is dT; or (4) the mixture of dNTPs consists of dATP, dCTP, and dGTP, and the first stopper and/or second stopper are/is dA.

8. The composition of claim 1, wherein the first target-binding molecule and/or the second target-binding molecule are/is antibodies or aptamers or an antibody or an aptamer.

9. The composition of claim 1, wherein the reaction mixture further comprises a pair of primers that bind to the nucleic acid.

* * * * *